United States Patent
Johnson et al.

(10) Patent No.: US 11,752,221 B2
(45) Date of Patent: Sep. 12, 2023

(54) BRUSH-ARM STAR POLYMER IMAGING AGENTS AND USES THEREOF

(71) Applicants: Massachusetts Institute of Technology, Cambridge, MA (US); Board of Regents of the University of Nebraska, Lincoln, NE (US)

(72) Inventors: Jeremiah A. Johnson, Boston, MA (US); Hung Vanthanh Nguyen, Braintree, MA (US); Andrzej Rajca, Lincoln, NE (US)

(73) Assignees: Massachusetts Institute of Technology, Cambridge, MA (US); Board of Regents of the University of Nebraska, Lincoln, NE (US)

( * ) Notice: Subject to any disclaimer, the term of this patent is extended or adjusted under 35 U.S.C. 154(b) by 352 days.

(21) Appl. No.: 16/024,643

(22) Filed: Jun. 29, 2018

(65) Prior Publication Data

US 2019/0038782 A1  Feb. 7, 2019

Related U.S. Application Data

(60) Provisional application No. 62/528,026, filed on Jun. 30, 2017.

(51) Int. Cl.
| | | |
|---|---|---|
| *A61K 49/12* | (2006.01) | |
| *A61K 49/00* | (2006.01) | |
| *A61K 49/20* | (2006.01) | |
| *A61K 49/18* | (2006.01) | |
| *B82Y 5/00* | (2011.01) | |

(52) U.S. Cl.
CPC ........ *A61K 49/124* (2013.01); *A61K 49/0032* (2013.01); *A61K 49/0054* (2013.01); *A61K 49/0093* (2013.01); *A61K 49/186* (2013.01); *A61K 49/1881* (2013.01); *A61K 49/20* (2013.01); *A61K 2123/00* (2013.01); *B82Y 5/00* (2013.01)

(58) Field of Classification Search
CPC ........................ A61K 49/124; A61K 49/0054
See application file for complete search history.

(56) References Cited

U.S. PATENT DOCUMENTS

| | | |
|---|---|---|
| 3,256,308 A | 6/1966 | Pawloski et al. |
| 3,337,598 A | 8/1967 | Pawloski et al. |
| 4,359,425 A | 11/1982 | Totani et al. |
| 4,510,136 A | 4/1985 | Moberg et al. |
| 5,811,515 A | 9/1998 | Grubbs et al. |
| 8,067,505 B2 | 11/2011 | Harris et al. |
| 9,381,253 B2 | 7/2016 | Johnson et al. |
| 9,447,129 B2 | 9/2016 | Johnson et al. |
| 9,822,216 B2 | 11/2017 | Mahanthappa et al. |
| 10,023,536 B2 | 7/2018 | Johnson et al. |
| 10,105,449 B2 | 10/2018 | Johnson et al. |
| 10,153,513 B2 | 12/2018 | Grubbs et al. |
| 10,159,749 B2 | 12/2018 | Johnson et al. |
| 10,683,387 B2 | 6/2020 | Johnson et al. |
| 10,716,858 B2 | 7/2020 | Johnson et al. |
| 10,792,373 B2 | 10/2020 | Johnson et al. |
| 10,793,683 B2 | 10/2020 | Johnson et al. |
| 10,799,594 B2 | 10/2020 | Johnson et al. |
| 10,961,338 B2 | 3/2021 | Johnson et al. |
| 10,973,847 B2 | 4/2021 | Johnson et al. |
| 10,988,491 B2 | 4/2021 | Johnson et al. |
| 2002/0183473 A1 | 12/2002 | Matyjaszewski et al. |
| 2002/0198328 A1 | 12/2002 | L'Alloret |
| 2003/0004364 A1 | 1/2003 | Yaghi et al. |
| 2003/0065023 A1 | 4/2003 | Swindell et al. |
| 2005/0109976 A1 | 5/2005 | Fuchs et al. |
| 2008/0063937 A1 | 3/2008 | Lee et al. |
| 2011/0166128 A1 | 7/2011 | Remenar et al. |
| 2011/0243848 A1 | 10/2011 | Appel et al. |
| 2011/0300219 A1 | 12/2011 | Lippard et al. |
| 2013/0296491 A1 | 11/2013 | Xia et al. |
| 2013/0324666 A1 | 12/2013 | Yan et al. |
| 2014/0024137 A1 | 1/2014 | Arya et al. |
| 2014/0142249 A1 | 5/2014 | Cho et al. |

(Continued)

FOREIGN PATENT DOCUMENTS

| | | |
|---|---|---|
| CN | 101412792 A | 4/2009 |
| CN | 103819486 A | 5/2014 |

(Continued)

OTHER PUBLICATIONS

Kauffman et al. "Fluorescence-Based Assays for Measuring Doxorubicin in Biological Systems", React Oxyg Species (Apex). 2016 ; 2(6): 432-439 (Year: 2016).*

(Continued)

*Primary Examiner* — James W Rogers
(74) *Attorney, Agent, or Firm* — Wolf, Greenfield & Sacks, P.C.

(57) ABSTRACT

Disclosed are methods, compositions, reagents, systems, and kits to prepare nitroxide-functionalized brush-arm star polymer organic radical contrast agent (BASP-ORCA) as well as compositions and uses thereof. Various embodiments show that BASP-ORCA display unprecedented per-nitroxide and per-molecule transverse relaxivities for organic radical contrast agents, exceptional stability, high water solubility, low in vitro and in vivo toxicity, and long blood compartment half-life. These materials have the potential to be adopted for tumor imaging using clinical high-field $^1$H MRI techniques.

25 Claims, 17 Drawing Sheets

(56) References Cited

U.S. PATENT DOCUMENTS

| | | |
|---|---|---|
| 2014/0308234 A1 | 10/2014 | Johnson et al. |
| 2015/0225438 A1 | 8/2015 | Johnson et al. |
| 2016/0024246 A1 | 1/2016 | Mahanthappa et al. |
| 2016/0289392 A1 | 10/2016 | Grubbs et al. |
| 2016/0296631 A1 | 10/2016 | Johnson et al. |
| 2016/0361702 A1 | 12/2016 | Cohen et al. |
| 2017/0000909 A1 | 1/2017 | Gianneschi et al. |
| 2017/0073311 A1 | 3/2017 | Johnson et al. |
| 2017/0348431 A1 | 12/2017 | Johnson et al. |
| 2018/0030213 A1 | 2/2018 | Johnson et al. |
| 2018/0036415 A9 | 2/2018 | Johnson et al. |
| 2018/0094099 A1 | 4/2018 | Johnson et al. |
| 2018/0312634 A1 | 11/2018 | Chung et al. |
| 2019/0030067 A1 | 1/2019 | Johnson et al. |
| 2019/0038751 A1 | 2/2019 | Johnson et al. |
| 2019/0054187 A1 | 2/2019 | Johnson et al. |
| 2019/0192672 A1 | 6/2019 | Johnson et al. |
| 2020/0055879 A1 | 2/2020 | Johnson et al. |
| 2020/0123297 A1 | 4/2020 | Johnson et al. |
| 2020/0261596 A1 | 8/2020 | Ali et al. |
| 2020/0362095 A1 | 11/2020 | Johnson et al. |
| 2020/0369685 A1 | 11/2020 | Johnson et al. |
| 2021/0023224 A1 | 1/2021 | Johnson et al. |
| 2021/0113701 A1 | 4/2021 | Johnson et al. |
| 2021/0147598 A1 | 5/2021 | Johnson et al. |
| 2021/0220391 A1 | 7/2021 | Johnson et al. |
| 2021/0284664 A1 | 9/2021 | Johnson et al. |
| 2021/0317143 A9 | 10/2021 | Johnson et al. |
| 2022/0370628 A9 | 11/2022 | Johnson et al. |

FOREIGN PATENT DOCUMENTS

| | | |
|---|---|---|
| CN | 108727581 A | 11/2018 |
| DE | 2263509 A1 | 7/1974 |
| EP | 3315126 A1 | 5/2018 |
| EP | 3584245 A1 | 12/2019 |
| KR | 20120113694 A | 10/2012 |
| WO | WO 2001/032652 A2 | 5/2001 |
| WO | WO 2010/047765 A2 | 4/2010 |
| WO | WO 2011/084846 A1 | 7/2011 |
| WO | WO 2013/010676 A2 | 1/2013 |
| WO | WO 2013/169739 A1 | 11/2013 |
| WO | WO 2014/004884 A1 | 1/2014 |
| WO | WO 2014/169073 A1 | 10/2014 |
| WO | WO 2016/023036 A1 | 2/2016 |
| WO | WO 2016/172386 A1 | 10/2016 |
| WO | WO 2017/180834 A1 | 10/2017 |
| WO | WO 2018/106738 A1 | 6/2018 |
| WO | WO 2018/149359 A1 | 8/2018 |
| WO | WO 2019/006426 A2 | 1/2019 |

OTHER PUBLICATIONS

Sowers et al. "Redox-responsive branched-bottlebrush polymers for in vivo MRI and fluorescence imaging" Nat Commun 5, 5460 (2014), Supp. Cont. (Year: 2014).*
*U.S. Appl. No. 14/249,254, filed Apr. 9, 2014, Johnson et al.
*U.S. Appl. No. 15/190,018, filed Jun. 22, 2016, Johnson et al.
*U.S. Appl. No. 15/616,498, filed Jun. 7, 2017, Johnson et al.
*U.S. Appl. No. 16/167,412, filed Oct. 22, 2018, Johnson et al.
*U.S. Appl. No. 16/024,665, filed Jun. 29, 2018, Johnson et al.
*U.S. Appl. No. 16/024,662, filed Jun. 29, 2018, Johnson et al.
PCT/US2014/033554, Oct. 22, 2015, International Preliminary Report on Patentability.
EP 14782253.0, Nov. 11, 2016, Extended European Search Report.
PCT/US2017/036447, Sep. 7, 2017, International Search Report and Written Opinion.
PCT/US2017/036447, Dec. 20, 2018, International Preliminary Report on Patentability.
PCT/US2017/064784, Mar. 1, 2018, International Search Report and Written Opinion.
PCT/US2018/040488, Oct. 15, 2018, International Search Report and Written Opinion.
PCT/US2018/040494, Oct. 10, 2018, International Search Report and Written Opinion.
PCT/US2018/040496, Nov. 21, 2018, Invitation to Pay Additional Fees.
International Search Report and Written Opinion for Application No. PCT/US2018/040496 dated Jan. 14, 2019.
International Preliminary Report on Patentability for PCT/US2018/040488, dated Jan. 9, 2020.
International Preliminary Report on Patentability for PCT/US2018/040494, dated Jan. 9, 2020.
International Preliminary Report on Patentability for PCT/US2018/040496, dated Jan. 9, 2020.
Bates et al., Polarity-switching top coats enable orientation of sub-10-nm block copolymer domains. Science. Nov. 9, 2012;338(6108):775-9. doi: 10.1126/science.1226046.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Cheng et al., Well-defined diblock macromonomer with a norbornene group at block junction: anionic living linking synthesis and ring-opening metathesis polymerization. Macromol. Mar. 4, 2010;43(7):3153-5.
Chiang et al., Vitamin D for the prevention and treatment of pancreatic cancer. World J Gastroenterol. Jul. 21, 2009;15(27):3349-54.
Dalsin et al., Bottlebrush block polymers: Quantitative theory and experiments. ACS Nano. Nov. 6, 2015;9(12):12233-45.
Davis et al., Atom transfer radical polymerization of tert-butyl acrylate and preparation of block copolymers. Macromol. May 30, 2000;33(11):4039-47.
Fenlon et al., The Thread & Cut Method: Syntheses of Molecular Knot Precursors. Eur J Org Chem. Jun. 2008;2008(18):3065-3068.
Frechet. Functional polymers and dendrimers: reactivity, molecular architecture, and interfacial energy. Science. Mar. 25, 1994;263(5154):1710-5.
Gestwicki et al., Influencing receptor-ligand binding mechanisms with multivalent ligand architecture. J Am Chem Soc. Dec. 18, 2002;124(50):14922-33.
Godugu et al., Abstract 2139: Effect of telmisartan on triple negative breast cancer (TNBC) and lung cancer tumor progression and intratumoral distribution of nanoparticles. Cancer Res. 2013;73(8).
Grahovac et al., Abstract B41: The angiotensin receptor blocker telmisartan inhibits the growth of pancreatic ductal adenocarcinoma and improves survival. Cancer Res. 2016;76(24).
Grason et al., Geometric theory of diblock copolymer phases. Phys Rev Lett. Jul. 31, 2003;91(5):058304.
Gu et al., Mechanism of the reactions of dimethylsilylene with oxetanes. J. Am. Chem. Soc. 1980, 102, 5, 1641-1644.
Hawker et al., Preparation of polymers with controlled molecular architecture. A new convergent approach to dendritic macromolecules. J Am Chem Soc. Oct. 1990;112(21):7638-47.
Heroguez et al., Novel Styrene-Butadiene Copolymers by Ring-Opening Metathesis Polymerization. Macromol. Oct. 3, 2000;33(20):7241-8.
Hoogenboom et al., l-Lactide Polymerization Utilizing a Hydroxy-Functionalized 3,6-Bis(2-pyridyl)pyridazine as Supramolecular (Co)initiator: Construction of Polymeric [2 × 2] Grids. Macromolecules, 2003;36(13):4743-9. DOI: 10.1021/ma034119e.
Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.
Jakubowski et al., Activators regenerated by electron transfer for atom transfer radical polymerization of styrene. Macromol. Jan. 10, 2006;39(1):39-45.
Jeong et al., Highly tunable self-assembled nanostructures from a poly (2-vinylpyridine-b-dimethylsiloxane) block copolymer. Nano Lett. Sep. 27, 2011;11(10):4095-101.
Jiang et al., Morphology and Phase Diagram of Comb Block Copolymer A m+ 1 (BC) m. J Phys Chem B. May 7, 2009;113(21):7462-7.

(56) References Cited

OTHER PUBLICATIONS

Jung et al., Orientation-controlled self-assembled nanolithography using a polystyrene-polydimethylsiloxane block copolymer. Nano Lett. Jul. 11, 2007;7(7):2046-50.
Kale et al., Supramolecular assemblies of amphiphilic homopolymers. Langmuir. May 19, 2009;25(17):9660-70.
Kawamoto et al., Loops versus branch functionality in model click hydrogels. Macromol. Dec. 1, 2015;48(24):8980-8.
Lee et al., Novel phase morphologies in a microphase-separated dendritic polymer melt. Macromol. Jan. 12, 2009;42(3):849-59.
Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.
Li et al., Dynamic cylindrical assembly of triblock copolymers by a hierarchical process of covalent and supramolecular interactions. J Am Chem Soc. Jan. 4, 2011;133(5):1228-31.
Li et al., Efficient synthesis of narrowly dispersed amphiphilic double-brush copolymers through the polymerization reaction of macromonomer micelle emulsifiers at the oil-water interface. Polym Chem. 2016;7(27):4476-85.
Li et al., Facile syntheses of cylindrical molecular brushes by a sequential RAFT and ROMP "grafting-through" methodology. J Polym Sci A Polym Chem. Oct. 15, 2009;47(20):5557-5563.
Li et al., Synthesis of Hetero-Grafted Amphiphilic Diblock Molecular Brushes and Their Self-Assembly in Aqueous Medium. Macromolecules. 2010;43(3):1182-1184.
Li et al., Well-defined amphiphilic double-brush copolymers and their performance as emulsion surfactants. Macromol. May 18, 2012;45(11):4623-9.
Luo et al., Toroidal structures from brush amphiphiles. Chem Commun. 2014;50(5):536-8.
Machida et al., Efficient approach to medium-sized cyclic molecules containing (E)-Alkene via z to e photochemical isomerization in the presence of AgNO3-impregnated silica gel. Chemistry Letters, 2018;47(2), 186-188. https://doi.org/10.1246/cl.170937.
Rangadurai et al., Temporal and triggered evolution of host-guest characteristics in amphiphilic polymer assemblies. J Am Chem Soc. Jun. 10, 2016;138(24):7508-11.
Rasmussen et al., Improved numerical algorithm for exploring block copolymer mesophases. J Polym Sci Part B: Poly Phys. Aug. 15, 2002;40(16):1777-83.
Runge et al., Synthesis and Self-Assembly of Bottlebrush Block Copolymers. PMSEPreprints, 2005;92:5-6.
Rzayev Synthesis of polystyrene-polylactide bottlebrush block copolymers and their melt self-assembly into large domain nanostructures. Macromol. Feb. 20, 2009;42(6):2135-41.
Sides et al., Parallel algorithm for numerical self-consistent field theory simulations of block copolymer structure. Polymer. Sep. 1, 2003;44(19):5859-66.
Sinturel et al., High χ-low N block polymers: how far can we go?. ACS Macro Lett. Sep. 2, 2015;4:1044-50.
Theodorakis et al., Interplay between chain collapse and microphase separation in bottle-brush polymers with two types of side chains. Macromol. May 4, 2010;43(11):5137-48.
Verduzco et al., Structure, function, self-assembly, and applications of bottlebrush copolymers. Chem. Soc. Rev., 2015;44:2405-20.
Wilkinson et al., Electrophilic fluorocyclization of allyl silanes. Angew Chem Int Ed Engl. 2009;48(38):7083-7086. doi:10.1002/anie.200901795.
Yi et al., Telmisartan attenuates hepatic fibrosis in bile ductligated rats. Acta Pharmacol Sin. Dec. 2012;33(12):1518-24. doi: 10.1038/aps.2012.115. Epub Oct. 29, 2012.
Yuan et al., One-pot syntheses of amphiphilic centipede-like brush copolymers via combination of ring-opening polymerization and "click" chemistry. Macromol. Jan. 27, 2010;43(4):1739-46.
Zhao et al., Polystyrene-Polylactide Bottlebrush Block Copolymer at the Air/Water Interface. Macromol. Sep. 28, 2009;42(22):9027-33.
Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.
Zheng et al., Morphology of ABC triblock copolymers. Macromol. Oct. 1995;28(21):7215-23.
Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.
*U.S. Appl. No. 16/887,427, filed May 29, 2020, Johnson et al.
*U.S. Appl. No. 16/898,331, filed Jun. 10, 2020, Johnson et al.
*U.S. Appl. No. 16/825,269, filed Mar. 20, 2020, Johnson et al.
PCT/US2017/064784, Jun. 20, 2019, International Preliminary Report on Patentability.
PCT/US2018/040488, Jan. 9, 2020, International Preliminary Report on Patentability.
PCT/US2018/040494, Jan. 9, 2020, International Preliminary Report on Patentability.
PCT/US2018/040496, Jan. 14, 2019, International Search Report and Written Opinion.
PCT/US2018/040496, Jan. 9, 2020, International Preliminary Report on Patentability.
PCT/US2014/33554, Aug. 29, 2014, International Search Report and Written Opinion.
International Search Report and Written Opinion dated Aug. 29, 2014 for Application No. PCT/US2014/33554.
Anderson, Late Transition Metal Complexes of Pentafluorophenylphosphino-Pincer Ligands. Doctoral Thesis. Victoria University of Wellington. 2012:ii, iii, 32.
Huynh, Novel Polymeric Micelles via RAFT Polymerization for Platinum Drug Delivery. Doctoral Thesis. The University of New South Wales. 2012:i, 57-58.
Johnson et al., Core-clickable PEG-branch-azide bivalent-bottlebrush polymers by ROMP: grafting-through and clicking-to. J Am Chem Soc. Jan. 26, 2011;133(3):559-66. doi: 10.1021/ja108441d. Epub Dec. 13, 2010.
Johnson et al., Drug-loaded, bivalent-bottle-brush polymers by graft-through ROMP. Macromolecules. Dec. 28, 2010;43(24):10326-10335.
Johnson et al., Efficient Synthesis of Doxorubicin Releasing Brush Polymers by Graft-Through Romp. Polymer Preprints. 2010;51(2):96-97.
Li et al., Surface Properties of Bottlebrush Polymer Thin Films. Macromolecules. 2012;45(17):7118-7127.
Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.
International Preliminary Report on Patentability for PCT/US2014/033554, dated Oct. 22, 2015.
Extended European Search Report for EP 14782253.0, dated Nov. 11, 2016.
International Search Report and Written Opinion for PCT/US2017/036447, dated Sep. 7, 2017.
International Preliminary Report on Patentability for PCT/US2017/036447, dated Dec. 20, 2018.
International Search Report and Written Opinion for PCT/US2017/064784, dated Mar. 1, 2018.
International Search Report and Written Opinion for PCT/US2018/040488, dated Oct. 15, 2018.
International Search Report and Written Opinion for PCT/US2018/040494, dated Oct. 10, 2018.
Invitation to Pay Additional Fees for PCT/US2018/040496, dated Nov. 21, 2018.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.

(56) References Cited

OTHER PUBLICATIONS

Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. EpubSep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996;120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR to Compare PEG-branch-nitroxide "Bivalent-Brush Polymers" and Traditional PEG Bottle-Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.
Campos-Fernandez et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.
Campos-Fernandez et al., Fine-tuning the ring-size of metal-lacyclophanes: a rational approach to molecular pentagons. J Am Chem Soc. Jan. 31, 2001;123(4):773-4.
Caravan et al., Gadolinium(III) Chelates as MRI Contrast Agents: Structure, Dynamics, and Applications. Chem Rev. Sep. 8, 1999;99(9):2293-352.
Castilla et al., Stereochemistry in subcomponent self-assembly. Acc Chem Res. Jul. 15, 2014;47(7):2063-73. doi: 10.1021/ar5000924. Epub May 2, 2014.
Chambron et al., Topologically complex molecules obtained by transition metal temptation: it is the presentation that determines the synthesis strategy. New Journal of Chemistry. 2013;37(1):49-57.
Chand et al., Self-assembly of a novel macrotricyclic Pd(II) metal-locage encapsulating a nitrate ion. Chem Commun (Camb). Sep. 7, 2001 ;(17):1652-3.
Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.
Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

(56) References Cited

OTHER PUBLICATIONS

Chen et al., Synthesis of superporous hydrogels: hydrogels with fast swelling and superabsorbent properties. J Biomed Mater Res. Jan. 1999;44(1):53-62.
Cheon et al., Synergistically integrated nanoparticles as multimodal probes for nanobiotechnology.Acc Chem Res. Dec. 2008;41(12):1630-40. doi: 10.1021/ar800045c.
Chifotides et al., Anion-.pi. interactions in supramolecular architectures. Acc Chem Res. Apr. 16, 2013;46(4):894-906. doi: 10.1021/ar300251k. Epub Mar. 11, 2013.
Choi et al., Self-confirming "AND" logic nanoparticles for fault-free MRI. J Am Chem Soc. Aug. 18, 2010;132(32):11015-7. doi: 10.1021/ja104503g.
Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.
Clever et al., Inclusion of anionic guests inside a molecular cage with palladium(II) centers as electrostatic anchors. Angew Chem Int Ed Engl. 2009;48(38):7010-2. doi: 10.1002/anie.200902717.
Cok et al., Synthesis of Model Network Hydrogels via Tetrazine-Olefin Inverse Electron Demand Diels-Alder Cycloaddition. Macromolecular Symposia. Jul. 2013;329(1):108-112.
Conrad et al., Tunable, temperature-responsive polynorbornenes with side chains based on an elastin peptide sequence. Angew Chem Int Ed Engl. 2009;48(44):8328-30. doi: 10.1002/anie.200903888.
Cordier et al., Self-healing and thermoreversible rubber from supramolecular assembly. Nature. Feb. 21, 2008;451(7181):977-80. doi: 10.1038/nature06669.
Dag et al., Three-arm star ring opening metathesis polymers via alkyne-azide click reaction. J. Polym. Sci. A Polym. Chem., 47: 2344-2351. doi:10.1002/pola.23324.
Davies et al., Environmentally responsive MRI contrast agents. Chem Commun (Camb). Oct. 28, 2013;49(84):9704-21. doi: 10.1039/c3cc44268c.
Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.
Davis et al., Nanoparticle therapeutics: an emerging treatment modality for cancer. Nat Rev Drug Discov. Sep. 2008;7(9):771-82. doi: 10.1038/nrd2614.
Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.
Detape et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.
Duncan et al., The dawning era of polymer therapeutics. Nat Rev Drug Discov. May 2003;2(5):347-60.
Duncan, The dawning era of polymer therapeutics. Nat Rev Drug Discov. May 2003;2(5):347-60.
Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.
Eryazici et al., Two Large-Pore Metal-Organic Frameworks Derived from a Single Polytopic Strut. Crystal Growth & Design. Mar. 7, 2012;12(3):1075-1080.
Feng et al., A metabonomic analysis of organ specific response to USPIO administration. Biomaterials. Sep. 2011;32(27):6558-69. doi: 10.1016/j.biomaterials.2011.05.035.
Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.
Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.
Forgan et al., Chemical topology: complex molecular knots, links, and entanglements. Chem Rev. Sep. 14, 2014;111(9):5434-64. doi: 10.1021/cr200034u. Epub Jun. 21, 2011.
Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.
Fox et al., Soluble polymer carriers for the treatment of cancer: the importance of molecular architecture. Acc Chem Res. Aug. 18, 2009;42(8):1141-51. doi: 10.1021/ar900035f.
Fullenkamp et al., Mussel-Inspired Histidine-Based Transient Network Metal Coordination Hydrogels. Macromolecules. Jan. 18, 2013;46(3):1167-1174.
Gao et al., Development of star polymers as unimolecular containers for nanomaterials. Macromol Rapid Commun. May 14, 2012;33(9):722-34. doi: 10.1002/marc.201200005. Epub Mar. 14, 2012.
Gao et al., Modular Approaches to Star and Miktoarm Star Polymers by ATRP of Cross-Linkers. Macromol. Symp., 291-292: 12-16. doi:10.1002/masy.201050502.
Gao et al., Synthesis of Acid-Labile PEG and PEG-Doxorubicin-Conjugate Nanoparticles via Brush-First ROMP. ACS Macro Lett., 2014;3(9):854-857. DOI: 10.1021/mz5004097.
Gao et al., Synthesis of functional polymers with controlled architecture by CRP of monomers in the presence of cross-linkers: From stars to gels. Progress in Polymer Science Apr. 2009;34(4):317-350.
Gao et al., Synthesis of Star Polymers by A New "Core-First" Method: Sequential Polymerization of Cross-Linker and Monomer. Macromolecules, 2008;41(4):1118-1125. DOI: 10.1021/ma702560f.
Ge et al., A Pyrene-functionalized Polynorbornene for Ratiometric Fluorescence Sensing of Pyrophosphate. Chem. Asian J. 2016;11:687.
Gilgorich et al., Palladium-catalyzed reductive coupling of styrenes and organostannanes under aerobic conditions. J Am Chem Soc. Nov. 21, 2007;129(46):14193-5. Epub Oct. 27, 2007.
Glunde et al., Magnetic resonance spectroscopy in metabolic and molecular imaging and diagnosis of cancer. Chem Rev. May 12, 2010;110(5):3043-59. doi: 10.1021/cr9004007.
Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.
Greenwald et al., Effective drug delivery by PEGylated drug conjugates. Adv Drug Deliv Rev. Feb. 10, 2003;55(2):217-50.
Grumbley et al., Photoresponsive Polymers Containing Nitrobenzyl Esters via Ring-Opening Metathesis Polymerization. Macromolecules. 2011;44(20):7956-61.
Hackelbusch et al., Chain Dynamics in Supramolecular Polymer Networks. Macromolecules. 2013;46(15):6273-6286.
Hackelbusch et al., Multiresponsive Polymer Hydrogels by Orthogonal Supramolecular Chain Cross-Linking. Macromolecules. 2014;47(12):4028-4036.
Haddleton et al., Well-defined oligosaccharide-terminated polymers from living radical polymerization. Biomacromolecules. 2000 Summer;1(2):152-6.
Hafkamp et al., Organogel formation and molecular imprinting by functionalized gluconamides and their metal complexes. Chemical Communications. 1997;6:545-546. doi: 10.1039/A608266A.

(56) References Cited

OTHER PUBLICATIONS

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011 ;133(35):13828-31. doi: 10.1021/ja203957h. Epub Aug. 11, 2011.

Hao et al., Dendrimers as scaffolds for multifunctional reversible addition-fragmentation chain transfer agents: Syntheses and polymerization. J. Polym. Sci. A Polym. Chem., 2004;42:5877-5890. doi:10.1002/pola.20434.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi:10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jamieson et al., Structure, Recognition, and Processing of Cisplatin-DNA Adducts. Chem Rev. Sep. 8, 1999;99(9):2467-98.

Jesberger et al., Hyperbranched polymers as scaffolds for multifunctional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi200-40219_113203.pdf Retrieved Apr. 24, 2015. cited byapplicant.

Kirchhoff et al., Boronic acids: new coupling partners in room-temperature Suzuki reactions of alkyl bromides. Crystallographic

(56) References Cited

OTHER PUBLICATIONS characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel. 2013.03.016. Epub Mar. 29, 2013.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci. 2009.11.002.

Leininger et al., Self-assembly of discrete cyclic nanostructures mediated by transition metals. Chem Rev. Mar. 8, 2000;100(3):853-908.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n. cited byapplicant.

Li et al., Polycatechol Nanoparticle MRI Contrast Agents. Small, 2016;12(5):668-677. https://doi.org/10.1002/smll.201502754.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Liao et al., A Convergent Synthetic Platform for Single-Nanoparticle Combination Cancer Therapy: Ratiometric Loading and Controlled Release of Cisplatin, Doxorubicin, and Camptothecin. J. Am. Chem. Soc., 2014;136(16):5896-5899. DOI: 10.1021/ja502011g.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011. cited byapplicant.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t. cited byapplicant.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm. 2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc. 201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805. doi: 10.1021/acsnano.6b07196.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

(56) References Cited

OTHER PUBLICATIONS

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

Mckenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

Mckenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., Oximes as reversible links in polymer chemistry: dynamic macromolecular stars. Polym. Chem., 2014;5:6923-6931. DOI: 10.1039/C4PY01282H.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nair et al., Modulating mechanical properties of self-assembled polymer networks by mult-ifunctional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Paletta et al., Synthesis and Reduction Kinetics of Sterically Shielded Pyrrolidine Nitroxides. Org. Lett., 2012;14(20):5322-5325. DOI: 10.1021/o1302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) inpatients with solid tumours. Br J Cancer. Feb. 15, 2011;104(4):593-8. doi: 10.1038/bjc.2011.6. Epub Feb. 1, 2011.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

(56) References Cited

OTHER PUBLICATIONS

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Rzayev et al., Molecular Bottlebrushes: New Opportunities in Nanomaterials Fabrication. ACS Macro Lett., 2012;1(9):1146-1149. DOI: 10.1021/mz300402x.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Skomski et al., Redox-active on-surface assembly of metal-organic chains with single-site Pt(II). *J Am Chem Soc. Jul. 16, 2014;136(28):9862-5. doi: 10.1021/ja504850f. Epub Jul. 1, 2014.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications2014;5:Article No. 5460.

Spiniello et al., Synthesis and characterization of fluorescently labeled core cross-linked star polymers. J. Polym. Sci. A Polym. Chem., 2008;46:2422-2432. doi: 10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Coordination-directed assembly of trigonal and tetragonal molecular boxes encapsulating anionic guests. Journal of the Chemical Society, Dalton Transactions. 2001:359-361. doi: 10.1039/B0101180.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Thompson et al., Labelling polymers and micellar nanoparticles via initiation, propagation and termination with ROMP. Polym. Chem., 2014;5:1954-1964.

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

Tolmasoff et al., Superoxide dismutase: correlation with life-span and specific metabolic rate in primate species. Proc Natl Acad Sci U S A. May 1980;77(5):2777-81.

Tominaga et al., Finite, spherical coordination networks that self-organize from 36 small components. Angew Chem Int Ed Engl. Oct. 25, 2004;43(42):5621-5.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.

Valeur et al., Amide bond formation: beyond the myth of coupling reagents. Chem. Soc. Rev., 2009;38:606-631. DOI: 10.1039/B701677H.

Verduzco et al., Correction: Structure, function, self-assembly, and applications of bottlebrush copolymers. Chem Soc Rev. Nov. 7, 2015;44(21):7916. doi: 10.1039/c5cs90099a.

Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.

(56) References Cited

OTHER PUBLICATIONS

Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.

Wang et al., Advances of cancer therapy by nanotechnology. Cancer Res Treat. Mar. 2009;41(1):1-11. doi: 10.4143/crt.2009.41.1.1. Epub Mar. 31, 2009.

Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].

Wei et al., Exceedingly small iron oxide nanoparticles as positive MRI contrast agents. Proc. Natl. Acad. Sci. USA 2017;114(9):2325-2330.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Wong et al., Quantitative formation of core cross-linked star polymers via a one-pot two-step single electron transfer-living radical polymerization. Polym. Chem., 2013;4:4562-4565. DOI: 10.1039/C3PY00726J.

Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.

Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.

Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. EpubAug. 28, 2012.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

Xu et al., Scaling Laws in Supramolecular Polymer Networks. Macromolecules. 2011;44(13):5465-5472.

Xu et al., Strain Hardening and Strain Softening of Reversibly Cross-linked Supramoleeecular Polymer Networks. Macromolecules. Sep. 27, 2011;44(18):7478-7488.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. EpubAug. 8, 2013.

Yan et al., Particle carriers for combating multidrug-resistant cancer. ACS Nano. Nov. 26, 2013;7(11):9512-7. doi: 10.1021/nn405632s. Epub Nov. 11, 2013.

Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014. cited byapplicant.

Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.

Yang et al., Luminescent chemodosimeters for bioimaging. Chem Rev. Jan. 9, 2013;113(1):192-270. doi: 10.1021/cr2004103. Epub Jun. 18, 2012.

Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.

Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.

Yoshizawa et al., Molecular architectures of multi-anthracene assemblies. Chem Soc Rev. Mar. 21, 2014;43(6):1885-98. doi: 10.1039/c3cs60315f.

You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.

Yount et al., Small-molecule dynamics and mechanisms underlying the macroscopic mechanical properties of coordinatively cross-linked polymer networks. J Am Chem Soc. Oct. 19, 2005;127(41):14488-96.

Yount et al., Strong means slow: dynamic contributions to the bulk mechanical properties of supramolecular networks. Angew Chem Int Ed Engl. Apr. 29, 2005;44(18):2746-8.

Yue et al., Macrocyclic and lantern complexes of palladium(II) with bis(amidopyridine) ligands: synthesis, structure, and host-guest chemistry. Inorg Chem. Nov. 29, 2004;43(24):7671-81.

Zhang et al., Active cross-linkers that lead to active gels. Angew Chem Int Ed Engl. Oct. 25, 2013;52(44):11494-8. doi: 10.1002/anie.201304437. Epub Sep. 12, 2013.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.

Zhang et al., Redox-Responsive, Core Cross-Linked Polyester Micelles. ACS Macro Lett., 2013;2(1):40 44. DOI: 10.1021/mz300522n.

Zhao et al., Rheological Behavor of Shear-Responsive Metallo-Supramolecular Gels. Macromolecules. 2004;37(10):3529-3531.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

(56) References Cited

OTHER PUBLICATIONS

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.
Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
International Search Report and Written Opinion for PCT/US2019/046872, dated Oct. 29, 2019.
International Search Report and Written Opinion for PCT/US2020/023836, dated Jul. 7, 2020.
Aguirre-Chagala et al., Phenylboronic Acid-Installed Polycarbonates for the ph-Dependent Release of Diol-Containing Molecules. ACS Macro Letters. Nov. 20, 2014;3(12):1249-1253.
Ma et al., Hierarchical Responsive Nanoplatform with Two-Photon Aggregation-Induced Emission Imaging for Efficient Cancer Theranostics. ACS Appl Mater Interfaces. Dec. 18, 2019;11(50):47259-47269. doi: 10.1021/acsami.9b17587. Epub Dec. 9, 2019. PMID: 31769279.
Qiu et al., Oxidation-Responsive Polymer-Drug Conjugates with a Phenylboronic Ester Linker. Macromol Rapid Commun. Nov. 2015;36(22):2012-8. doi: 10.1002/marc.201500349. Epub Aug. 22, 2015. PMID: 26297612.
Su et al., Catechol polymers for pH-responsive, targeted drug delivery to cancer cells. J Am Chem Soc. Aug. 10, 2011;133(31):11850-3. doi: 10.1021/ja203077x. Epub Jul. 19, 2011. PMID: 21751810; PMCID: PMC3149454.
Tanino et al., Control of Stereochemistry by sigma-Participation of a Silyl Group. A Novel Method for Diastereoselective Polyol Synthesis. J Org Chem. Jun. 27, 1997;62(13):4206-4207. doi: 10.1021/jo9703515. PMID: 11671736.
International Search Report and Written Opinion for PCT/US2020/055862 dated May 6, 2021.
Invitation to Pay Additional Fees for PCT/US2020/055862, dated Feb. 12, 2021.
International Search Report and Written Opinion for PCT/US2019/027414, dated Sep. 12, 2019.
International Preliminary Report on Patentability for PCT/US2019/027414, dated Oct. 22, 2020.
International Preliminary Report on Patentability for PCT/US2020/023836, dated Dec. 2, 2021.
Alvaradejo et al., Polyoxazoline-Based Bottlebrush and Brush-Arm Star Polymers via ROMP: Syntheses and Applications as Organic Radical Contrast Agents. ACS Macro Lett. Apr. 16, 2019;8(4):473-478. doi: 10.1021/acsmacrolett.9b00016. Epub Apr. 4, 2019. PMID: 31289694; PMCID: PMC6615754.
Nguyen et al., Pro-organic radical contrast agents ("pro-ORCAs") for real-time MRI of pro-drug activation in biological systems. Polym Chem. Aug. 7, 2020;11(29):4768-4779. doi: 10.1039/d0py00558d. Epub Jun. 26, 2020. PMID: 33790990; PMCID: PMC8009311.
Nguyen et al., Triply Loaded Nitroxide Brush-Arm Star Polymers Enable Metal-Free Millimetric Tumor Detection by Magnetic Resonance Imaging. ACS Nano. Nov. 27, 2018;12(11):11343-11354. doi: 10.1021/acsnano.8b06160. Epub Nov. 2, 2018. PMID: 30387988; PMCID: PMC6320246.
Ohwada et al., Design, synthesis and antifungal activity of a novel water soluble prodrug of antifungal triazole. Bioorg Med Chem Lett. Jan. 20, 2003;13(2):191-6. doi: 10.1016/s0960-894x(02)00892-2. PMID: 12482421.

International Search Report and Written Opinion for PCT/US2017/055145, dated Jan. 23, 2018.
International Preliminary Report on Patentability for PCT/US2017/055145, dated Apr. 18, 2019.
International Search Report and Written Opinion for PCT/US2017/48641, dated Nov. 9, 2017.
International Preliminary Report on Patentability for PCT/US2017/48641 dated Mar. 7, 2019.
Invitation to Pay Additional Fees for PCT/US2020/059827 dated Feb. 4, 2021.
International Search Report and Written Opinion for PCT/US2020/059827 dated Mar. 15, 2021.
International Preliminary Report on Patentability for PCT/US2020/059827 dated Jul. 21, 2022.
International Preliminary Report on Patentability for PCT/US2020/055862 dated Apr. 28, 2022.
International Search Report and Written Opinion for PCT/US2022/047333 dated Jan. 25, 2023.
[No Author Listed], 2-Propen-l-amine, 3-(2-methoxyphenyl)-N-2-propyn-l-yl. CAS Registry File RN 1883141-01-2. STN Entry Date Mar. 10, 2016.
Blencowe et al., Ring-opening metathesis polymerization with the second generation Hoveyda-Grubbs catalyst: an efficient approach toward high-purity functionalized macrocyclic oligo(cyclooctene)s. J Am Chem Soc. Apr. 17, 2013;135(15):5717-25. doi: 10.1021/ja312418z. Epub Apr. 8, 2013.
Borke et al., Poly(glyceryl glycerol): A multi-functional hydrophilic polymer for labeling with boronic acids. Polym Chem. Jun. 1, 2017;55(11):1822-30. doi: 10.1002/pola.28497.
Cannon, J.G., Analog Design. In: Burger's Medicinal Chemistry and Drug Discovery, Fifth Edition, vol. I: Principles and Practice. 1995. Burger, Ed. Wiley Interscience. Chapter 19:783-802.
Clark et al., Dynamically Restructuring Hydrogel Networks Formed with Reversible Covalent Crosslinks. Advanced Materials. 2007;19:2503-2507. 10.1002/adma.200602649.
Collins et al., Chemical approaches to targeted protein degradation through modulation of the ubiquitin-proteasome pathway. Biochem J. Mar. 15, 2017;474(7):1127-1147. doi: 10.1042/BCJ20160762.
Fiers et al., Orthogonal Synthesis of Xeno Nucleic Acids. Chemistry. Dec. 12, 2016;22(50):17945-17948. doi: 10.1002/chem.201604386. Epub Nov. 3, 2016.
Fu et al., Relay Conjugation of Living Metathesis Polymers. J Am Chem Soc. Sep. 26, 2018;140(38):12181-12188. doi: 10.1021/jacs.8b07315. Epub Sep. 11, 2018.
Kumar et al., Multivalency in the recognition and antagonism of a HIV TAR RNA-TAT assembly using an aminoglycoside benzimidazole scaffold. Org Biomol Chem. Feb. 14, 2016;14(6):2052-6. doi: 10.1039/c5ob02016f.
Manyeruke et al., Synthesis and evaluation of 3-hydroxy-3-phenylpropanoate ester-AZT conjugates as potential dual-action HIV-1 Integrase and Reverse Transcriptase inhibitors. Bioorg Med Chem. Dec. 15, 2015;23(24):7521-8. doi: 10.1016/j.bmc.2015.10.039.
Nguyen et al., Scalable Synthesis of Multivalent Macromonomers for ROMP. ACS Macro Lett. Apr. 17, 2018;7(4):472-476. doi: 10.1021/acsmacrolett.8b00201. Epub Mar. 26, 2018.
Nishimura et al., Rhodium-Catalyzed Asymmetric Cycloisomerization of 1,6-Ene-ynamides. Adv Synth Catal. May 3, 2013;355(7):1374-82. doi: 10.1002/adsc.201300148.
Pesek et al., Synthesis of bottlebrush copolymers based on poly (dimethylsiloxane) for surface active additives. Polymer. Aug. 19, 2016;98(19):495-504.
Smith et al., Modular synthesis of biologically active phosphatidic acid probes using click chemistry. Mol Biosyst. Sep. 2009;5(9):962-72. doi: 10.1039/b901420a. Epub May 7, 2009.
Tinworth et al., Small molecule-mediated protein knockdown as a new approach to drug discovery. Med Chem Commun. Jul. 26, 2016;7:2206-16. doi: 10.1039/C6MD00347H.
Venkatesh et al., Role of the development scientist in compound lead selection and optimization. J Pharm Sci. Feb. 2000;89(2):145-54. doi: 10.1002/(SICI)1520-6017(200002)89:2<145::AID-JPS2>3.0.CO;2-6.

(56) References Cited

OTHER PUBLICATIONS

Wurz et al., A "Click Chemistry Platform" for the Rapid Synthesis of Bispecific Molecules for Inducing Protein Degradation. J Med Chem. Jan. 25, 2018;61(2):453-461. doi: 10.1021/acs.jmedchem. 6b01781. Epub Apr. 17, 2017.

Yan et al., The relationship among pKa, pH, and binding constants in the interactions between boronic acids and diols—it is not as simple as it appears. Tetrahedron. Nov. 29, 2004;60(49):11205-11209.

Zhang et al., Convergent Synthesis of Branched Metathesis Polymers with Enyne Reagents. Macromolecules. Sep. 28, 2021;54(18):8435-8442. doi: 10.1021/acs.macromol.1c01051. Epub Sep. 8, 2021.

\* cited by examiner

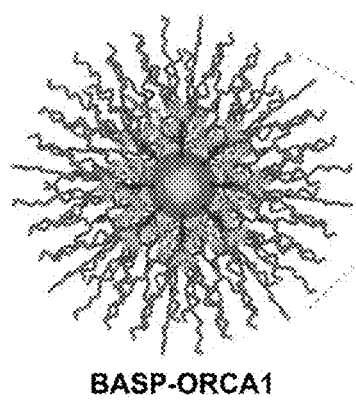
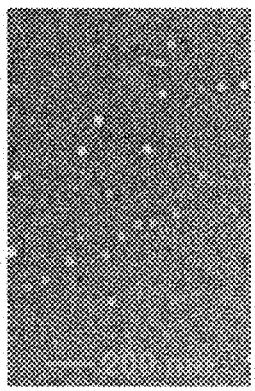
BASP-ORCA1
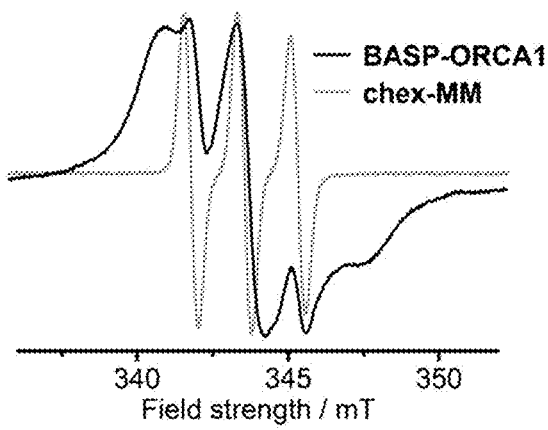
Figure 2A
Figure 2B
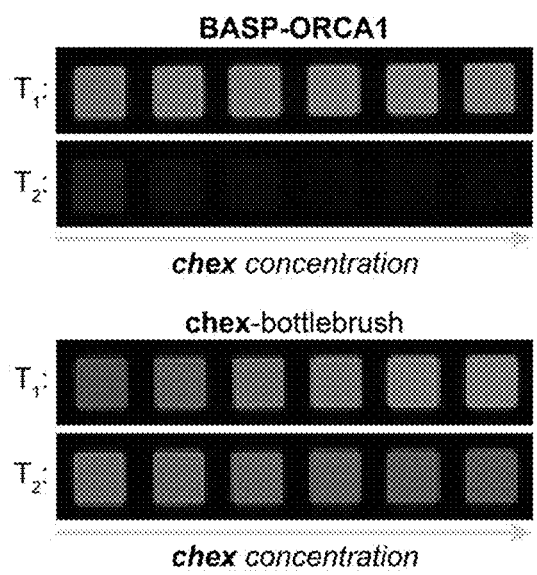
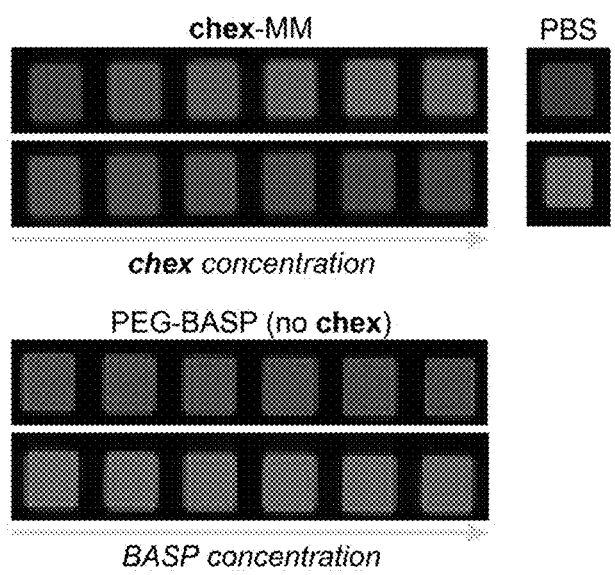
Figure 2C

| name | composition | | diameter | | relaxivity | | notes |
|---|---|---|---|---|---|---|---|
| | $m$ | $N$ | $D_h$ / nm | $D_{TEM}$ / nm | $r_1$ / $M^{-1}s^{-1}$ | $r_2$ / $M^{-1}s^{-1}$ | |
| 3-CP | - | - | - | - | 0.15 | 0.17 | |
| chex-MM | - | - | - | - | 0.21 | 0.30 | |
| chex-dendrimer | - | - | - | - | 0.44 | 0.86 | |
| chex-bottlebrush | 55.55 | - | 17 | n.d. | 0.32 | 0.82 | |
| BASP-ORCA | 5.05 | 20 | 31 ± 2 | n.d. | 0.27 | 6.92 | poor solubility (<10 mg / mL) |
| BASP-ORCA | 5.05 | 30 | 49 ± 6 | n.d. | 0.53 | 7.11 | poor solubility (<10 mg / mL) |
| BASP-ORCA1 | 7.07 | 20 | 31 ± 4 | 37 ± 7 | 0.41 | 4.67 | good solubility (>50 mg / mL) |
| BASP-ORCA | 7.07 | 30 | 36 ± 3 | n.d. | 0.35 | 7.40 | poor solubility (<10 mg / mL) |
| BASP-ORCA | 9.99 | 15 | 28 ± 3 | 38 ± 10 | 0.33 | 2.90 | low relaxivity |
| BASP-ORCA | 9.99 | 30 | 33 ± 4 | 39 ± 10 | 0.37 | 4.52 | low relaxivity |

Figure 15

BRUSH-ARM STAR POLYMER IMAGING AGENTS AND USES THEREOF

RELATED APPLICATIONS

This application claims priority under 35 U.S.C. § 119(e) to U.S. Provisional Application, U.S. Ser. No. 62/528,026, filed Jun. 30, 2017, which is incorporated herein by reference.

GOVERNMENT SUPPORT

This invention was made with government support under grant numbers EB018529 and EB019950 awarded by the National Institutes of Health. The government has certain rights in the invention.

BACKGROUND OF THE INVENTION

Among the many imaging modalities for medical diagnostics, magnetic resonance imaging (MRI) is one of the most useful due to its ability to non-invasively generate three-dimensional detailed anatomical images with high spatial resolution while not requiring an ionizing source and remaining insensitive to depth.[1,2,3,4] Current clinical MRI methods depict the spatial distribution and chemical environment of water protons ($^1H$) within a region of interest (ROI) with the use of contrast agents. These contrast agents are divided into two primary classes: $T_1$ contrast agents (e.g., paramagnetic metals such as gadolinium or manganese) that afford positive-contrast images primarily by locally reducing the protons' longitudinal relaxation time (spin-lattice, $T_1$), and $T_2$ contrast agents (e.g., superparamagnetic iron oxide nanoparticles) that afford negative-contrast images by locally reducing the transverse relaxation time (spin-spin, $T_2$) of water molecules.[5,6] The corresponding $^1H$ water relaxivities ($r_1$ and $r_2$, respectively) of a contrast agent characterize the extent to which the agent decreases the $T_1$ and $T_2$ times of water. Contrast agents with greater $r_1$ and $r_2$ values provide increased image contrast compared to those with lower values at the same concentration.[6,7]

Most MRI contrast agents with large $r_1$ and/or $r_2$ values contain metals that feature a large number of unpaired electrons. For example, small molecule[8,9,10,11,12,13] and nanoparticle-based[14,15,16,17,18,19,20,21] contrast agents featuring Gd, Mn, Fe-oxide, and other metals have been reported to function as either $T_1$ or $T_2$ contrast agents or both. Furthermore, metal-based contrast agents that display advanced functions such as multimodal imaging,[8,9,10,12,13,17,20,21] enhanced target-specific accumulation,[14,18,19] or sensing[8,1,12,13,14] have all been developed. Metal-based contrast agents, especially nanoparticle systems which tend to accumulate in biological tissues, suffer from a few key limitations. Most notably, they could present toxicity concerns in patients with hindered kidney function and newborn children; additionally, Gd-based agents, perhaps the most widely used contrast agents in the clinic, have recently been linked to a rising prevalence of toxic Gd ions in the environment[5,22,23,24,25,26,27,28,29,30] Thus, there is interest in developing "metal-free" MRI contrast agents that make use of organic components. Such agents could enable MRI in at-risk patient populations, and they could potentially open new avenues for functional/responsive MRI based on in vivo organic transformations that require longer timeframes and contrast agents with low toxicity. For example, organic nanoparticles could have advantages for imaging strategies that require long-term tissue accumulation, such as tumor imaging.

SUMMARY OF THE INVENTION

Four main classes of metal-free MRI contrast agents have been most widely studied: paramagnetic nitroxide-based Organic Radical Contrast Agents (ORCAs), hyperpolarized $^{13}C$ agents, $^{19}F$ MRI contrast agents, and chemical exchange saturation transfer (CEST) contrast agents. While $^{19}F$ MRI and CEST agents have undergone many advances in recent years,[31,32,33,34,35,36,37,38] these approaches often suffer from low sensitivity, and in some cases, require a high contrast agent concentration (10-50 mM), long imaging times, and/or potentially harmful high-intensity radio-frequency fields. Hyperpolarized $^{13}C$ agents, on the other hand, can theoretically afford up to $10^5$ sensitivity improvements; nevertheless, issues including short hyperpolarization lifetimes that lead to limited imaging times and complexity in terms of the chemistry and instrumentation required for generation of the hyperpolarized agent remain major challenges.[39,40,41] Furthermore, neither $^{19}F$ MRI, CEST, nor hyperpolarized $^{13}C$ agents have become common in the clinic, which could prevent their rapid adoption.[39,40,41,42,43,44,45,46] In contrast, nitroxide ORCAs rely on standard water relaxation mechanisms to achieve MRI contrast, and therefore, could be immediately translated to clinical applications. However, several key challenges limit the clinical feasibility of nitroxide ORCAs. First, the nitroxide radical only possesses one unpaired electron. As a result, compared to metal-based contrast agents such as $Gd^{3+}$ (7 unpaired electrons) or $Mn^{2+}$ (5 unpaired electrons), nitroxide ORCAs inherently suffer from much lower $^1H$ water relaxivity. One strategy to overcome this limitation is to use a poly(nitroxide) macromolecule where the relatively low per nitroxide relaxivity is multiplied by the number of nitroxide moieties bound to the macromolecule to achieve higher relaxivity. The second major limitation of nitroxide ORCAs is the fact that they are typically reduced rapidly in vivo to diamagnetic hydroxylamines, thus rendering them ineffective as contrast agents shortly after injection.[47,48,49,50] Indeed, initial efforts to utilize nitroxides as MRI contrast agents exposed these shortcomings,[51,52] and though their rapid bioreduction has been cleverly exploited to enable redox-mapping in vitro and in vivo,[53,54,55,56,57] an in vivo-stable nitroxide ORCA that allows for longitudinal studies over clinically meaningful timescales following systemic administration has yet to be developed.

Nanoparticle-based nitroxide ORCAs with long-term in vivo stability could be particularly useful for tumor imaging; nanoparticles of suitable size (~10-200 nm) are known to passively accumulate in tumors via the enhanced permeation and retention effect, especially in common murine (e.g. mouse) models, but hours to tens of hours are often needed to reach maximal accumulation[58,59,60,61,62,63,64] As stated above, there are no nitroxide-based molecules or materials with demonstrated capability to provide in vivo MRI contrast after such long times. This problem is exacerbated in murine models where imaging is often used for preclinical studies of disease development; murine tissues contain higher levels of metabolic antioxidants, which lead to faster nitroxide reduction rates.[65,66] Thus, the development of stable nitroxide-based ORCAs with high relaxivities would open a new class of imaging applications whereby the accumulation of contrast agents in tissues could enable MRI without toxicity concerns.[50,67,68] Moreover, the flexibility of nanoparticle-based materials could facilitate future image-guided drug delivery strategies.

Compositions, methods, systems, and kits that allow for the preparation and use of a new class of Brush-Arm Star Polymer ORCAs (BASP-ORCAs) are disclosed herein. In addition, in vitro and in vivo experiments utilizing BASP-ORCAs are described along with compositions, methods, systems, and uses thereof. BASP-ORCAs are designed to overcome the aforementioned challenges associated with MRI using typical contrast agents.

In certain embodiments, the present disclosure provides a brush-star arm polymer with an associated imaging agent (e.g., a nitroxide-based contrast agent). Such a polymer may be in the form of a particle, such as a nanoparticle. In certain embodiments, the present disclosure provides a brush-arm star polymer with an imaging agent comprising at least 100 repeating units selected from Formula (I) and Formula (II):

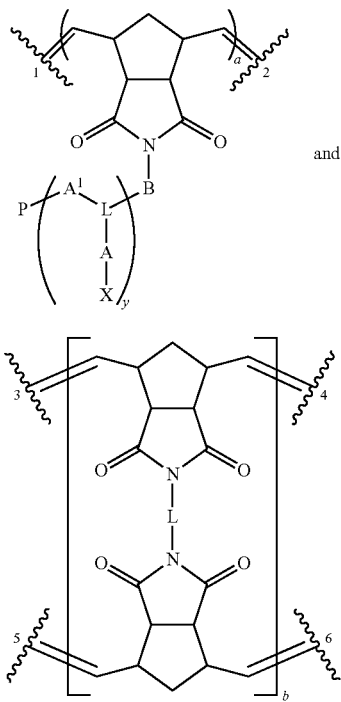

Formula (I)

and

Formula (II)

and salts thereof, wherein:

each of A, $A^1$, and B is independently $C_1$-$C_{12}$ alkylene, $C_2$-$C_{12}$ alkenylene, $C_2$-$C_{12}$ alkynylene, or $C_1$-$C_{12}$ heteroalkylene, $C_2$-$C_{12}$ heteroalkenylene, $C_2$-$C_{12}$ heteroalkynylene, wherein each alkylene, alkenylene, alkynylene, heteroalkylene, heteroalkenylene, or heteroalkynylene is optionally substituted with 1-24 independently selected $R^1$;

X is an imaging agent as described herein;

P is alkylene, heteroalkylene, or polymer;

L is a bond, —O—, —S—, —S—S—, $C_1$-$C_{12}$ alkylene, $C_2$-$C_{12}$ alkenylene, $C_2$-$C_{12}$ alkynylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), ($C_0$-$C_{12}$ alkylene)-heterocyclylene-($C_0$-$C_{12}$ alkylene), ($C_0$-$C_{12}$ heteroalkylene)-heterocyclylene-($C_0$-$C_{12}$ alkylene), ($C_0$-$C_{12}$ heteroalkylene)-aryl-($C_0$-$C_{12}$ heteroalkylene), or ($C_0$-$C_{12}$ heteroalkylene)-heterocyclylene-($C_0$-$C_{12}$ heteroalkylene), wherein each alkylene, alkenylene, alkynylene, heteroalkylene, arylene, heteroarylene, or heterocyclylene is optionally substituted with 1-24 independently selected $R^1$, and combinations thereof;

each $R^1$ is independently alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$;

each $R^A$ is independently hydrogen, $C_1$-$C_6$ alkyl, $C_1$-$C_6$ heteroalkyl, or $C_1$-$C_6$ haloalkyl; each of a and b are independently an integer between 1 and 10000, inclusive;

each of "1", "2", "3", "4", "5", and "6" is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thiol; or represents a bond to a another repeating unit of Formula (I) or Formula (II);

y is an integer between 1 and 100, inclusive; and m is 1 or 2.

In certain embodiments, the imaging agent is a chelated metal, inorganic compound, organometallic compound, organic compound, or salt thereof. In certain embodiments, the imaging agent is an organic compound. In certain embodiments, the imaging agent is an organic radical. In certain embodiments, the imaging agent is a nitroxide-containing imaging agent. In certain embodiments, the imaging agent is

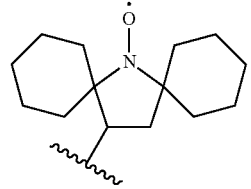

In certain embodiments, the imaging agent is useful for performing magnetic resonance imaging.

In certain embodiments, the imaging agent is a salt of an organic compound. In certain embodiments, the imaging agent

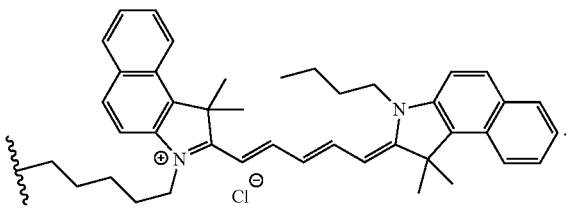 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-]]

In certain embodiments, the imaging agent is useful for performing near-infrared fluorescence imaging.

In certain embodiments, the present disclosure provides methods to produce a brush-arm star polymer comprising reacting one or more macromonomers associated with an imaging agent with a metathesis catalyst to form a living polymer; and mixing a crosslinker with the living polymer. In certain embodiments, at least two different macromonomers each containing a different imaging agents are reacted together to form the brush-arm star polymer.

In certain embodiments, the macromonomer is of Formula (III):

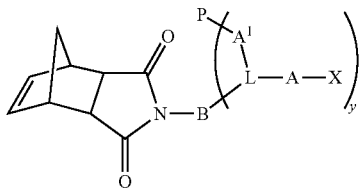

Formula (III)

or a salt thereof, wherein:
- each of A, $A^1$, and B is independently $C_1$-$C_{12}$ alkylene, $C_2$-$C_{12}$ alkenylene, $C_2$-$C_{12}$ alkynylene, or $C_1$-$C_{12}$ heteroalkylene, $C_2$-$C_{12}$ heteroalkenylene, $C_2$-$C_{12}$ heteroalkynylene, wherein each alkylene, alkenylene, alkynylene, heteroalkylene, heteroalkenylene, or heteroalkynylene is optionally substituted with 1-24 independently selected $R^1$;
- X is an imaging agent described herein;
- P is alkylene, heteroalkylene, or polymer;
- L is a bond, —O—, —S—, —S—S—, $C_1$-$C_{12}$ alkylene, $C_2$-$C_{12}$ alkenylene, $C_2$-$C_{12}$ alkynylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), ($C_0$-$C_{12}$ alkylene)-heterocyclylene-($C_0$-$C_{12}$ alkylene), ($C_0$-$C_{12}$ heteroalkylene)-heterocyclylene-($C_0$-$C_{12}$ alkylene), ($C_0$-$C_{12}$ alkylene)-aryl-($C_0$-$C_{12}$ heteroalkylene), or ($C_0$-$C_{12}$ heteroalkylene)-heterocyclylene-($C_0$-$C_{12}$ heteroalkylene), wherein each alkylene, alkenylene, alkynylene, heteroalkylene, arylene, heteroarylene, or heterocyclylene is optionally substituted with 1-24 independently selected $R^1$, and combinations thereof;
- each $R^1$ is independently alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$;
- each $R^A$ is independently hydrogen, $C_1$-$C_6$ alkyl, $C_1$-$C_6$ heteroalkyl, or $C_1$-$C_6$ haloalkyl;
- y is an integer between 1 and 100, inclusive; and
- m is 1 or 2.

In certain embodiments, the macromonomer is of the formula:

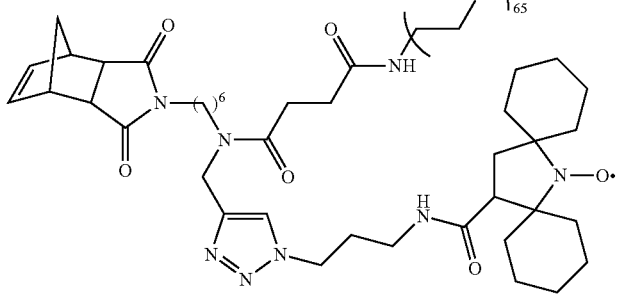

In certain embodiments, the macromonomer is of the formula:

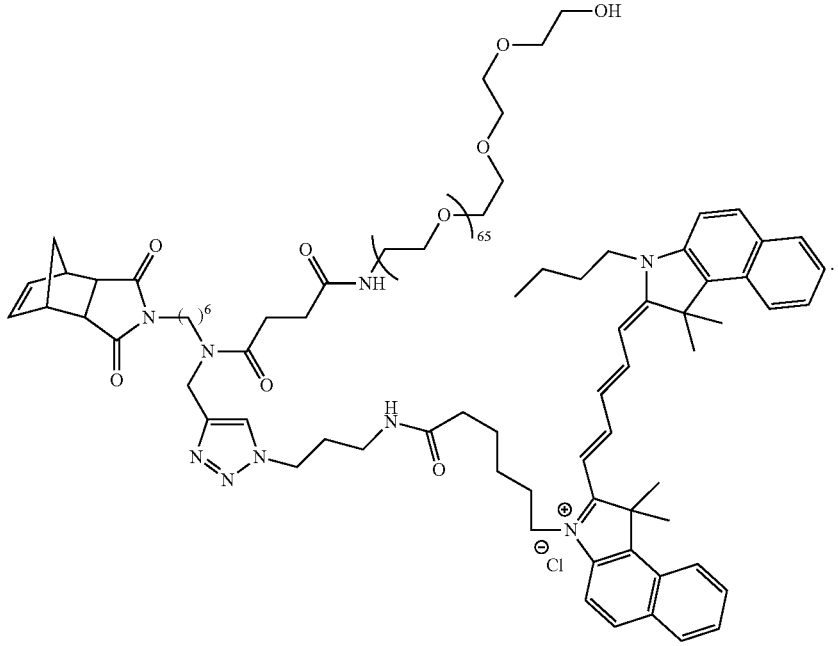

In certain embodiments, the present disclosure describes compositions comprising a polymer described herein (i.e., BASP-ORCAs). In certain embodiments, the composition further comprises a pharmaceutically acceptable excipient.

In certain embodiments, the present disclosure describes kits comprising a polymer described herein (i.e., BASP-ORCAs), or a composition comprising a polymer (i.e., BASP-ORCAs), and instructions for use.

In certain embodiments, the present disclosure provides methods of imaging a subject, the method comprising the steps of: administering to a subject a polymer described herein (i.e., BASP-ORCAs), or a composition comprising a polymer described herein (i.e., BASP-ORCAs); and acquiring an image of at least a portion of the subject. In certain embodiments, the imaging modality is magnetic resonance imaging. In certain embodiments, the imaging modality is near-infrared fluorescence imaging.

In certain embodiments, the present disclosure provides compounds, polymers, particles, nanoparticles, compositions, and kits described herein for use in a method of the present disclosure.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E.L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ is a single bond where the stereochemistry of the moieties immediately attached thereto is not specified, --- is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl").

In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2C_1$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$,

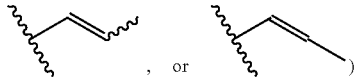

, or )

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or Spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or Spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro 4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$, each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$+X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)$^+$X$^-$, —NH$_3$+X$^-$, N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N($C_{1-6}$ alkyl)C(=O)($C_{1-6}$ alkyl), —$NHCO_2$ ($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —SO$C_{1-6}$ alkyl, —Si($C_{1-6}$ alkyl)$_3$, —OSi($C_{1-6}$ alkyl)$_3$, —C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, —$NO_2$, —C(=O)$R^{aa}$, —$CO_2R^{aa}$, —C(=O)N($R^{bb}$)$_2$, —OC(=O)$R^{aa}$, —$OCO_2R^{aa}$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$. In certain embodiments, the carbon atom substituents are independently halogen, substituted or unsubstituted $C_{1-6}$ alkyl, —$OR^{aa}$, —$SR^{aa}$, —N($R^{bb}$)$_2$, —CN, —SCN, or —$NO_2$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3$, —OP(=O)$_2R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)(O$R^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)(O$R^{cc}$)$_2$, and —$NR^{bb}$P(=O)(N$R^{bb}$)$_2$, wherein $R^{aa}$, $R^{bb}$ and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3$+$X^-$, wherein $R^{bb}$ and $X^-$ are as defined herein.

The term "sulfonyl" refers to a group selected from —$SO_2$N($R^{bb}$)$_2$, —$SO_2R^{aa}$, and —$SO_2OR^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—$CO_2$H), aldehydes (—CHO), esters (—$CO_2R^{aa}$, —C(=O)$SR^{aa}$, C(=S)$SR^{aa}$), amides (C(=O)N($R^{bb}$)$_2$, —C(=O)$NR^{bb}SO_2R^{aa}$, C(=S)N($R^{bb}$)$_2$), and imines (—C(=$NR^{bb}$)$R^{aa}$ C(=$NR^{bb}$)$OR^{aa}$), —C(=$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "boronyl" refers to boranes, boronic acids, boronic esters, borinic acids, and borinic esters, e.g., boronyl groups of the formula —B($R^{aa}$)$_2$, —B(O$R^{cc}$)$_2$, and —B$R^{aa}$(O$R^{cc}$) wherein $R^{aa}$ and $R^{cc}$ are as defined herein.

The term "phosphino" refers to the group —P($R^{cc}$)$_3$, wherein $R^{cc}$ is as defined herein. An exemplary phosphino group is triphenylphosphine.

The term "phosphono" refers to the group —O(P=O)(O$R^{cc}$)$R^{aa}$, wherein $R^{aa}$ and $R^{cc}$ are as defined herein.

The term "phosphoramido" refers to the group —O(P=O)(N$R^{bb}$)$_2$, wherein each $R^{bb}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —SO$R^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilyl ethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(NN-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mb s), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrol e, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4 pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di (4-methoxyphenyl)methyl amine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5- dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$ wherein $R^{aa}$, $R^{bb}$ and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyl di phenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro 4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$ and $R^{cc}$ are as defined herein. Sulfur protecting groups are well known in the art and include those described in detail in *Protecting Groups in Organic Synthesis*, T. W. Greene and P. G. M. Wuts, 3' edition, John Wiley & Sons, 1999, incorporated herein by reference.

The term "heteroatom" refers to an atom that is not hydrogen or carbon. In certain embodiments, the heteroatom is a nitrogen, oxygen, or sulfur. In certain embodiments, the heteroatom is a nitrogen or oxygen. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymer" refers to a molecule including two or more (e.g., 3 or more, 4 or more, 5 or more, 10 or more) repeating units which are covalently bound together. In certain embodiments, a polymer comprises 3 or more, 5 or more, 10 or more, 50 or more, 100 or more, 500 or more, 1000 or more, 2000 or more, 3000 or more, 4000 or more, 5000 or more, 6000 or more, 7000 or more, 8000 or more, 9000 or more, or 10000 or more repeating units. In certain embodiments, a polymer comprises more than 5000 repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. A "graft polymer" is a segmented copolymer with a linear backbone of one composite and randomly distributed branches of another composite. The major difference between graft polymers and bottlebrush polymers (or brush-arm polymers) is the grafting density. The targeted graft density for bottlebrush polymers is that in at least one segment of the copolymer is one graft from each backbone monomer unit. A "star polymer" is a polymer that consists of several polymers chains connected at a core atom, core molecule, or core polymer. Polymers may be natural (e.g., naturally occurring polypeptides), or synthetic (e.g., non-naturally occurring). A polymer may have an overall molecular weight of 50 Da or greater, 100 Da or greater, 500 Da or greater, 1000 Da or greater, 2000 Da or greater, 5000 Da or greater, 10000 Da or greater, 20000 Da or greater, or 50000 Da or greater. Exemplary polymers include, without limitation, poly(ethylene glycol) 200 (PEG200), PEG400, PEG600, PEG800, PEG1000, PEG1500, PEG2000, PEG3000, PEG4000, and PEG6000.

The terms "living polymer" and "living polymerization" refer a polymerization where the ability of a growing polymer chain to terminate has been removed. Chain termination and chain transfer reactions are absent, and the rate of the chain initiation is also much larger than the rate of chain propagation. The result is that the polymer chains grow at a constant rate than see in traditional chain polymerization and their lengths remain very similar.

The terms "number average molecular weight," "number average molar mass," and "Me" are measurements of the molecular mass of a polymer. The number average molecular mass is the ordinary arithmetic mean or average of the molecular masses of the individual polymers. It is determined by measuring the molecular mass of n polymer molecules, summing the masses, and dividing by n. For example, a polymer having 100 repeating units of a monomer with a molecular weight of 100 g/mol would have a number average molecular weight ($M_n$) of 10,000 g/mol [$M_n=(100)*(100 \text{ g/mol})/(1)=10,000$ g/mol]. The number average molecular mass of a polymer can be determined by gel permeation chromatography, viscometry via the Mark-Houwink equation, colligative methods such as vapor pressure osmometry, end-group determination, or $^1$H NMR.

The term "monomer" refers to a molecule that may bind covalently to other molecules to form a polymer. The process by which the monomers are combined to form a polymer is called polymerization. A macromolecule with one end-group that enables it to act as a monomer is called a macromonomer. Molecules made of a small number of monomer units are called oligomers.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, p-xylene.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. In certain embodiments, the animal is a mouse. In certain embodiments, the animal is a human. The animal may be a male or female at any stage of development. The animal may be a transgenic animal or genetically engineered animal. In certain embodiments, the subject is a non-human animal.

The term "administer," "administering," or "administration" refers to implanting, absorbing, ingesting, injecting, inhaling, or otherwise introducing a compound or cell described herein or generated as described herein, or a composition thereof, in or on a subject.

As used herein, the term "salt" refers to any and all salts, and encompasses pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+ (C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, and/or enhances the therapeutic efficacy of another therapeutic agent.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents.

The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The term "crosslinker" refers to a compound that allows for two or more molecules or polymers to be joined by covalent bonds. In certain embodiments, the crosslinker results in a covalent attachment between two polymers.

The term "ring-opening metathesis polymerization (ROMP)" refers to a type of olefin metathesis chain-growth polymerization that is driven by the relief of ring strain in cyclic olefins (e.g. norbornene or cyclopentene). The catalysts used in the ROMP reaction include $RuCl_3$/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium (II), dichloro[1,3-Bis(2-methylphenyl)-2-imidazolidinylidene](benzylidene)(tricyclohexylphosphine) ruthenium (II), dichloro[1,3-bis(2,4,6-trimethylphenyl)-2-imidazolidinylidene][3-(2-pyridinyl)propylidene]ruthenium (II), dichloro(3-methyl-2-butenylidene)bis(tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine)ruthenium(II) (Grubbs I), dichloro[1,3-bis(2,4,6-trimethylphenyl)-2-imidazolidinylidene](benzylidene)(tricyclohexylphosphine) ruthenium (II) (Grubbs II), and dichloro[1,3-bis(2,4,6-trimethylphenyl)-2-imidazolidinylidene](benzylidene)bis(3-bromopyridine)ruthenium(II) (Grubbs III).

The terms "electron paramagnetic resonance (EPR) spectroscopy" or "electron spin resonance (ESR) spectroscopy" refer to a method for studying materials with unpaired electrons. EPR relies on the excitation of electron spins and is particularly useful for studying metal complexes or organic radicals (e.g., nitroxide radicals).

The term "imaging" refers to a technique and process of creating visual representations of the interior of a body or portion thereof (e.g., brain, heart, lung, liver, kidney, spleen, muscle, tissue, and tumor) for clinical analysis and medical intervention, as well as visualization of the function of organs and/or tissues. Medical imaging seeks to reveal internal structures hidden by the skin and bones, as well as to diagnose and sometimes treat disease. Medical imaging also establishes a database of normal anatomy and physiology to make it possible to identify abnormalities. Examples of imaging modalities include, but are not limited to, radiography, magnetic resonance imaging (MRI), nuclear medicine, ultrasound, elastography, tactile imaging, photoacoustic imaging, tomography, echocardiography, near-infrared fluorescence (NIRF) imaging, and magnetic particle imaging.

BRIEF DESCRIPTION OF THE DRAWINGS

The accompanying drawings, which constitute a part of this specification, illustrate several exemplary embodiments of the invention and together with the description, serve to explain certain principles of the invention. The embodiments disclosed in the drawings are exemplary and do not limit the scope of this disclosure.

FIGS. 2A-2C show the transmission electron microscopy image of BASP-ORCA1 ($D_{TEM}$=37±7) after being negatively stained with uranyl acetate (FIG. 2A), electron paramagnetic resonance (EPR) spectra for BASP-ORCA1 and chex-MM (FIG. 2B), and $T_1$ and $T_2$-weighted MRI phantoms for BASP-ORCA1, chex-MM, PBS buffer, chex-bottlebrush, and a PEG-BASP lacking chex (FIG. 2C). In FIG. 2C the concentration of chex-containing samples (BASP-ORCA1, chex-MM, and chex-bottlebrush) ranges from 1 mM to 4 mM chex. The concentration of PEG-BASP lacking chex ranges from 6 mg/mL to 21 mg/mL, which is equivalent to the mass per volume concentration range of BASP-ORCA1.

$$\frac{p/sec/cm^2/sr}{\mu W/cm^2}.$$

Figure 5A:
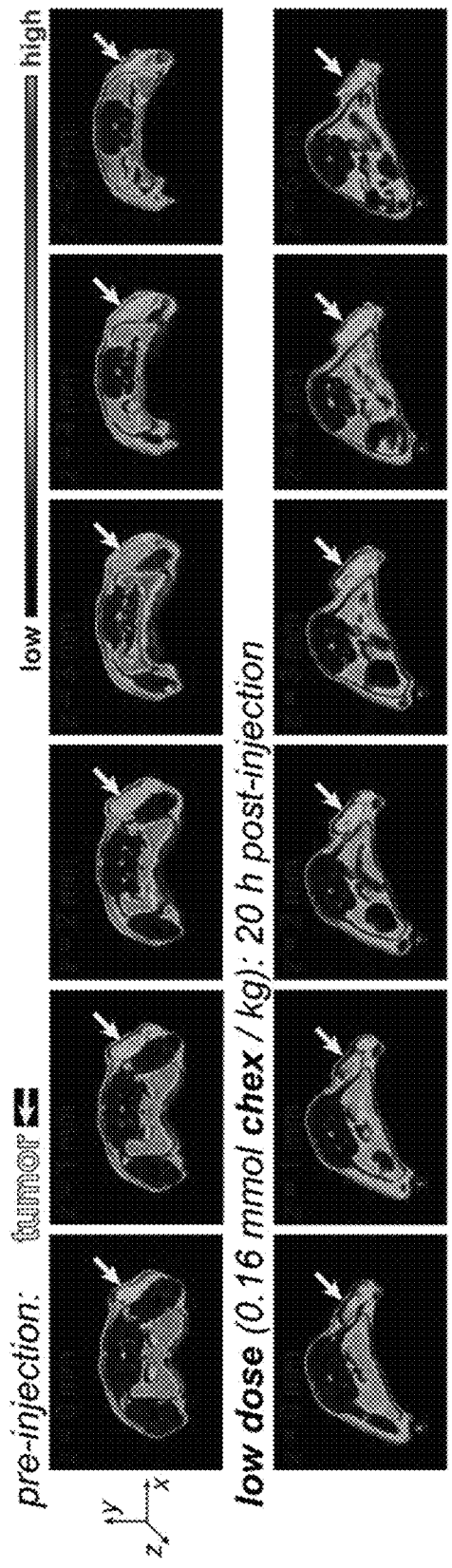
Figure 5B:
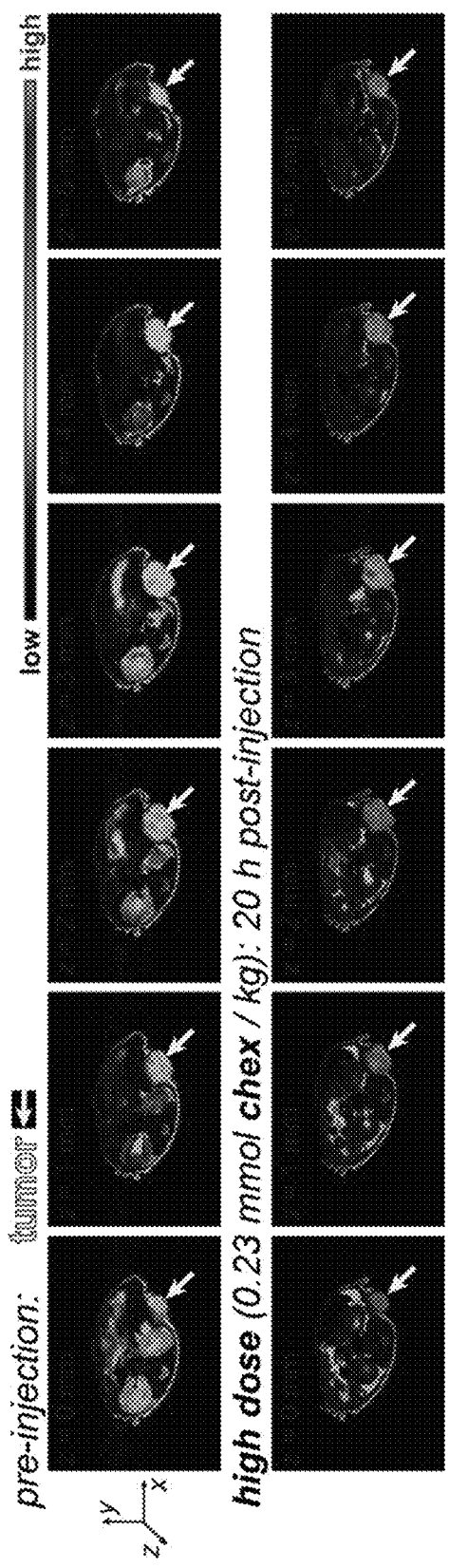
Figure 5C:
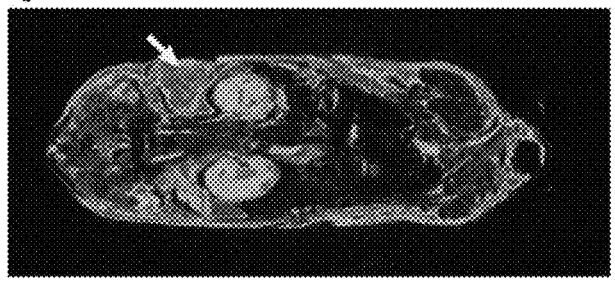
Figure 5C:
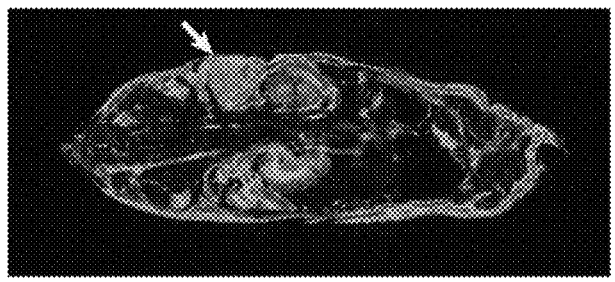
Figure 5D:
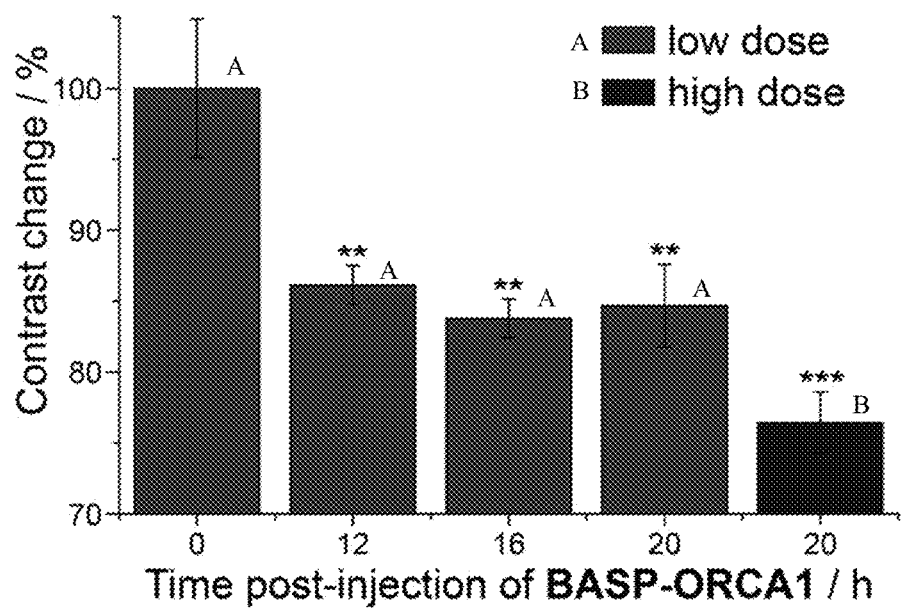

FIGS. 5A-5D show in vivo MRI imaging with BASP-ORCA. FIG. 5A shows $T_2$-weighted MR images of tumor bearing NCR nude mouse before (top row) and 20 hours after (bottom row) injection of 0.16 mmol chex/kg ("low dose") of BASP-ORCA1. Each series of images corresponds to progressive slices in the z-axis through the tumor of the same mouse. FIG. 5B shows $T_2$-weighted MR images of tumor bearing NCR nude mouse before (top row) and 20 hours after (bottom row) injection of 0.23 mmol chex/kg ("high dose") of BASP-ORCA1. Each series of images corresponds to progressive slices in the z-axis through the tumor of the same mouse. FIG. 5C shows $T_2$-weighted coronal MR images before (top) and 20 hours after (bottom) injection of 0.23 mmol chex/kg ("high dose") of BASP-ORCA1. FIG. 5D shows the percent MRI contrast change at various times following BASP-ORCA1 injection compared to pre-injection.

Figure 6A:
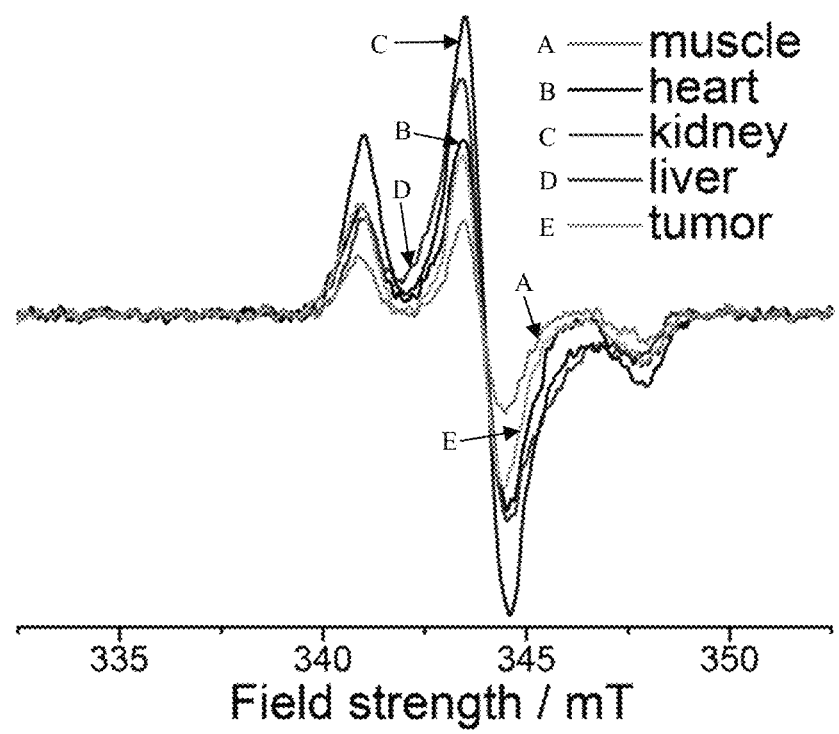
Figure 6B:
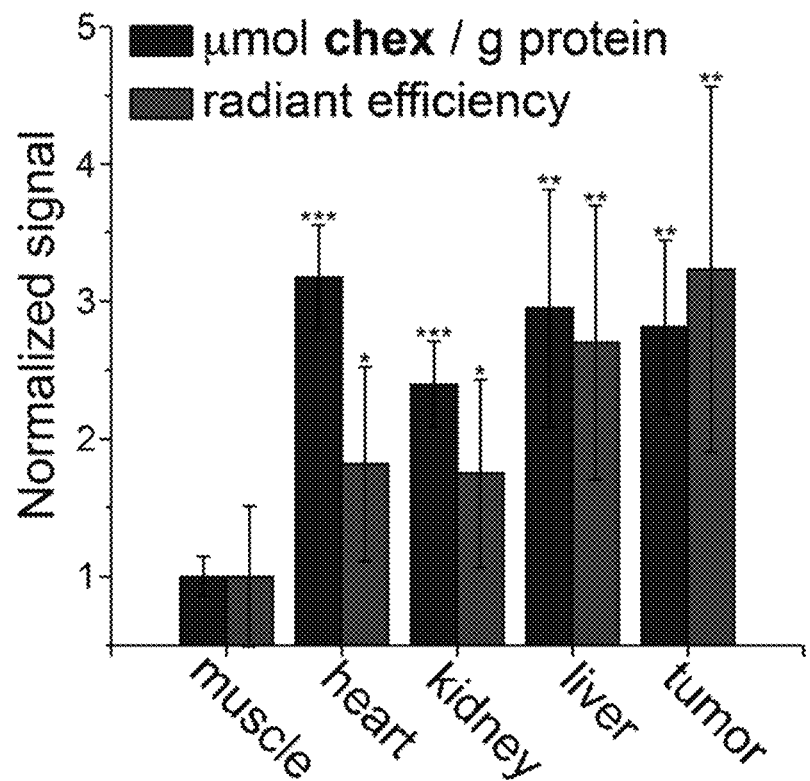

FIGS. 6A-6B show EPR spectra obtained for homogenized tissue samples collected for the same mice imaged in FIGS. 5A-5D 22 hours following BASP-ORCA1 injection (FIG. 6A) and fluorescence radiant efficiencies of the homogenized tissue samples (FIG. 6B). Right-hand bars: Muscle-normalized concentration of chex per milligram of protein as obtained from EPR integration of tissue homogenates. Left-hand bars: Muscle-normalized concentration of Cy5.5 in tissue homogenates as obtained from NIRF imaging.

Figure 7A:
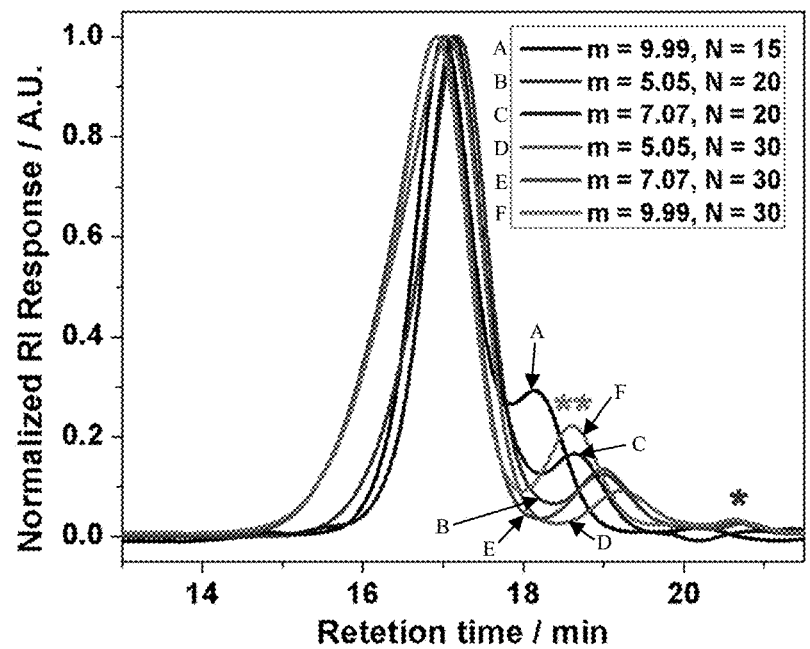
Figure 7B:
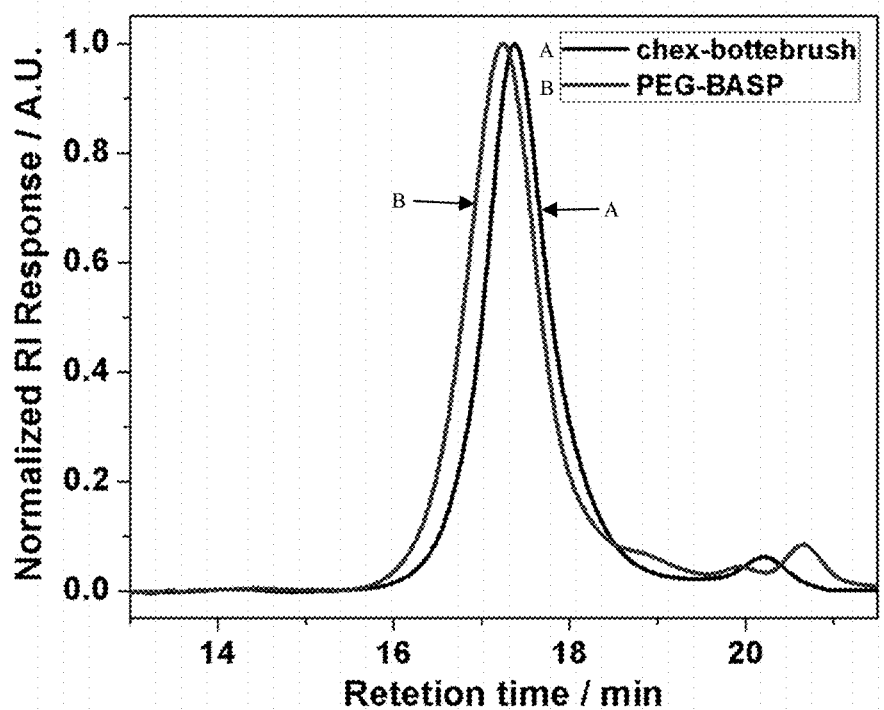

FIGS. 7A-7B show GPC traces. FIG. 7A shows GPC traces of BASP-ORCAs with different brush length (m) and cross-linker equivalents (N). *indicates negligible residual MM; **denotes uncoupled bottlebrush. In all cases, the MM-to-bottlebrush conversions were almost quantitative, while the bottlebrush-to-BASP conversions were ≥85%. FIG. 7B shows GPC traces of chex-bottlebrush and PEG-BASP used for phantom MRI comparison with BASP-ORCA 1.

Figure 8:
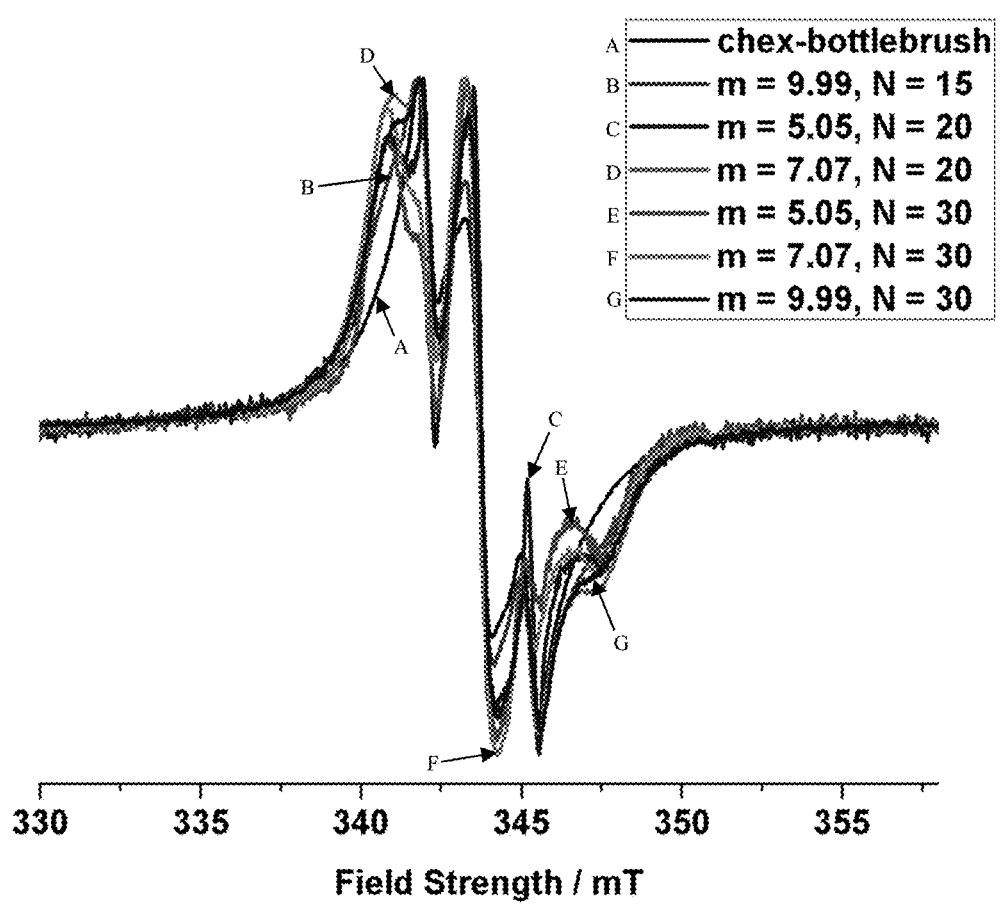
Figure 9A:
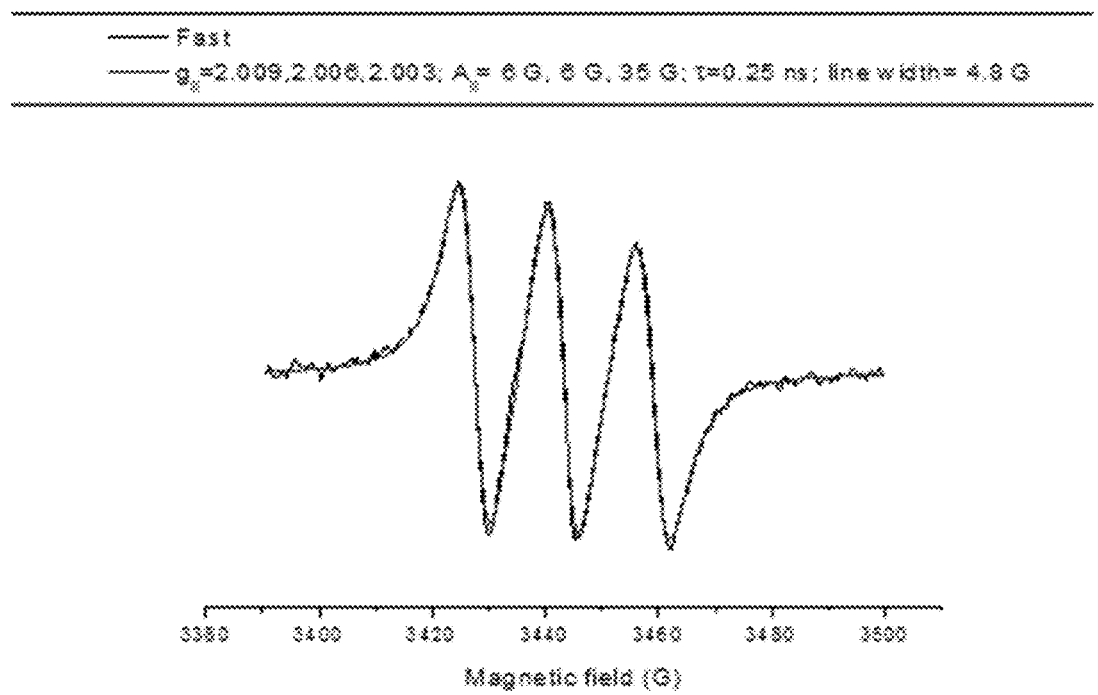
Figure 9B:
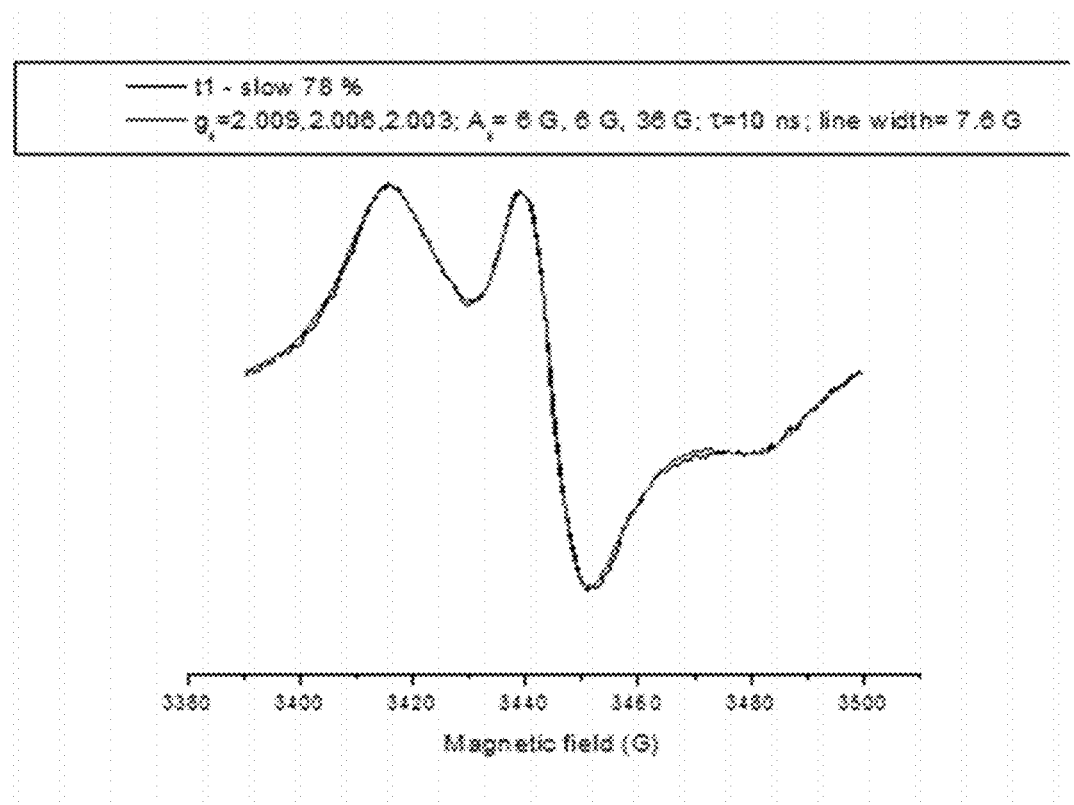
Figure 9C:
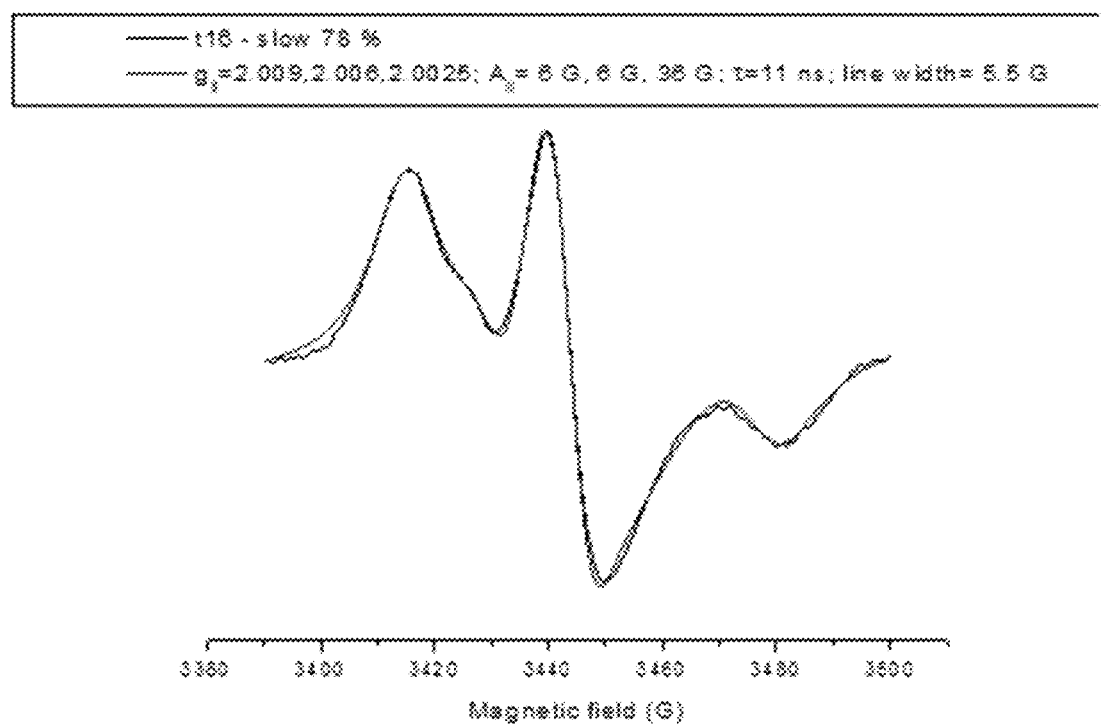
Figure 9D:
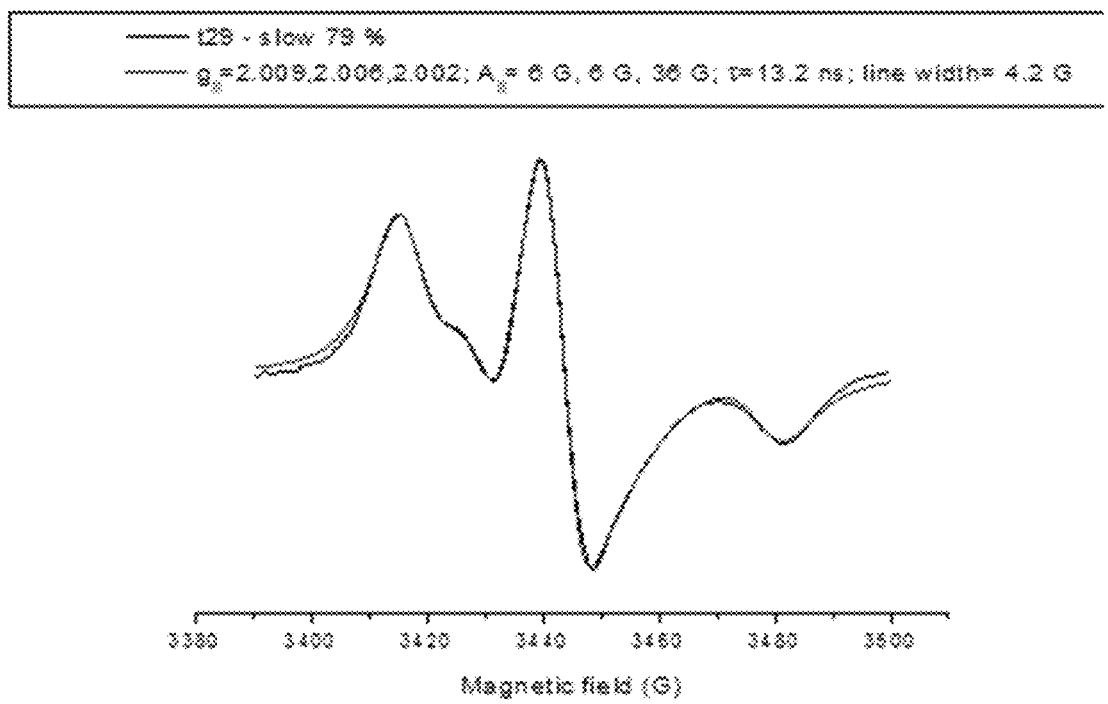

FIG. 8 shows the EPR spectra of BASP-ORCAs of varying composition.

FIGS. 9A-9D show computational analysis of EPR spectra obtained during reduction kinetics experiments. t1=1 minutes, t16=40 minutes, t29=180 minutes following addition of Asc solution.

Figure 10:
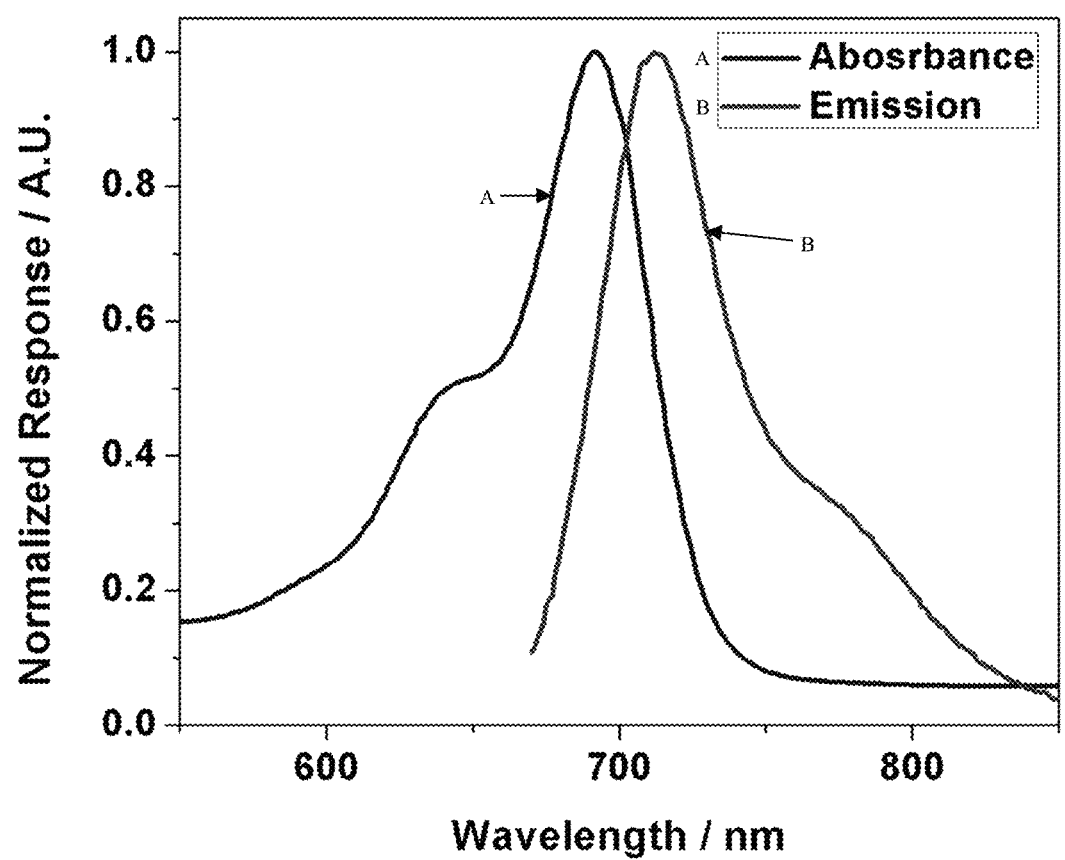

FIG. 10 shows the excitation and emission spectra of BASP-ORCA1.

Figure 11:
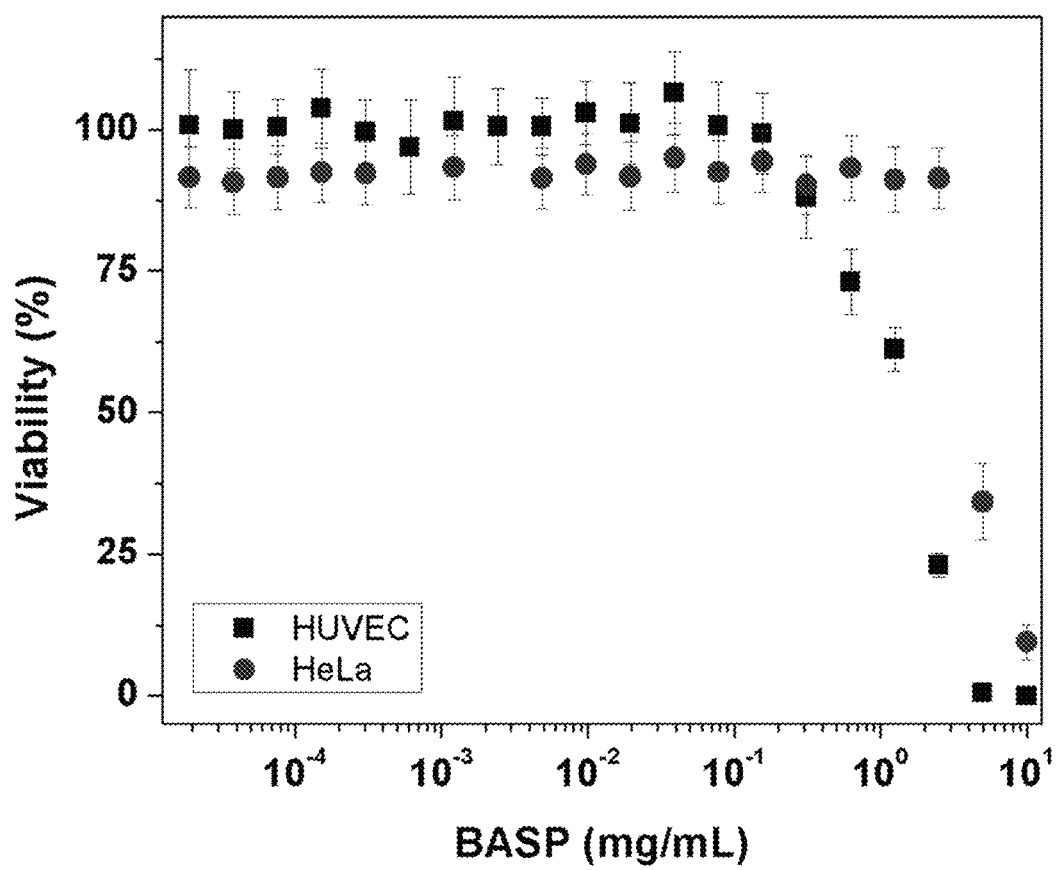

FIG. 11 shows the cell viability assay for BASP-ORCA1 in the toxin-sensitive HUVEC and cancerous HeLa cell lines as measured by CellTiter Glo. No toxicity was observed until high concentrations were reached (up to 0.3 mg/mL and 5 mg/mL for HUVEC and HeLa, respectively).

Figure 12:
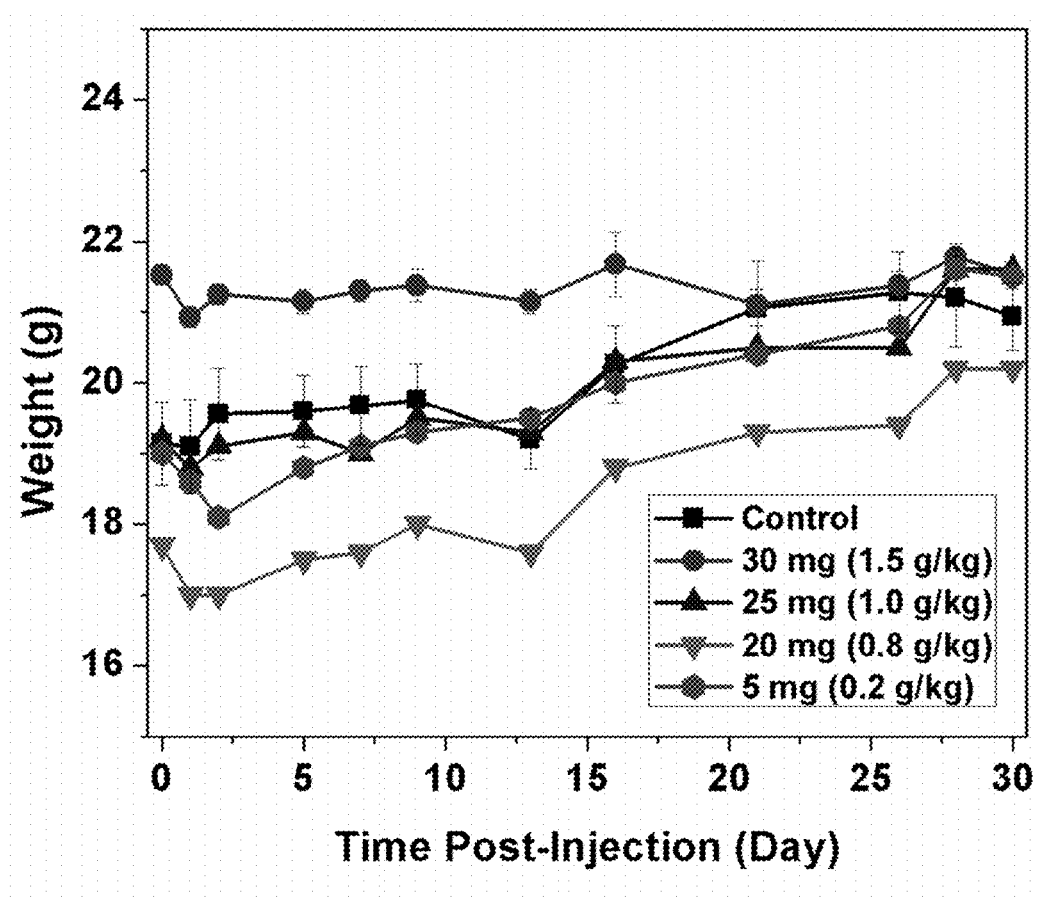

FIG. 12 shows in vivo gross toxicity of BASP-ORCA1 following intravenous injections in BALB/c mice.

Figure 13A:
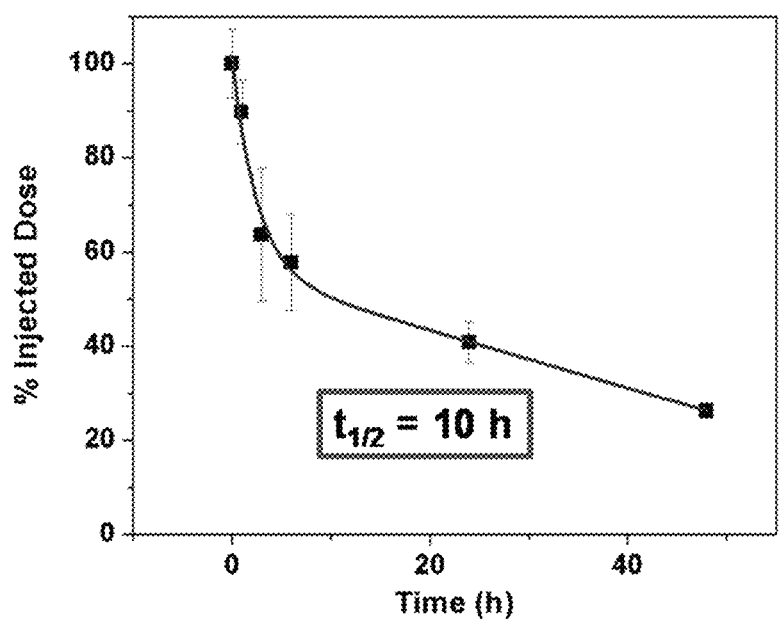
Figure 13B:
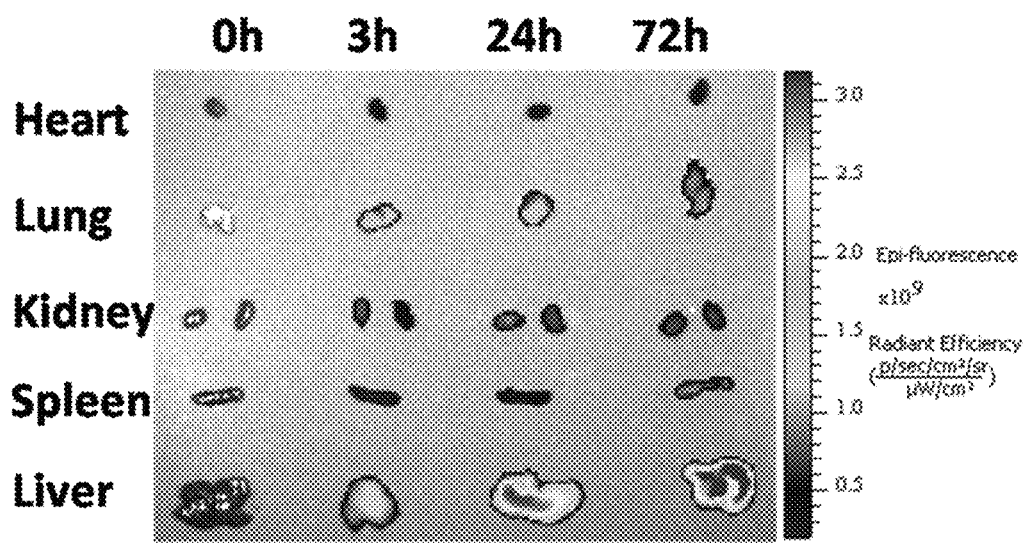
Figure 13C:
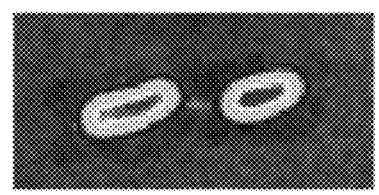

FIGS. 13A-13C show pharmacokinetics (PK) (FIG. 13A), biodistribution (BD) (FIG. 13B), and excrements collected 24 hours after administration of BASP-ORCA1 in BALB/c mice as imaged by NIRF ($\lambda_{ex}/\lambda_{em}$=640/700 nm) (FIG. 13C). PK data were fit into a two-component model using standard procedures ($R^2$=0.95).[101,102]

Figure 14:
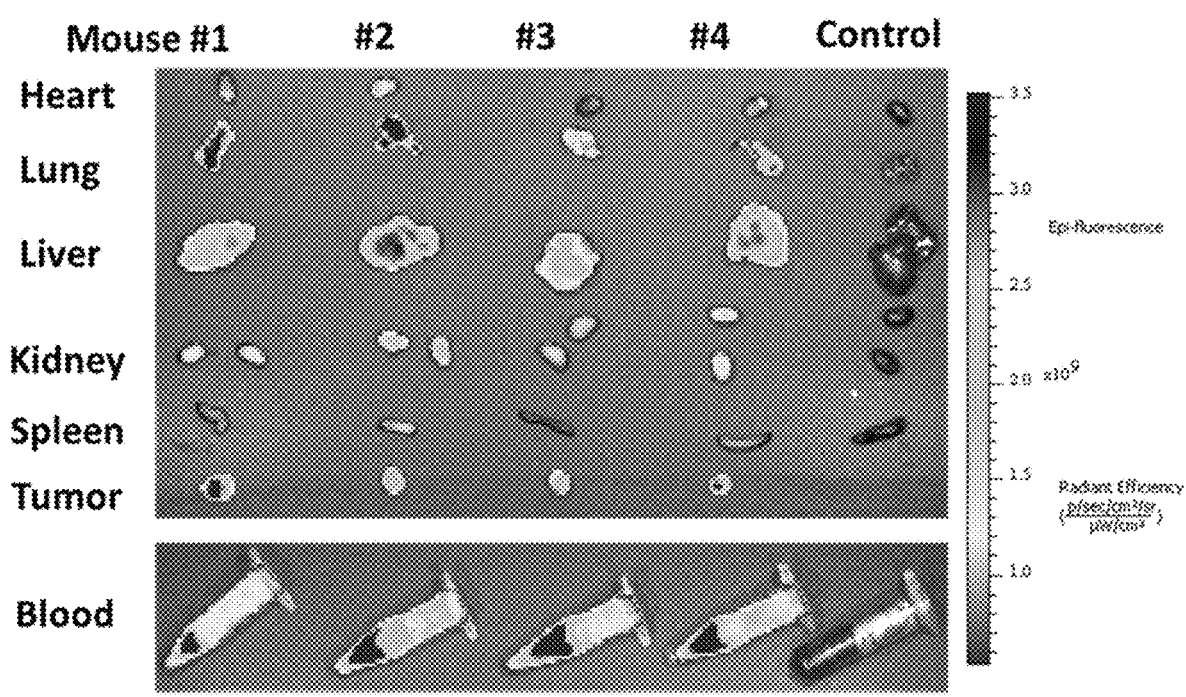

FIG. 14 shows ex vivo BD as assessed by NIRF imaging ($\lambda_{ex}/\lambda_{em}$=640/700 nm) of subcutaneous tumor-bearing NCR-NU mice following injection of BASP-ORCA1.

FIG. 15 shows characterization data for BASP-ORCAs and control compounds.

DETAILED DESCRIPTION OF CERTAIN EMBODIMENTS

The present disclosure provides methods, compounds, particles, nanoparticles, compositions, systems, and kits focused on the synthesis and uses of brush-arm star polymers containing at least one imaging agent. In certain embodiments, the polymers are brush-arm star polymer organic radical contrast agents (BASP-ORCAs). In certain embodiments, the brush-arm star polymer organic radical contrast agents are comprised of brush-arm polymers covalently linked to a polymer core via crosslinkers. In certain embodiments, BASP-ORCAs contain a high concentration of reduction-resistant nitroxide groups bound between a poly(ethylene glycol) (PEG) shell and a polyacetal core.

These polymers are shown to be effective for medical imaging (e.g., brain, heart, lung, liver, kidney, spleen, muscle, tissue, and tumor). In certain embodiments, the imaging modality is magnetic resonance imaging. In certain embodiments, the imaging modality is near-infrared fluorescence imaging.

Brush-Arm Star Polymers

One aspect of the present disclosure relates to brush-arm star polymers comprising at least 100 repeating units selected from Formula (I) and Formula (II):

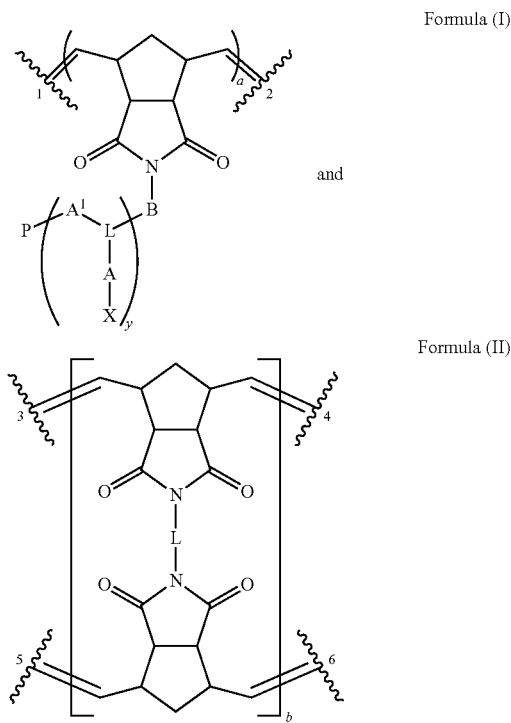

or a salt thereof, wherein:
each of A, $A^1$, and B is independently $C_1$-$C_{12}$ alkylene, $C_2$-$C_{12}$ alkenylene, $C_2$-$C_{12}$ alkynylene, or $C_1$-$C_{12}$ heteroalkylene, $C_2$-$C_{12}$ heteroalkenylene, $C_2$-$C_{12}$ heteroalkynylene, wherein each alkylene, alkenylene, alkynylene, heteroalkylene, heteroalkenylene, or heteroalkynylene is optionally substituted with 1-24 independently selected $R^1$;
X is an imaging agent;
P is alkylene, heteroalkylene, or polymer;
L is a bond, —O—, —S—, —S—S—, $C_1$-$C_{12}$ alkylene, $C_2$-$C_{12}$ alkenylene, $C_2$-$C_{12}$ alkynylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), ($C_0$-$C_{12}$ alkylene)-heterocyclylene-($C_0$-$C_{12}$ alkylene), ($C_0$-$C_{12}$ heteroalkylene)-heterocyclylene-($C_0$-$C_{12}$ alkylene), ($C_0$-$C_{12}$ heteroalkylene)-aryl-($C_0$-$C_{12}$ heteroalkylene), or ($C_0$-$C_{12}$ heteroalkylene)-heterocyclylene-($C_0$-$C_{12}$ heteroalkylene), wherein each alkylene, alkenylene, alkynylene, heteroalkylene, arylene, heteroarylene, or heterocyclylene is optionally substituted with 1-24 independently selected $R^1$, and combinations thereof;
each $R^1$ is independently alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$;
each $R^A$ is independently hydrogen, $C_1$-$C_6$ alkyl, $C_1$-$C_6$ heteroalkyl, or $C_1$-$C_6$ haloalkyl;

each of a and b are independently an integer between 1 and 10000, inclusive;

each of "1", "2", "3", "4", "5", and "6" is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thio; or represents a bond to a structure of Formula (I) or Formula (II);

y is an integer between 1 and 100, inclusive; and m is 1 or 2.

In certain embodiments, P is a polyether, polyester, polyacrylamide, polycarbonate, polysiloxane, polyfluorocarbon, polysulfone, or polystyrene. In certain embodiments, P is a polyether selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline). In certain embodiments, P is a polyester selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutyrate (PHB), polyethylene adipate (PEA), polybutylene succinate (PBS), or poly(3-hydroxybutyrate-co-3-hydroxyvalerate) (PHBV). In certain embodiments, P is a poly(N-alkylacrylamide). In certain embodiments, P is a polycarbonate selected from the group consisting of poly(Bisphenol A carbonate), poly[Bisphenol A carbonate-co-4,4-(3,3,5-trimethylcyclohexylidene)diphenol carbonate], or poly(propylene carbonate). In certain embodiments, P is a polysiloxane. In certain embodiments, P is polydimethylsiloxane (PDMS). In certain embodiments, P is a polyfluorocarbon selected from the group consisting of poly(chlorotrifluoroethylene), poly(ethylene-co-tetrafluoroethylene), poly(tetrafluoroethylene), poly(tetrafluoroethylene-co-perfluoro(propylvinyl ether)), poly(vinylidene fluoride), and poly(vinylidene fluoride-co-hexafluoropropylene). In certain embodiments, P is a polysulfone selected from the group consisting of poly[1-[4-(3-carboxy-4-hydroxyphenylazo)benzenesulfonamido]-1,2-ethanediyl, sodium salt], poly(1-hexadecene-sulfone), poly(oxy-1,4-phenylenesulfonyl-1,4-phenylene), poly(oxy-1,4-phenylenesulfonyl-1,4-phenylene), and polyphenylsulfone.

In certain embodiments, P is poly(ethylene glycol) with a molecular weight ranging from about 200 g/mol to about 6000 g/mol. In certain embodiments, P is poly(ethylene glycol) with a molecular weight about 200 g/mol. In certain embodiments, P is poly(ethylene glycol) with a molecular weight about 200 g/mol. In certain embodiments, P is poly(ethylene glycol) with a molecular weight about 500 g/mol. In certain embodiments, P is poly(ethylene glycol) with a molecular weight about 1000 g/mol. In certain embodiments, P is poly(ethylene glycol) with a molecular weight about 1500 g/mol. In certain embodiments, P is poly(ethylene glycol) with a molecular weight about 2000 g/mol. In certain embodiments, P is poly(ethylene glycol) with a molecular weight about 2500 g/mol. In certain embodiments, P is poly(ethylene glycol) with a molecular weight about 3000 g/mol. In certain embodiments, P is poly(ethylene glycol) with a molecular weight about 3500 g/mol. In certain embodiments, P is poly(ethylene glycol) with a molecular weight about 4000 g/mol. In certain embodiments, P is poly(ethylene glycol) with a molecular weight about 4500 g/mol. In certain embodiments, P is poly(ethylene glycol) with a molecular weight about 5000 g/mol. In certain embodiments, P is poly(ethylene glycol) with a molecular weight about 5500 g/mol. In certain embodiments, P is poly(ethylene glycol) with a molecular weight about 6000 g/mol.

In certain embodiments, B is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, A is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, $A^1$ is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, L is selected from a group consisting of

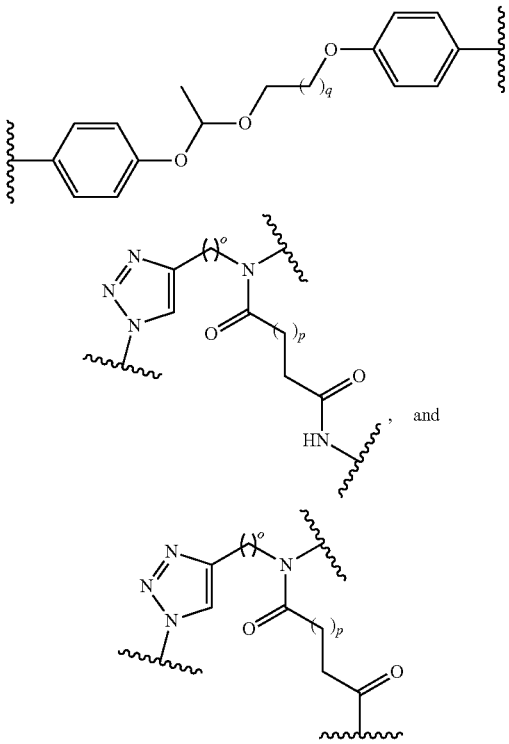

wherein: q, p, and o are independently an integer between 0 and 20, inclusive.

In certain embodiments, L is independently selected from

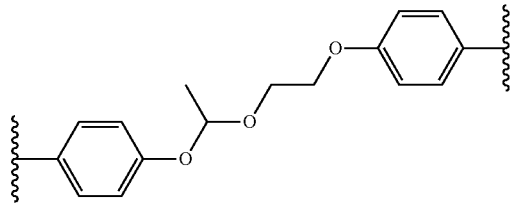

and

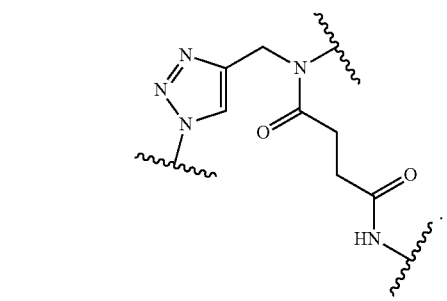

In certain embodiments, X is a chelated metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, X is and inorganic compound. In certain embodiments, X is an organic compound. In certain embodiments, X is metal-free.

In certain embodiments, the imaging agent is an magnetic resonance imaging (MRI) agent. In certain embodiments, the MRI agent is a chelated gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}$Cu diacetyl-bis(N$^4$-methylthiosemicarbazone) ($^{64}$Cu-ASTM), $^{18}$F-fluorodeoxyglucose (FDG), $^{18}$F-fluoride, 3'-deoxy-3'-[$^{18}$F]fluorothymidine (FLT), and $^{18}$F-fluoromisonidazole (FMISO), chelated gallium, chelated technetium-99m, and chelated thallium.

In certain embodiments, the imaging agent is radiographic imaging agent. In certain embodiments, the radiographic imaging agent is selected from the group consisting of chelated barium, gastrografin, metrizoic acid, iotalamic acid, ioxaglate, iopamidol, iohexol, ioxilan, iopromide, iodixanol, and ioversol.

In certain embodiments, the imaging agent X is a radical-containing compound. In certain embodiments, the imaging agent is a nitroxide radical-containing compound. In certain embodiments, the imaging agent X is of the formula:

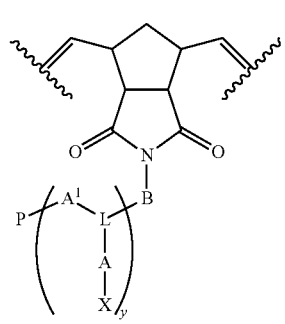

In certain embodiments, the imaging agent X is an organic compound. In certain embodiments, the imaging agent is a salt of an organic compound. In certain embodiments, the imaging agent X is of the formula:

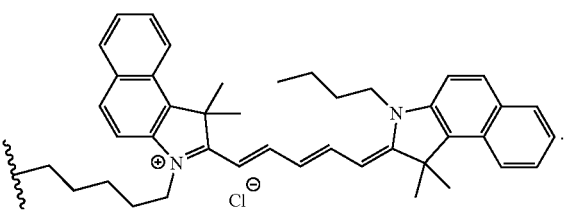 [SMILES: *CCCCC[N+]1=C(/C=C/C=C/C=C2\N(CCCC)c3ccc4ccccc4c3C2(C)C)C(C)(C)c2c1ccc1ccccc21 ; [Cl-]]

In certain embodiments, the repeating unit of Formula (I) is of formula:

Formula (I)

or a salt thereof, wherein:
each of A, A$^1$, and B is independently C$_1$-C$_{12}$ alkylene, C$_2$-C$_{12}$ alkenylene, C$_2$-C$_{12}$ alkynylene, or C$_1$-C$_{12}$ heteroalkylene, C$_2$-C$_{12}$ heteroalkenylene, C$_2$-C$_{12}$ heteroalkynylene,
wherein each alkylene, alkenylene, alkynylene, heteroalkylene, heteroalkenylene, or heteroalkynylene is optionally substituted with 1-24 independently selected R$^1$;
X is an imaging agent;
P is alkylene, heteroalkylene, or polymer;
L is a bond, —O—, —S—, —S—S—, C$_1$-C$_{12}$ alkylene, C$_2$-C$_{12}$ alkenylene, C$_2$-C$_{12}$ alkynylene, C$_1$-C$_{12}$ heteroalkylene, (C$_0$-C$_{12}$ alkylene)-arylene-(C$_0$-C$_{12}$ alkylene), (C$_0$-C$_{12}$ heteroalkylene)-arylene-(C$_0$-C$_{12}$ alkylene), (C$_0$-C$_{12}$ alkylene)-arylene-(C$_0$-C$_{12}$ heteroalkylene), (C$_0$-C$_{12}$ heteroalkylene)-arylene-(C$_0$-C$_{12}$ heteroalkylene), (C$_0$-C$_{12}$ alkylene)-heteroarylene-(C$_0$-C$_{12}$ alkylene), (C$_0$-C$_{12}$ heteroalkylene)-heteroarylene-(C$_0$-C$_{12}$ alkylene), (C$_0$-C$_{12}$ heteroalkylene)-heteroarylene-(C$_0$-C$_{12}$ heteroalkylene), (C$_0$-C$_{12}$ alkylene)-heterocyclylene-(C$_0$-C$_{12}$ alkylene), (C$_0$-C$_{12}$ heteroalkylene)- heterocyclylene-(C$_0$-C$_{12}$ alkylene), (C$_0$-C$_{12}$ heteroalkylene)-aryl-(C$_0$-C$_{12}$ heteroalkylene), or (C$_0$-C$_{12}$ heteroalkylene)-heterocyclylene-(C$_0$-C$_{12}$ heteroalkylene), wherein each alkylene, alkenylene, alkynylene, heteroalkylene, arylene, heteroarylene, or heterocyclylene is optionally substituted with 1-24 independently selected R$^1$, and combinations thereof, each R$^1$ is independently alkyl, alkenyl, alkynyl, heteroalkyl, halo, cyano, oxo, nitro, —OR$^A$, —N(R$^A$)$_2$, —NR$^A$C(O)R$^A$, —NR$^A$C(O)OR$^A$, —NR$^A$C(O)N(R$^A$)$_2$, —C(O)N(R$^A$)$_2$, —C(O)R$^A$, —C(O)OR$^A$, —OC(O)R$^A$, —OC(O)OR$^A$, —OC(O)N(R$^A$)$_2$, —SR$^A$, or —S(O)$_m$R$^A$;

each R$^A$ is independently hydrogen, C$_1$-C$_6$ alkyl, C$_1$-C$_6$ heteroalkyl, or C$_1$-C$_6$ haloalkyl;

y is an integer between 1 and 100, inclusive; and m is 1 or 2.

In certain embodiments, the repeating unit is of formula:

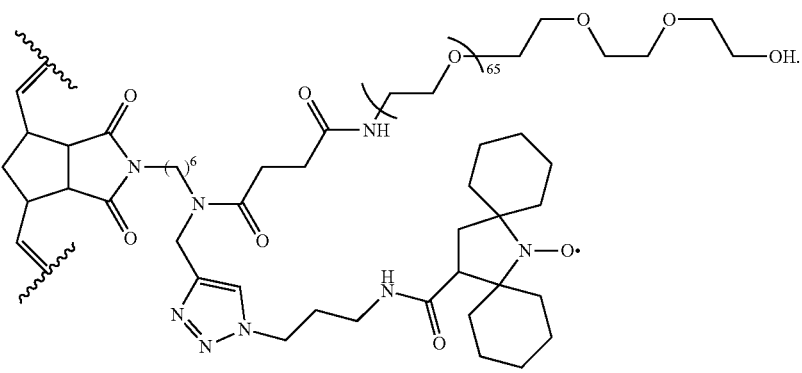

In certain embodiments, the repeating unit is of the formula:

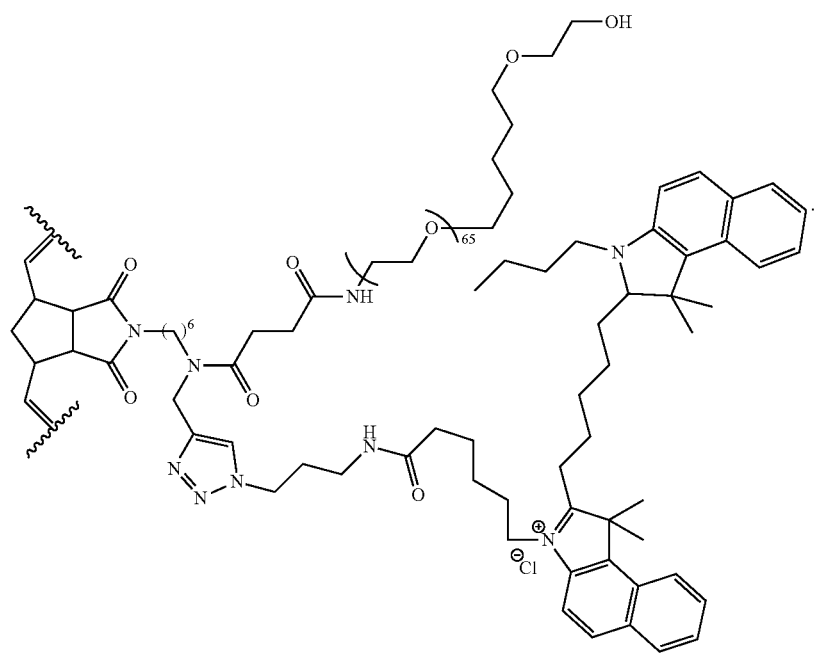

In certain embodiments, the repeating unit of Formula (II) is of formula:

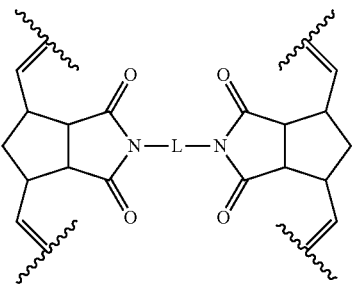

Formula (II)

or a salt thereof, wherein:

L is a bond, —O—, —S—, —S—S—, C$_1$-C$_{12}$ alkylene, C$_2$-C$_{12}$ alkenylene, C$_2$-C$_{12}$ alkynylene, C$_1$-C$_{12}$ heteroalkylene, (C$_0$-C$_{12}$ alkylene)-arylene-(C$_0$-C$_{12}$ alkylene), (C$_0$-C$_{12}$ heteroalkylene)-arylene-(C$_0$-C$_{12}$ alkylene), (C$_0$-C$_{12}$ alkylene)-arylene-(C$_0$-C$_{12}$ heteroalkylene), (C$_0$-C$_{12}$ heteroalkylene)-arylene-(C$_0$-C$_{12}$ heteroalkylene), (C$_0$-C$_{12}$ alkylene)-heteroarylene-(C$_0$-C$_{12}$ alkylene), (C$_0$-C$_{12}$ heteroalkylene)-heteroarylene-(C$_0$-C$_{12}$ alkylene), (C$_0$-C$_{12}$ heteroalkylene)-heteroarylene-(C$_0$-C$_{12}$ heteroalkylene), (C$_0$-C$_{12}$ alkylene)-heterocyclylene-(C$_0$-C$_{12}$ alkylene), (C$_0$-C$_{12}$ heteroalkylene)-heterocyclylene-(C$_0$-C$_{12}$ alkylene), (C$_0$-C$_{12}$ heteroalkylene)-aryl-(C$_0$-C$_{12}$ heteroalkylene), or (C$_0$-C$_{12}$ heteroalkylene)-heterocyclylene-(C$_0$-C$_{12}$ heteroalkylene), wherein each alkylene, alkenylene, alkynylene, heteroalkylene, arylene, heteroarylene, or heterocyclylene is optionally substituted with 1-24 independently selected R$^1$, and combinations thereof;

each R$^1$ is independently alkyl, alkenyl, alkynyl, heteroalkyl, halo, cyano, oxo, nitro, —OR$^A$, —N(R$^A$)$_2$, —NR$^A$C(O)R$^A$, —NR$^A$C(O)OR$^A$, —NR$^A$C(O)N(R$^A$)$_2$, —C(O)N(R$^A$)$_2$, —C(O)R$^A$, —C(O)OR$^A$, —OC(O)R$^A$, —OC(O)OR$^A$, —OC(O)N(R$^A$)$_2$, —SR$^A$, or —S(O)$_m$R$^A$;

each R$^A$ is independently hydrogen, C$_1$-C$_6$ alkyl, C$_1$-C$_6$ heteroalkyl, or C$_1$-C$_6$ haloalkyl; and m is 1 or 2.

In certain embodiments, the repeating unit is of formula:

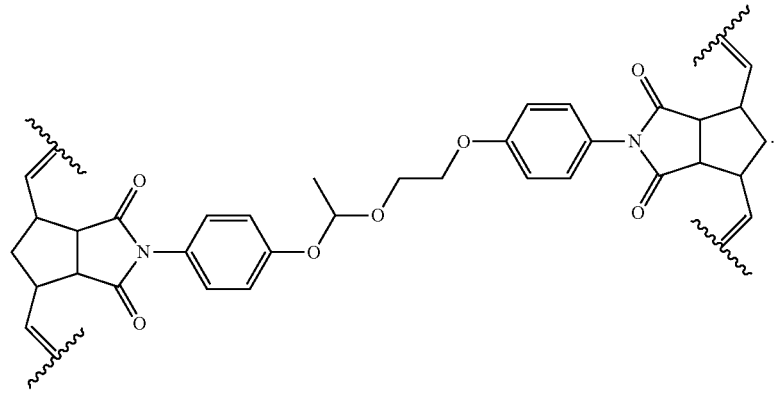

In certain embodiments, the ratio of repeating unit of Formula (I) and repeating unit of Formula (II) is between about 1:20 to about 20:1, respectively. In certain embodiments, the ratio of repeating unit of Formula (I) and repeating unit of Formula (H) is about 1:20, respectively. In certain embodiments, the ratio of repeating unit of Formula (I) and repeating unit of Formula (11) is about 1:19, respectively. In certain embodiments, the ratio of repeating unit of Formula (I) and repeating unit of Formula (II) is about 1:18, respectively. In certain embodiments, the ratio of repeating unit of Formula (I) and repeating unit of Formula (II) is about 1:17, respectively. In certain embodiments, the ratio of repeating unit of Formula (I) and repeating unit of Formula (II) is about 1:16, respectively. In certain embodiments, the ratio of repeating unit of Formula (I) and repeating unit of Formula (II) is about 1:15, respectively. In certain embodiments, the ratio of repeating unit of Formula (I) and repeating unit of Formula (II) is about 1:14, respectively. In certain embodiments, the ratio of repeating unit of Formula (I) and repeating unit of Formula (II) is about 1:13, respectively. In certain embodiments, the ratio of repeating unit of Formula (I) and repeating unit of Formula (11) is about 1:12, respectively. In certain embodiments, the ratio of repeating unit of Formula (I) and repeating unit of Formula (II) is about 1:11, respectively. In certain embodiments, the ratio of repeating unit of Formula (I) and repeating unit of Formula (II) is about 1:10, respectively. In certain embodiments, the ratio of repeating unit of Formula (I) and repeating unit of Formula (II) is about 1:9, respectively. In certain embodiments, the ratio of repeating unit of Formula (I) and repeating unit of Formula (II) is about 1:8, respectively. In certain embodiments, the ratio of repeating unit of Formula (I) and repeating unit of Formula (II) is about 1:7, respectively. In certain embodiments, the ratio of repeating unit of Formula (I) and repeating unit of Formula (II) is about 1:6, respectively. In certain embodiments, the ratio of repeating unit of Formula (I) and repeating unit of Formula (II) is about 1:5, respectively. In certain embodiments, the ratio of repeating unit of Formula (I) and repeating unit of Formula (II) is about 1:4, respectively. In certain embodiments, the ratio of repeating unit of Formula (I) and repeating unit of Formula (II) is about 1:3, respectively. In certain embodiments, the ratio of repeating unit of Formula (I) and repeating unit of Formula (II) is about 1:2, respectively. In certain embodiments, the ratio of repeating unit of Formula (I) and repeating unit of Formula (II) is about 1:1, respectively. In certain embodiments, the ratio of repeating unit of Formula (I) and repeating unit of Formula (II) is about 2:1, respectively. In certain embodiments, the ratio of repeating unit of Formula (I) and repeating unit of Formula (II) is about 3:1, respectively. In certain embodiments, the ratio of repeating unit of Formula (I) and repeating unit of Formula (II) is about 4:1, respectively. In certain embodiments, the ratio of repeating unit of Formula (I) and repeating unit of Formula (II) is about 5:1, respectively. In certain embodiments, the ratio of repeating unit of Formula (I) and repeating unit of Formula (II) is about 6:1, respectively. In certain embodiments, the ratio of repeating unit of Formula (I) and repeating unit of Formula (11) is about 7:1, respectively. In certain embodiments, the ratio of repeating unit of Formula (I) and repeating unit of Formula (II) is about 8:1, respectively. In certain embodiments, the ratio of repeating unit of Formula (I) and repeating unit of Formula (II) is about 9:1, respectively. In certain embodiments, the ratio of repeating unit of Formula (I) and repeating unit of Formula (II) is about 10:1, respectively. In certain embodiments, the ratio of repeating unit of Formula (I) and repeating unit of Formula (II) is about 11:1, respectively. In certain embodiments, the ratio of repeating unit of Formula (I) and repeating unit of Formula (II) is about 12:1, respectively. In certain embodiments, the ratio of repeating unit of Formula (I) and repeating unit of Formula (II) is about 13:1, respectively. In certain embodiments, the ratio of repeating unit of Formula (I) and repeating unit of Formula (II) is about 14:1, respectively. In certain embodiments, the ratio of repeating unit of Formula (I) and repeating unit of Formula (II) is about 15:1, respectively. In certain embodiments, the ratio of repeating unit of Formula (I) and repeating unit of Formula (II) is about 16:1, respectively. In certain embodiments, the ratio of repeating unit of Formula (I) and repeating unit of Formula (II) is about 17:1, respectively. In certain embodiments, the ratio of repeating unit of Formula (I) and repeating unit of Formula (II) is about 18:1, respectively. In certain embodiments, the ratio of repeating unit of Formula (I) and repeating unit of Formula (II) is about 19:1, respectively. In certain embodiments, the ratio of repeating unit of Formula (I) and repeating unit of Formula (II) is about 20:1, respectively.

In certain embodiments, the polymer forms a particle or nanoparticle of a diameter between about 10 nm and about 1000 nm. In certain embodiments, the polymer forms a particle of a diameter between about 10 nm and about 100 nm. In certain embodiments, the polymer forms a particle of a diameter between about 100 nm and about 200 nm. In certain embodiments, the polymer forms a particle of a diameter between about 200 nm and about 300 nm. In certain embodiments, the polymer forms a particle of a diameter between about 300 nm and about 400 nm. In certain embodiments, the polymer forms a particle of a diameter between about 400 nm and about 500 nm. In certain embodiments, the polymer forms a particle of a diameter between about 500 nm and about 600 nm. In certain embodiments, the polymer forms a particle of a diameter between about 600 nm and about 700 nm. In certain embodiments, the polymer forms a particle of a diameter between about 700 nm and about 800 nm. In certain embodiments, the polymer forms a particle of a diameter between about 800 nm and about 900 nm. In certain embodiments, the polymer forms a particle of a diameter between about 900 nm and about 1000 nm. In certain embodiments, the polymer forms a particle of a diameter between about 28 nm and about 49 nm. In certain embodiments, the polymer forms a particle of a diameter between about 25 nm and about 40 nm.

Methods for Preparing Brush-Arm Star Polymers

In another aspect of the present disclosure, a method of producing a brush-arm star polymer comprising an imaging agent is described herein, the method comprises the steps of: reacting one or more macromonomers containing an imaging agent with a metathesis catalyst to form a living polymer; and mixing a crosslinker with the living polymer. In certain embodiments, at least two different macromonomers each containing a different imaging agent are reacted.

In certain embodiments, the brush-arm star polymer is prepared by reacting macromonomer

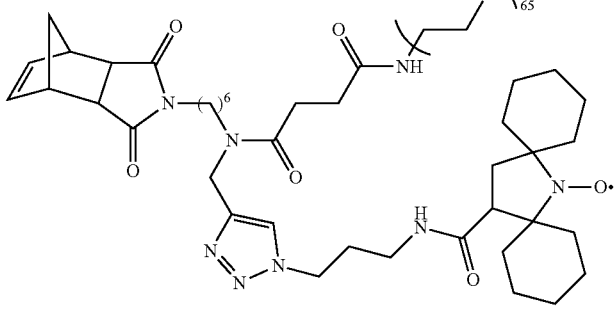

(chex-MM)

macromonomer

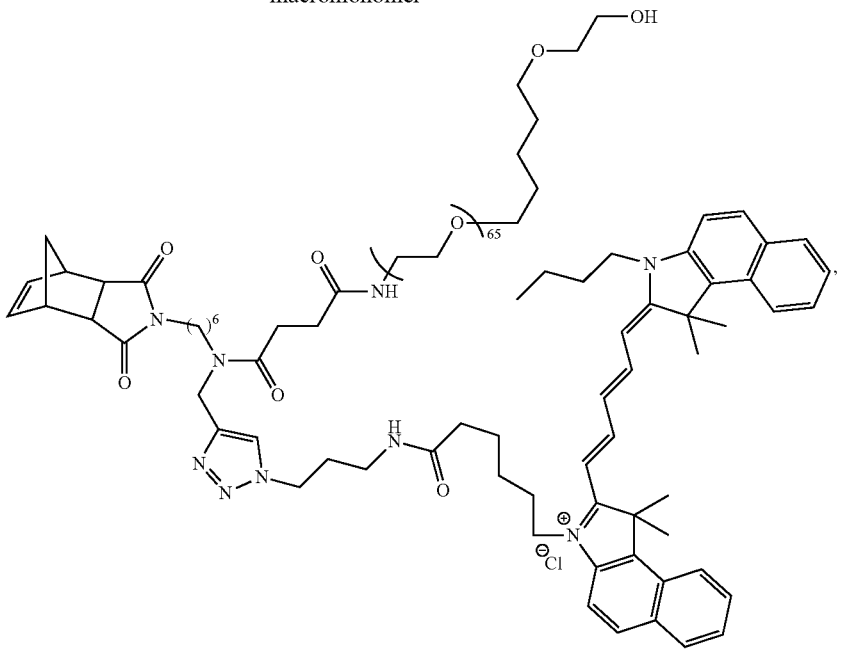

(Cy-MM)

a and ring-opening metathesis catalyst in a solvent to form a living polymer in the first step. In the second step the living polymer is then mixed with crosslinker

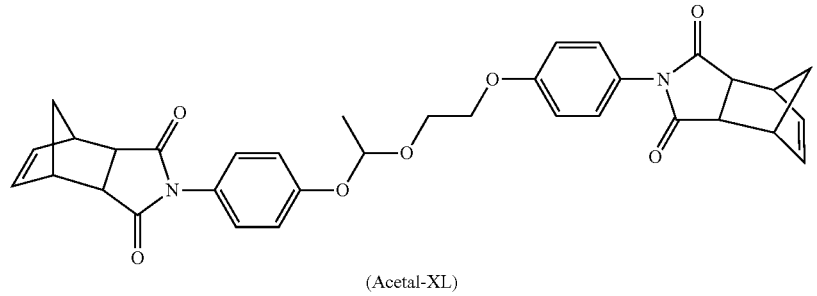 [SMILES: CC(OCCOc1ccc(N2C(=O)C3C4C=CC(C4)C3C2=O)cc1)Oc1ccc(N2C(=O)C3C4C=CC(C4)C3C2=O)cc1]

(Acetal-XL)

to form the brush-arm star polymer. In certain embodiments the ring-opening methathesis catalyst is Grubbs $3^{rd}$ generation bispyridyl catalyst (Grubbs III).

In certain embodiments, the reaction time of the first step is between about 10 minutes and about 60 minutes. In certain embodiments, the reaction time of the first step is about 30 minutes. In certain embodiments, the reaction time of the second step is between about 1 hour and about 24 hours. In certain embodiments, the reaction time of the second step is about 6 hours.

In certain embodiments, the solvent used to prepare the brush-arm star polymer can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-di methylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, p-xylene. In certain embodiments, the solvent used to prepare the brush-arm star polymer is tetrahyrdofuran (THF).

In certain embodiments, the molar ratio of chex-MM and Cy-MM is between about 1:1 and about 1000:1. In certain embodiments, the molar ratio of chex-MM and Cy-MM is about 100:1.

In certain embodiments, the molar ratio of (chex-MM+Cy-MM) and ring-opening metathesis catalyst is between about 1:1 and about 100:1. In certain embodiments, the molar ratio of (chex-MM+Cy-MM) and Grubbs (III) is about 5.05:1. In certain embodiments, the molar ratio of (chex-MM+Cy-MM) and Grubbs (III) is about 7.07:1. In certain embodiments, the molar ratio of (chex-MM+Cy-MM) and Grubbs (III) is about 9.99:1.

In certain embodiments, the molar equivalents of Acetal-XL with respect to Grubbs III is between about 1 equivalent and about 100 equivalents. In certain embodiments, the molar equivalents of Acetal-XL with respect to Grubbs III is about 15 equivalents. In certain embodiments, the molar equivalents of Acetal-XL with respect to Grubbs III is about 20 equivalents. In certain embodiments, the molar equivalents of Acetal-XL with respect to Grubbs III is about 30 equivalents.

In certain embodiments, the macromonomer is of Formula (III):

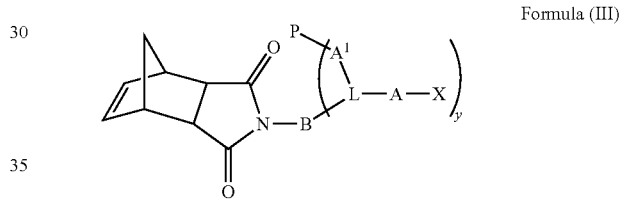

Formula (III)

or a salt thereof, wherein: each of A, $A^1$, and B is independently $C_1$-$C_{12}$ alkylene, $C_2$-$C_{12}$ alkenylene, $C_2$-$C_{12}$ alkynylene, or $C_1$-$C_{12}$ heteroalkylene, $C_2$-$C_{12}$ heteroalkenylene, $C_2$-$C_{12}$ heteroalkynylene, wherein each alkylene, alkenylene, alkynylene, heteroalkylene, heteroalkenylene, or heteroalkynylene is optionally substituted with 1-24 independently selected $R^1$; X is an imaging agent; P is alkylene, heteroalkylene, or polymer; L is a bond, —O—, —S—, —S—S—, $C_1$-$C_{12}$ alkylene, $C_2$-$C_{12}$ alkenylene, $C_2$-$C_{12}$ alkynylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), ($C_0$-$C_{12}$ alkylene)-heterocyclylene-($C_0$-$C_{12}$ alkylene), ($C_0$-$C_{12}$ heteroalkylene)-heterocyclylene-($C_0$-$C_{12}$ alkylene), ($C_0$-$C_{12}$ heteroalkylene)-aryl-($C_0$-$C_{12}$ heteroalkylene), or ($C_0$-$C_{12}$ heteroalkylene)-heterocyclylene-($C_0$-$C_{12}$ heteroalkylene), wherein each alkylene, alkenylene, alkynylene, heteroalkylene, arylene, heteroarylene, or heterocyclylene is optionally substituted with 1-24 independently selected $R^1$, and combinations thereof; each $R^1$ is independently alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; y is an integer between 1 and 100, inclusive; and m is 1 or 2.

In certain embodiments, P is poly(ethylene glycol) with a molecular weight ranging from about 200 g/mol to about 6000 g/mol.

In certain embodiments, B is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, A is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, $A^1$ is $C_1$-$C_{12}$ alkylene, optionally substituted with 1-24 independently selected $R^1$; $R^1$ is alkyl, alkenyl, alkynyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, or —$S(O)_mR^A$; each $R^A$ is independently hydrogen, $C_1$-$C_6$ alkyl, $C_1$-$C_6$ heteroalkyl, or $C_1$-$C_6$ haloalkyl; and m is 1 or 2.

In certain embodiments, the metathesis catalyst is a ring-opening metathesis polymerization (ROMP) catalyst. In certain embodiments, the metathesis catalyst is a transition metal complex. In certain embodiments, the metal is selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, and meitnerium. In certain embodiments, the metathesis catalyst is a ruthenium complex. In certain embodiments, the metathesis catalyst is a molybdenum complex. In certain embodiments, the metathesis catalyst is a zirconium complex. In certain embodiments, the metathesis catalyst is selected from the group consisting of RuC13/alcohol mixture, bis(cyclopentadienyl)dimethylzirconium(IV), dichloro[1,3-bis(2,6-isopropylphenyl)-2-imidazolidinylidene](benzylidene)(tricyclohexylphosphine)ruthenium(II), dichloro[1,3-Bis(2-methylphenyl)-2-imidazolidinylidene](benzylidene)(tricyclohexylphosphine) ruthenium(II), dichloro[1,3-bis(2,4,6-trimethylphenyl)-2-imidazolidinylidene][3-(2-pyridinyl)propylidene]ruthenium(II), dichloro(3-methyl-2-butenylidene)bis (tricyclopentylphosphine)ruthenium(II), dichloro[1,3-bis(2-methylphenyl)-2-imidazolidinylidene](2-isopropoxyphenylmethylene)ruthenium(II) (Grubbs C571), dichloro(benzylidene)bis(tricyclohexylphosphine) ruthenium(II) (Grubbs I), dichloro[1,3-bis(2,4,6-trimethylphenyl)-2-imidazolidinylidene](benzylidene)(tricyclohexylphosphine) ruthenium(II) (Grubbs II), and dichloro[1,3-bis(2,4,6-trimethylphenyl)-2-imidazolidinylidene](benzylidene)bis(3-bromopyridine)ruthenium(II) (Grubbs III). In certain embodiment, the metathesis catalyst is of the formula:

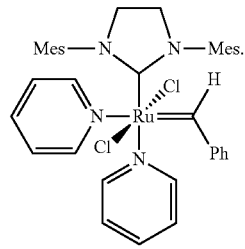

Compositions and Kits

In one aspect of the present disclosure, compositions and kits are described herein. In certain embodiments, a composition is comprised of a polymer described herein and a pharmaceutically acceptable excipient. In certain embodiments, a composition is comprised of an effective amount of a polymer described herein.

Compositions described herein can be prepared by any method known in the art. In general, such preparatory methods include bringing the polymer described herein into association with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Although the descriptions of compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound or polymer described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits. The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, the kits are comprised are comprised of a polymer described herein and instructions for use. In certain embodiments, the kits are comprised of a composition described herein and instructions for use.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. A kit described herein may include one or more additional pharmaceutical agents described herein as a separate composition.

Methods of Treatment

In one aspect of the present disclosure, methods of imaging a subject or a portion of a subject are described herein, the method comprising steps of: administering to a subject a polymer described herein, or a composition described herein; and acquiring an image. In certain embodiments, the imaging modality is selected from the group consisting of radiography, magnetic resonance imaging (MRI), nuclear medicine, ultrasound, elastography, tactile imaging, photoacoustic imaging, tomography, echocardiography, near-infrared fluorescence (NIRF) imaging, and magnetic particle imaging. In certain embodiments, the imaging modality is magnetic resonance imaging (MRI). In certain embodiments, the imaging modality is near-infrared fluorescence (NIRF) imaging.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In some embodiments, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs).

In certain embodiments, the time period between administering to a subject a polymer described herein, or a composition described herein; and acquiring an image is between about 1 minute and about 100 hours. In certain embodiments, the time period between administering to a subject a polymer described herein, or a composition described herein; and acquiring an image is between about 1 hour and about 100 hours. In certain embodiments, the time period between administering to a subject a polymer described herein, or a composition described herein; and acquiring an image is between about 1 hour and about 50 hours. In certain embodiments, the time period between administering to a subject a polymer described herein, or a composition described herein; and acquiring an image is between about 1 hour and about 20 hours. In certain embodiments, the time period between administering to a subject a polymer described herein, or a composition described herein; and acquiring an image is between about 1 hour and about 10 hours. In certain embodiments, the time period between administering to a subject a polymer described herein, or a composition described herein; and acquiring an image is between about 1 hour and about 5 hours.

EXAMPLES

In order that the invention described herein may be more fully understood, the following examples are set forth. The examples described in this application are offered to illustrate the methods, compositions, and systems provided herein and are not to be construed in any way as limiting their scope.

BASP-ORCA Design and Synthesis

Figure 1A:
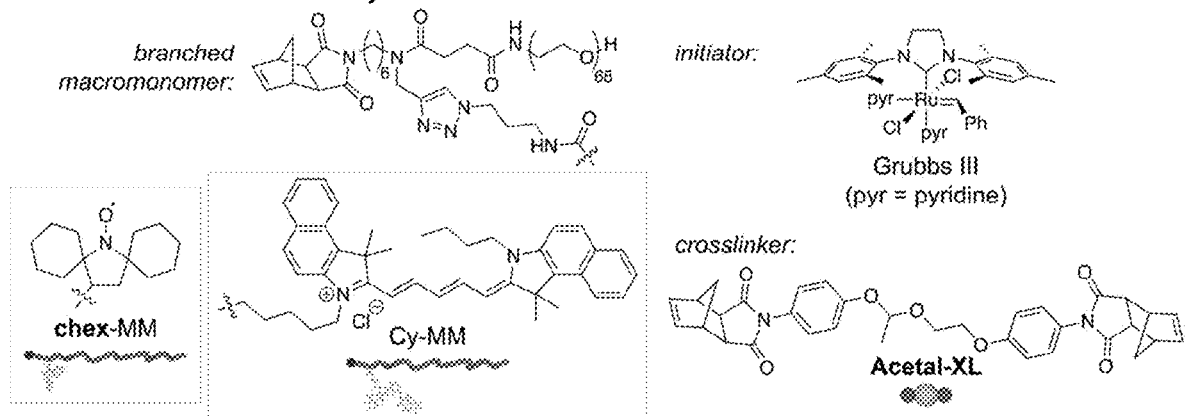
FIGS. 1A-1B show chemical structures of BASP components (FIG. 1A) and the general brush-first ROMP procedure (FIG. 1B). Branched MMs chex-MM and Cy-MM are combined in the ratio j:0.01j. This combination of MMs is exposed to 1.0 equivalents of Grubbs III initiator to produce a living bottlebrush with an average degree of polymerization (DP)=j+0.01j=m. N equivalents of Acetal-XL is then added (in aliquots of 5 eq. Acetal-XL every 5 minutes) to provide the final BASP-ORCA. The properties of the BASP-ORCAs are defined by their m and N values (see FIG. 15).

One of the most common ways to increase the relaxivity of MRI contrast agents (including nitroxides) involves attaching them to a rigid macromolecular scaffold. For example, Rajca et al., appended a spirocyclohexyl nitroxide derivative ("chex")[69] to the surface of dendrimers to produce chex-dendrimer ORCAs where the per-chex $r_1$ was 0.42 $mM^{-1}s^{-1}$ compared to $r_1$=0.14 $mM^{-1}s^{-1}$ for the model nitroxide 3-carboxy-2,2,5,5-tetramethyl-1-pyrrolidinyloxy (3-CP). In another study, chex was appended to the core of PEGylated branched-bottlebrush polymers.[70] The resulting polymers had a per-chex $r_1$ of 0.32 $mM^{-1}s^{-1}$, which was approximately 50% greater than the chex-macromonomer used to synthesize these polymers (chex-MM, FIG. 1A). In this system, $r_2$ also increased from 0.30 $mM^{-1}s^{-1}$ for chex-MM to 0.82 $mM^{-1}s^{-1}$ for the chex-bottlebrush polymer, thus demonstrating that increasing the macromolecular size and chex density leads to increases in both $r_1$ and $r_2$, with a greater increase in $r_2$. In an effort to further increase these relaxivity values, the aim was to incorporate chex into the BASP macromolecules. Moreover, it was hypothesized that BASPs could provide enhanced nitroxide stability potentially making tumor imaging in vivo possible. The control and robustness of BASP synthesis would enable the scalable production of BASP-ORCAs with optimal sizes for tumor accumulation.

Figure 1B:
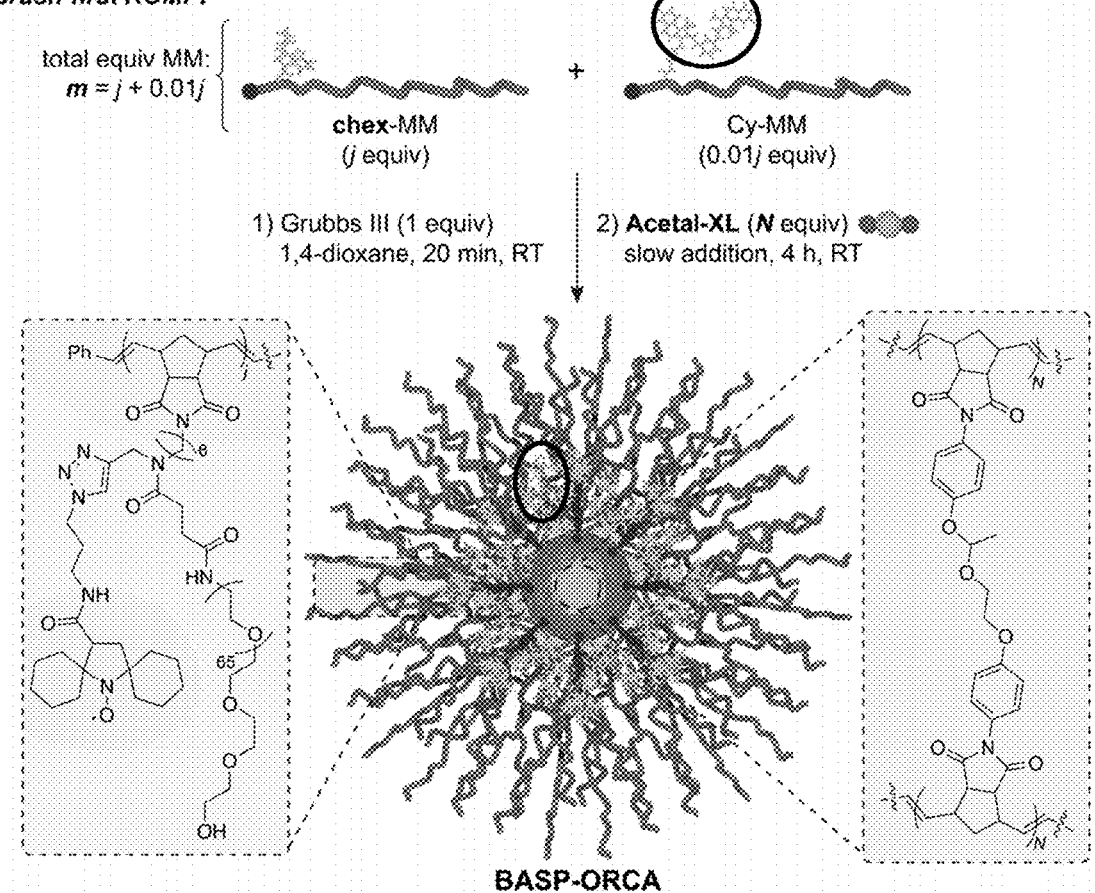

BASP-ORCAs were synthesized following the brush-first ring-opening metathesis polymerization (ROMP) strategy (FIGS. 1A-1B).[71,72] Norbornene-based branched macromonomers (MMs, FIG. 1A) featuring 3 kDa (PEG) and either chex (chex-MM) or Cy5.5 dye (Cy-MM, FIG. 1A) were copolymerized by exposure to Grubbs $3^{rd}$ generation bis-pyridine initiator[73] (Grubbs III, FIG. 1A; reaction stoichiometry: j equivalents chex-MM: 0.01j Cy-MM: 1.0 Grubbs III) for 30 minutes (FIG. 1B). The resulting living bottlebrush polymers with an average degree of polymerization (DP) of: ~j+0.01j=m were crosslinked via slow addition of N equivalents of bis-norbornene acetal crosslinker (Acetal-XL, FIG. 1A) directly to the reaction mixture to generate the desired BASP-ORCA (FIG. 1B). With this method, the BASP-ORCA size is determined by the MM:Grubbs III:Acetal-XL ratios (i.e., m and N values). Much less Cy-MM (0.01j) relative to chex-MM (j) was used to bridge the difference in concentration requirements between MRI (mM to μM) and NIRF (nM to pM).

To identify optimal conditions for the synthesis of BASP-ORCAs with narrow size distributions within the range of ~25-40 nm, as well as high water solubility and relaxivity, m and N values from 5-10 and 15-30, respectively were screened (see FIG. 15). Gel permeation chromatography (GPC) revealed nearly quantitative MM-to-bottlebrush conversion as well as ≥85% bottlebrush-to-BASP conversion for all m and N values (FIGS. 7A-7B). The NP diameters as determined by dynamic light scattering (DLS) and transmission electron microscopy (TEM) ranged from ~28 to ~49 nm (see FIG. 15). A representative TEM image for the m=7.07 and N=20 BASP-ORCA (referred to as BASP-ORCA1) is provided in FIG. 2A. The hydrodynamic diameter ($D_h$) of this particle was 31±4 nm, which is suitable for extended in vivo circulation and tumor accumulation.

Characterization of BASP-ORCA magnetic properties

Electron paramagnetic resonance spectroscopy (EPR) was used to confirm the presence of chex in BASP-ORCAs, as well as to study the chex environment in BASP-ORCA1. The spin concentrations were ≥85% for all BASP-ORCAs. The height-normalized EPR spectra for BASP-ORCA1 and chex-MM are shown in FIG. 2B. The spectrum for BASP-ORCA1 is significantly broader than chex-MM, which is consistent with the larger and more rigid BASP nanostructure where the chex molecules are bound at the dense interface between the acetal crosslinker core and the PEG shell (FIGS. 1B and 2B). The BASP-ORCA1 spectrum was simulated using the procedure developed by Budil and Freed[74], which allows for characterization of the chex mobility in terms of the correlation time for rotational diffusion (τ). The spectrum was best fitted by superimposing two computed components (FIGS. 9A-9D): 22% corresponded to a relatively fast-moving nitroxide with τ=0.2 ns while 78% corresponded to a very slow-moving nitroxide with τ=10.0 ns. The faster-moving component likely corresponds to nitroxides that are furthest from the BASP-ORCA1 acetal core (FIG. 1B), while the slow-moving component corresponds to nitroxides that are close to and/or entangled within the rigid acetal core. Notably, the τ of 10.0 ns measured for the slow component in BASP-ORCA1 is very large, which suggests that the majority of chex molecules are in a rigid environment. For comparison, in the previously reported chex-dendrimer ORCAs, TEMPO-labeled bottlebrush polymers, and BASPs, the largest τ measured was ~1 ns.

Next, the longitudinal ($r_1$) and transverse ($r_2$) relaxivities of these BASP-ORCAs were evaluated using a Bruker 7 T MRI scanner. The per-chex $r_1$ values as a function of m and N (FIG. 15) ranged from 0.27-0.53 $mM^{-1}s^{-1}$; they were not significantly increased compared to Rajca's chex-dendrimer and the chex-bottlebrush polymers. However, the per-chex $r_2$ values ranged from 2.90-7.40 $mM^{-1}s^{-1}$, which is ~3.5-~9.0-fold greater than the per-chex $r_2$ in the chex-bottlebrush polymers and ~17-~44-fold greater than 3-CP (FIG. 15). BASP-ORCA1 displayed a per-chex $r_2$ value of 4.67 $mM^{-1}s^{-1}$. Though this value was not the highest that was measured, BASP-ORCA1 was selected because it offered the best balance of high relaxivity, solubility (approximately 50 mg/mL, FIG. 15), and size for translation to biological studies. Given the number-average molar mass of BASP-ORCA1 as determined by gel permeation chromatography and static light scattering ($M_n$=4.75×10$^5$ g/mol, D=1.32), it can be estimated that each BASP-ORCA1 particle contains an average of 92 chex groups. Based on this number, the estimated average molecular $r_1$ and $r_2$ values for BASP-ORCA1 are 37.6 $mM^{-1}s^{-1}$ and 428.8 $mM^{-1}s^{-1}$, respectively, which are greater than those for the commonly used FDA-approved Gd-based contrast agent Magnevist ($r_1$=3.1 $mM^{-1}s^{-1}$ and $r_2$=5.4 $mM^{-1}s^{-1}$ at 7 T) and iron-based NPs such as Feraheme ($r_1$=3.1 $mM^{-1}s^{-1}$ and $r_2$=68 $mM^4s^{-1}$ at 7 T).[75,76,77,78] The $r_2/r_1$ ratio for BASP-ORCA1 is approximately one-half that of Feraheme. Thus, BASP-ORCA1 should provide effective $T_2$-weighted MRI contrast enhancement.

MR phantom images of phosphate-buffered saline (PBS) solutions of BASP-ORCA1, chex-MM, and the previously reported chex-bottlebrush polymer at various chex concentrations (from 1 mM-4 mM chex) as well as a PEG-based BASP that lacks chex (at equivalent concentrations by mass as BASP-ORCA1) are provided in (FIG. 2C), along with images for "blank" PBS buffer. The $T_1$-weighted images for BASP-ORCA1, chex-MM, and chex-bottlebrush polymer are not obviously different while the $T_2$-weighted images clearly show a large decrease in signal for BASP-ORCA1 as concentration increases. The PEG-BASP with no chex shows no change in contrast as a function of concentration, which confirms that chex is required to observe any changes in image contrast.

The data presented above demonstrate that the high nitroxide density of BASP-ORCA1, which is a consequence of its unique crosslinked multi-layer nanostructure, affords an increased magnetization capability for $r_2$ enhancement. This finding is consistent with reports where nitroxides are utilized as magnetic catalysts for outer-sphere relaxation processes.[79,80,81] Most importantly, the exceptionally high $r_2$ of BASP-ORCA1 overcomes one of the major limitations of nitroxide-based contrast agents: inherently low contrast.

Ascorbate Quenching Kinetics of BASP-ORCAs

Figure 3A:
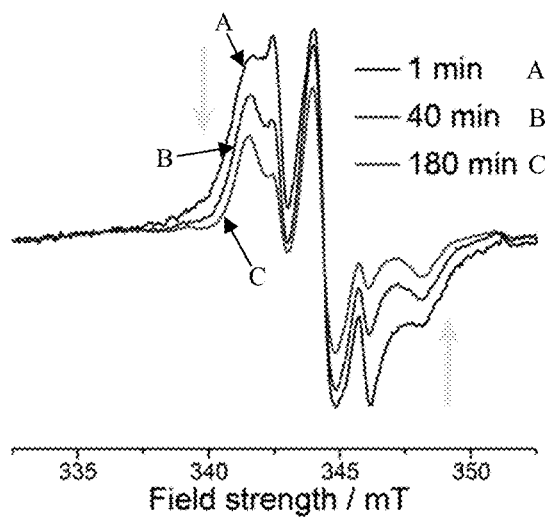
FIGS. 3A-3C are EPR spectra for BASP-ORCA1 at 1 minute, 40 minutes, and 180 minutes following exposure to 20 equivalents of sodium ascorbate (Asc) per nitroxide moeity (FIG. 3A), ascorbate reduction kinetics for BASP-ORCA1, chex-bottlebrush, and chex-MM (FIG. 3B), and Cy5.5 emission at 700 nm in response to Asc and glutathione (GSH) (FIG. 3C).
Figure 3B:
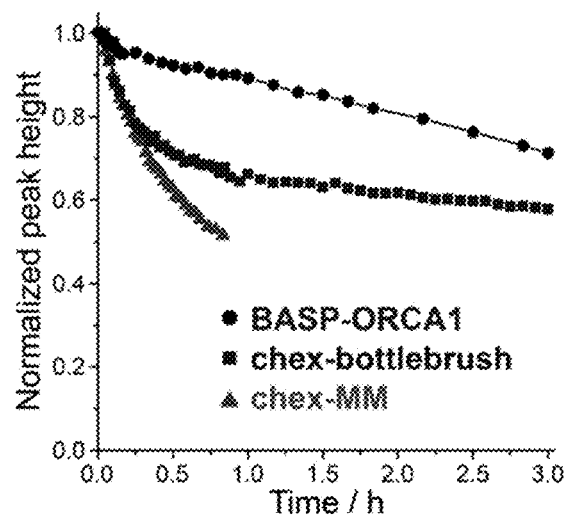

As discussed above, nitroxide-based ORCAs typically suffer from rapid reduction to diamagnetic hydroxylamines under biologically relevant conditions. Amongst the many potential biological reducing agents, ascorbate (Asc) is known to play a major role in in vivo nitroxide reduction,[82,83] and Asc-induced reduction can be amplified by glutathione (GSH). It was hypothesized that the rigid chex environment in the BASP-ORCAs could help to lower the rate of chex reduction. To test this hypothesis, EPR spectra for BASP-ORCA1 at various times were collected following exposure to 20 equivalents of Asc and 20 equivalents of GSH per nitroxide (both reagents were present in 10 mM concentrations). EPR spectra collected 1 minute, 40 minutes, and 180 minutes after exposure to these conditions are provided in FIG. 3A; the reduction in peak height as a function of time is indicative of nitroxide reduction. The normalized peak height of the EPR spectra are plotted versus time in FIG. 3B. Reduction kinetics data for the previous chex-bottlebrush polymers and chex-MM are provided for comparison. In contrast to the chex-bottlebrush and chex-MM samples, which both display an initial rapid chex reduction phase in the first hour, the reduction of chex in BASP-ORCA1 was significantly retarded with nearly 85% remaining after 1 hour, and 70% remaining after 3 hours (compared to 65% and 57%, respectively, for the chex-bottlebrush). Based on the integrated peak heights as a function of time, the second-order rate constants for BASP-ORCA1 reduction in the initial (first 10 minutes) and late (>1 hour) stages of the reduction process were calculated: $k_{early}$=0.0376 $M^{-1}s^{-1}$ and $k_{late}$ 0.00672 $M^{-1}s^{-1}$) (Table 2). Simulation revealed that the EPR spectra collected during the reduction process still consisted of a "fast" and a "slow" component (FIGS. 9A-9D). Interestingly, T for the "fast" component remained constant at 0.2 ns, while T for the "slow" component became increasingly larger with time (11.0 ns at 40 minutes and 13.2 ns at 180 minutes). Therefore, even after 3 hours there persists an extremely reduction resistant and slow moving nitroxide population, which suggests that BASP-ORCAs could be used for tumor MRI over longer timescales than have been possible with previous nitroxide contrast agents (vide infra).

Nitroxide Reduction Kinetics

TABLE 2

Kinetics of the reduction of nitroxides with 20-fold molar excess of ascorbate (Asc) and 0-25-fold molar excess of glutathione (GSH). Numerical fits to pseudo-first order rate equation (k') peak height (PH) or integrated peak height (IPH) of the low-field EPR line.

| Compd | Run No. | Run Label | Data used | Nitrox Conc. (mM) | Asc. Conc. (mM) | GSH Conc. (mM) | Initial Kinetics (<1 h) Range of fits | k' × 10$^4$ (s$^{-1}$) | R$^2$ | k × 10$^4$ (M$^{-1}$ s$^{-1}$) | Avg k × 10$^4$ (M$^{-1}$ s$^{-1}$) | Late Kinetics (>1 h) Range of fit (h) | k' × 10$^4$ (s$^{-1}$) | R$^2$ | k × 10$^4$ (M$^{-1}$ s$^{-1}$) |
|---|---|---|---|---|---|---|---|---|---|---|---|---|---|---|---|
| BASP-ORCA1$^a$ | 1 | JP1191 | IPH | 0.5 | 10 | 10 | <1000 | 3.294 | 0.8795 | 329.4 | 366 ± 25 | 1.2-2.8 | 0.672 | 0.9923 | 67.2 |

TABLE 2-continued

Kinetics of the reduction of nitroxides with 20-fold molar excess of ascorbate (Asc) and 0-25-fold molar excess of glutathione (GSH). Numerical fits to pseudo-first order rate equation (k') peak height (PH) or integrated peak height (IPH) of the low-field EPR line.

| Compd | Run No. | Run Label | Data used | Nitrox Conc. (mM) | Asc. Conc. (mM) | GSH Conc. (mM) | Initial Kinetics (<1 h) Range of fits | k' × $10^4$ ($s^{-1}$) | $R^2$ | k × $10^4$ ($M^{-1} s^{-1}$) | Avg k × $10^4$ ($M^{-1} s^{-1}$) | Late Kinetics (>1 h) Range of fit (h) | k' × $10^4$ ($s^{-1}$) | $R^2$ | k × $10^4$ ($M^{-1} s^{-1}$) |
|---|---|---|---|---|---|---|---|---|---|---|---|---|---|---|---|
| | | | IPH*[a] | | | | | 3.40 | 0.9948 | 339.7 | 334 ± 55 | | 0.586 | 0.9994 | 58.6 |
| | | | PH | | | | | 0.836 | 0.8721 | 83.6 | | | 0.297 | 0.9943 | 29.7 |
| | 2 | JP1190 | IPH | 0.5 | 10 | 10 | 115-595 | 3.712 | 0.7664 | 371.2 | | | | | |
| | | | IPH*[a] | | | | | 3.408 | 0.9910 | 340.8 | | | | | |
| | | | PH | | | | | 3.377 | 0.2923 | 33.77 | | | | | |
| | | JP1189 | IPH | 0.5 | 10 | 10 | 113-613 | 3.828 | 0.7646 | 382.8 | | | | | |
| | | | IPH*[a] | | | | | 3.238 | 0.9863 | 323.7 | | | | | |
| | | | PH | | | | | 5.07 | 0.3068 | 50.7 | | | | | |
| | 4 | JP1188 | IPH | 0.5 | 10 | 10 | 126-603 | 3.818 | 0.5387 | 381.8 | | | | | |
| | | | IPH*[a] | | | | | 3.311 | 0.9938 | 331.1 | | | | | |
| | | | PH | | | | | 5.072 | 0.3366 | 50.72 | | | | | |
| chex-bottle-brush | 1 | YW982 | IPH | 0.5 | 10 | 5.0 | 177-897 | 3.27 | 0.9633 | 327.0 | 306[b] | | | | |
| | | | PH | | | | | 3.42 | 0.9702 | 342.0 | 308[b] | | | | |
| | 2 | YW983 | IPH | 0.5 | 10 | 5.0 | 396-1019 | 2.85 | 0.9520 | 285.0 | | 1.1-2.8 | 0.416 | 0.9216 | 41.6 |
| | | | PH | | | | | 2.73 | 0.9895 | 273.0 | | | 0.386 | 0.9938 | 38.6 |
| chex-bottle-brush | 1 | YW981 | IPH | 0.5 | 10 | 0.0 | 251-851 | 3.05 | 0.9439 | 305.0 | 296[b] | | | | |
| | | | PH | | | | | 2.41 | 0.9808 | 241.0 | 254[b] | | | | |
| | 2 | YW985 | IPH | 0.5 | 10 | 0.0 | 278-878 | 2.86 | 0.9145 | 286.0 | | 1.3-2.8 | 0.243 | 0.8838 | 24.3 |
| | | | PH | | | | | 2.68 | 0.9775 | 268.0 | | | 0.196 | 0.9735 | 19.6 |
| chex-dendrimer | 1 | JP609 | IPH | 0.5 | 10 | 0.0 | 90-390 | 6.20 | 0.6609 | 620.0 | 603 ± 123 | 0.8-2.8 | 0.301 | 0.6847 | 30.1 |
| | | | PH | | | | | 6.17 | 0.9718 | 617.0 | 579 ± 59.6 | | 0.354 | 0.9663 | 35.4 |
| | 2 | JP610 | IPH | 0.5 | 10 | 0.0 | 115-415 | 7.18 | 0.6743 | 718.0 | | | | | |
| | | | PH | | | | | 6.09 | 0.9336 | 609.0 | | | | | |
| | 3 | JP611 | IPH | 0.5 | 10 | 0.0 | 126-426 | 4.72 | 0.7984 | 472.0 | | | | | |
| | | | PH | | | | | 5.10 | 0.9915 | 510.0 | | | | | |
| 3-CP | 1 | JP899 | IPH | 0.2 | 4.0 | 5.0 | <600 | 2.435 | 0.9997 | 608.8 | 608.0 ± 4.2 | | | | |
| | | | PH | | | | | 2.361 | 0.9990 | 590.3 | 602.6 ± 25 | | | | |
| | 2 | JP8100 | IPH | 0.2 | 4.0 | 5.0 | <600 | 2.438 | 0.9997 | 609.6 | | | | | |
| | | | PH | | | | | 2.410 | 0.9996 | 602.4 | | | | | |
| | 3 | JP1101 | IPH | 0.2 | 4.0 | 5.0 | <600 | 2.423 | 0.9998 | 605.6 | | | | | |
| | | | PH | | | | | 2.461 | 0.9996 | 615.2 | | | | | |
| 3-CP | 1 | JP460 | IPH | 0.2 | 4.0 | 0.0 | <3600 | 2.547 | 0.9996 | 636.8 | 625 ± 22 | | | | |
| | | | PH | | | | | 2.504 | 0.9949 | 636.0 | 611 ± 44 | | | | |
| | 2 | JP461 | IPH | 0.2 | 4.0 | 0.0 | <3600 | 2.498 | 0.9975 | 624.5 | | | | | |
| | | | PH | | | | | 2.396 | 0.9949 | 599.0 | | | | | |
| | 3 | JP462 | IPH | 0.2 | 4.0 | 0.0 | <3600 | 2.459 | 0.9999 | 614.8 | | | | | |
| | | | PH | | | | | 2.389 | 0.9961 | 597.3 | | >1 | 1.18 | 0.9952 | 295 |

[a]For BASP-ORCA1, double integration of entire EPR spectra gave initial rate constant k = 449 ± 23 $M^{-1}s^{-1}$, which is somewhat larger than the integrated peak height (IPH) value, k = 366 ± 25 $M^{-1}s^{-1}$;
IPH* is the integrated peak height for the center line of the EPR spectrum.
[b]For ORCA-Fluor, initial second order rate constants from 4 kinetic runs using 0-10 equivalents of GSH, k = 301 ± 20 and 281 ± 43 $M^{-1}s^{-1}$ for baseline corrected IPH and PH data. Data for chex-bottlebrush,[90] data for chex-dendrimer (baseline corrected) and late kinetics for 3-CP with Asc only, data for 3-CP with 20 equivalents of Asc and 25 equivalents of GSH,[92] and data for 3-CP with Asc only[93] were reported elsewhere.

Fluorescence Properties of BASP-ORCAs

As noted above, Cy5.5 was also incorporated into these BASP-ORCAs (see FIG. 10 for BASP-ORCA1 absorption and emission spectra confirming the presence of Cy5.5) in order to simultaneously use NIRF as an imaging modality for comparison to MRI. Nitroxides are well-known to quench fluorescence via catalysis of non-emissive photophysical processes such as intersystem crossing. This quenching requires close interaction between the nitroxide and the fluorophore; the systems with the greatest quenching typically feature the nitroxide directly linked to the fluorophore via π bonds (i.e., electronic conjugation).[84,85,86] Given the fact that chex and Cy5.5 are incorporated into BASP-ORCAs via two different macromonomers, and noting the limited mobility of chex in these nanoparticles, it was reasoned that Cy5.5 quenching would be minimal; therefore, Cy5.5 emission could be used as a fairly constant descriptor of particle concentration regardless of the extent of chex reduction.

Figure 3C:
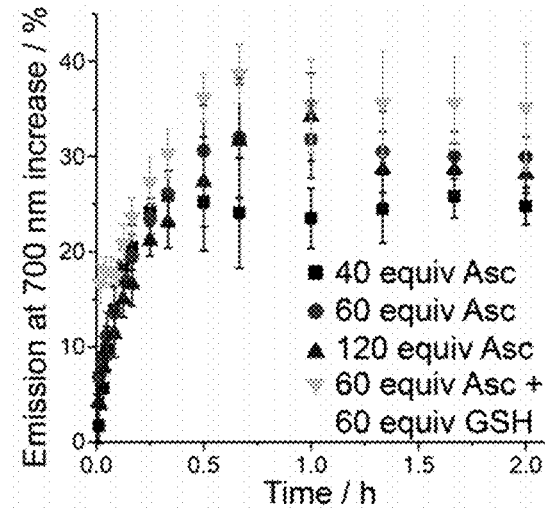

To test this hypothesis, BASP-ORCA1 was exposed to a large excess of Asc (40 to 120 equivalents to chex) in water, and monitored the resulting Cy5.5 emission. In agreement with the expectation, only a 25±2% to 30±2% increase in fluorescence emission was observed (FIG. 3C). Moreover, addition of GSH (60 equivalents) as a co-reductant along with 60 equiv. of Asc gave only a 35±7% increase in fluorescence. Taken together, these data suggest that Cy5.5 fluorescence is only minimally quenched by chex in BASP-ORCA1. For comparison, exposure of the previously reported chex-bottlebrush polymer containing Cy5.5 to excess Asc or Asc+GSH led to 119±5% and 250±5% increases in fluorescence, respectively. Notably, the time required to achieve a fluorescence plateau varied significantly between BASP-ORCA1 (approximately 40 minutes) and the chex-bottlebrush polymer (a few minutes). Collectively, these data suggest that the BASP nanostructure provides greater steric shielding and isolation of chex and Cy5.5 compared to the analogous bottlebrush polymer.

In Vitro Cytotoxicity and In Vivo Gross Toxicity, Pharmacokinetics (PK), and Biodistribution (BD) of BASP-ORCA1 in Non-Tumor Bearing Mice Motivated by BASP-ORCA1's unprecedented combination of properties, which include nanoscopic size ($D_h$=31±4 nm) and narrow size distribution, good water solubility, slow reduction kinetics, and exceptionally high $r_2$ relaxivity for an organic contrast agent, next the performance of this nanomaterial in biological assays was investigated. As discussed above, one potential advantage of ORCAs is their low toxicity. To investigate the toxicity of BASP-ORCA1, first in vitro human umbilical vein endothelial cell (HUVEC) and HeLa cell viability assays were conducted. In these assays, the cells were incubated with varied concentrations of BASP-ORCA1 for 72 h. Cell viability was determined by the CellTiter Glo assay (FIG. 11). The half-maximal inhibitory concentration ($IC_{50}$) of BASP-ORCA1, i.e., the concentration that led to 50% cell death, was 1.5 mg/mL (280 µM chex) and 4.5 mg/mL (830 µM chex) in HUVEC and HeLa cells, respectively. These results confirm that BASP-ORCA1 induces negligible in vitro cytotoxicity at practical concentrations. Next, the in vivo gross toxicity of BASP-ORCA1 was assessed. Healthy BALB/c mice were administered increasing doses (from 5 to 30 mg or 0.2 to 1.5 g/kg, respectively) of BASP-ORCA1 via tail vein injection. The animal body masses and behaviors were monitored over the course of 30 days. Loss of ≥10% body mass is generally considered to be a sign of unacceptable toxicity.[87,88] As shown in FIG. 12, even the highest dose of BASP-ORCA1 (administered to n=4 animals) induced no significant decrease in body mass, which suggests that these particles are well-tolerated up to their solubility-limiting dose.

The pharmacokinetics (PK) and biodistribution (BD) of BASP-ORCA1 were monitored in healthy, non-tumor bearing BALB/c mice (n=3) using NIRF imaging (IVIS, Cy5.5$\lambda_{ex}/\lambda_{em}$=640/700 nm). For PK analysis, blood samples were collected via cardiac puncture at various time points from 1 hour to 48 hours. Percent injected dose was plotted as a function of time (FIG. 13A). As is common for spherical nanoparticles, BASP-ORCA1 exhibited a two-phase clearance behavior, with an early distribution phase of ~6 hours, followed by a steady elimination phase. Fitting the data presented in FIG. 13A with a standard two-compartment model yielded a blood compartment half-life for BASP-ORCA1 of 10 hours.[89] This long half-life is attributed to the nanoscale size of BASP-ORCA1, which limits renal clearance, and its PEGylated corona, which minimizes protein absorption and macrophage uptake. Consistent with these results and a plethora of studies on PEGylated nanoparticles, BD analysis revealed that a majority of BASP-ORCA1 accumulated in the liver, with increasing accumulation over 72 hours (FIG. 13B). Less, but significant, accumulation in the kidney and negligible accumulation in other tissues was observed (Note: fluorescence in extracted lung tissue is attributed to a high concentration of BASP-ORCA1 in the blood). Notably, fluorescence images of fecal samples (FIG. 13C) suggest that BASP-ORCA1 is ultimately cleared from the body via excretion.

BASP-ORCA1 BD in Tumor-Bearing Mice

Figure 4A:
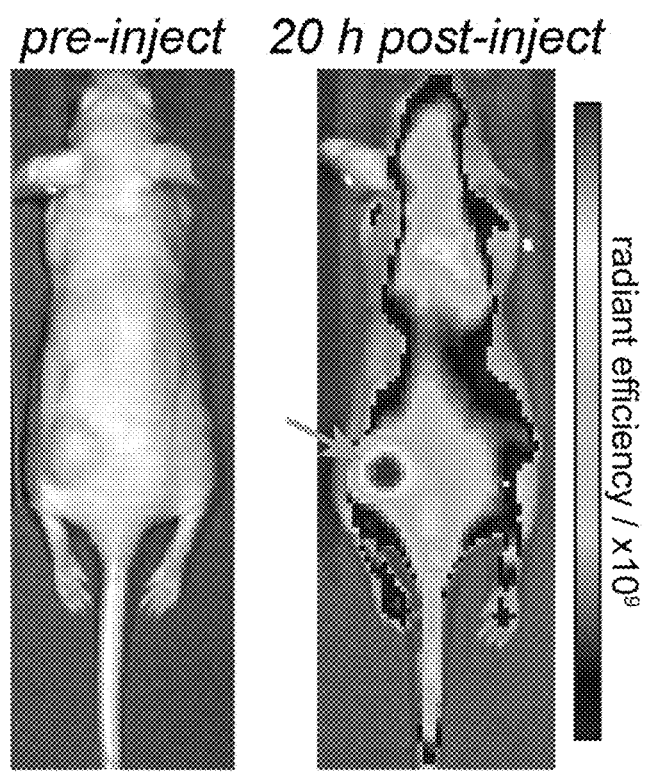
FIGS. 4A-4B show in vivo NIRF images of NCR nude mouse before and 20 hours after injection of BASP-ORCA1 (FIG. 4A) and ex vivo NIRF images of selected organs (FIG. 4B). Units of radiant efficiency.
Figure 4B:
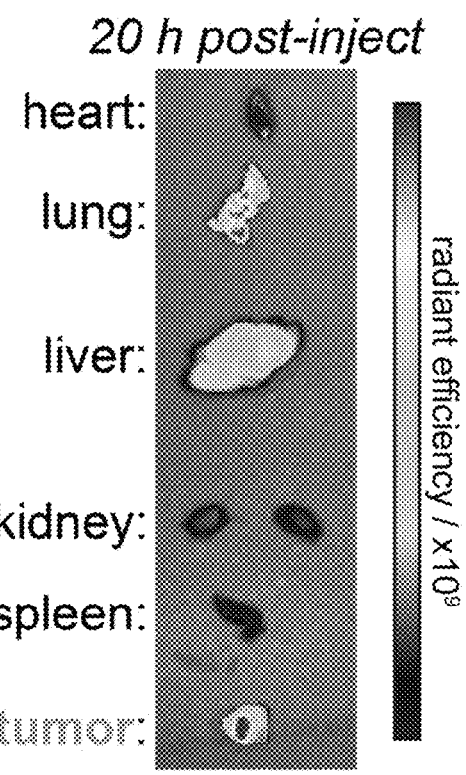

Given the long circulation of BASP-ORCA1, it was hypothesized that this particle would passively accumulate in subcutaneous tumors following systemic injection. To test this hypothesis, a tumor model was established via subcutaneous injection of a mixture of 2.0×10⁶ lung carcinoma cells (A549, ATCC), Matrigel, and PBS buffer into a hind flank of NCR-NU mice (n=4). When the average tumor volume was ~1 cm, BASP-ORCA1 was administered at a dose of 0.23 mmol chex/kg via tail vein injection. The mice were imaged 20 hours after administration. This choice of imaging time strikes a balance between allowing for sufficient tumor accumulation while limiting the extent of chex reduction in vivo. NIRF images indicated substantial tumor accumulation of BASP-ORCA1, which is consistent with other reports for PEGylated nanoparticles of similar size including the related drug-conjugated BASPs (FIG. 4A). Ex vivo BD data were consistent with the studies on non-tumor bearing BALB/c mice (i.e., liver accumulation and persistence in blood, FIGS. 13A and 13B) with the addition of significant tumor accumulation (FIG. 4C and FIG. 14).

In Vivo MRI and NIRF Imaging with BASP-ORCA1

The low toxicity, long circulation half-life, and tumor accumulation of BASP-ORCA1, along with its exceptional chex stability and relaxivity, suggested that this particle could be suitable for MRI of tumors following systemic injection and accumulation; a feat that has not yet been reported with ORCAs. Two groups of A459 tumor-bearing NCR-NU mice were administered different doses of BASP-ORCA1 via tail-vein injection: the "low dose" group (n=3) received 0.16 s mmol chex/kg (0.8 g BASP-ORCA1/kg) while the "high dose" group (n 4) received 0.23 mmol chex/kg (1.2 g BASP-ORCA1/kg). The mice were anaesthetized and MR images were collected at various time points: 12 hours, 16 hours, and 20 hours post-injection for the low dose group and 20 hours post-injection for the high dose group. The images from each time point were compared to images collected before BASP-ORCA1 injection. FIG. 5A shows $T_2$-weighted images for a selected mouse from the low dose group imaged before BASP-ORCA1 injection (top row of images) and 20 hours (bottom row of images) after BASP-ORCA1 injection; from left-to-right the images correspond to progressive slices of the same animal in the z-axis with the tumor observed on the bottom right of each image. FIG. 5B shows an analogous set of images for a selected mouse from the high dose group. Contrast differences between the pre-injection and post-injection images can be observed at both dose levels, with greater contrast observed in the high dose animal. Whole animal images similarly revealed a clear difference in tumor contrast (FIG. 5C, arrows).

The percent negative contrast enhancement (i.e., signal reduction) before and after BASP-ORCA1 administration was quantified by image analysis (FIG. 5D). Signal reductions ranging from 14±2% to 16±2% (P≤0.05) were observed for the 12 hour to 20 hour time points in the low dose group (FIG. 5D, low dose bars). In the high dose group, a 24±2% (P≤0.001) signal reduction was observed 20 hours after BASP-ORCA1 administration (FIG. 5D, high dose right bar). The clear BASP-ORCA1 dose-response effect suggests that the observed contrast differences between pre- and post-injection are due to accumulation of BASP-ORCA1 in the tumors. Keeping in mind that MRI phantoms revealed no observable contrast enhancement for PEG-BASPs that lack chex (FIG. 2C), these MRI data imply that 20 hours following injection there is a sufficient concentration of non-reduced chex (i.e., chex radicals) present on the BASP-ORCA1 to impart contrast. To confirm the presence of chex radicals in the tumors, the same mice that were imaged by MRI were sacrificed 21 hours after BASP-ORCA1 administration and their tissue homogenates and blood were analyzed by EPR spectroscopy (FIG. 6A). From these spectra, the radical concentration per g protein in each tissue sample, the latter obtained via a bicinchoninic acid assay (BCA), of the tissue homogenate, was evaluated and normalized by the radical concentration per g protein in muscle tissue (FIG. 6B). In agreement with the MRI data, the concentration of free radicals in the tumor was quite high 22 hours after BASP-ORCA1 injection; the measured value of 0.25 µmol ±0.04 chex/g of protein corresponds to 4.5% of the injected dose of chex radicals (Note: this value does not include any chex radicals that were reduced, and thus the percent injected dose of BASP-ORCA1 in the tumor is likely larger than 4.5%). Moreover, consistent with the in vivo NIRF imaging results (vide supra), relatively high radical concentrations were observed in the liver and kidney, which suggests that the clearance of BASP-ORCA1 proceeded mostly through these organs. Notably, the murine liver contains a high concentration of Asc (millimolar range); the observation of radicals in the liver 22 hours after injection is further evidence of the extremely stable nature of the chex units in βASP-ORCA1 (Note: in the previous chex-bottlebrush polymers, there was very little chex radical in the liver following 30 minutes and none after 24 hours). A high chex concentration was also observed in the heart, which is in accord with a long blood compartment half-life and is consistent with the PK data obtained by NIRF imaging. Finally, NIRF imaging of these homogenates provided fluorescence radiant efficiencies that were in good agreement with the spin concentrations (FIG. 6B), which suggests that the chex radicals and Cy5.5 dyes are still co-localized within the BASP-ORCA1 construct 22 hours after injection. Unlike the previous chex-bottlebrush polymers, which displayed dramatic increases in fluorescence as chex was reduced, the signal uniformity offered by BASP-ORCA1 provides for straightforward multi-modal confirmation of BD.

BASP-ORCA1 is the first nitroxide MRI contrast agent capable of providing significant contrast 20 hours after injection, which is a testament to its unique structural features that combine optimal size for tumor accumulation with a high nitroxide density and stability. To set these results in context, the data outlined herein was compared to recent literature examples of MRI-contrast agents the rely on metals to achieve tumor imaging following systemic administration. For example, Kataoka and coworkers recently reported on a new class of Gd-based nanoparticles ($T_1$ contrast agents) for MRI of tumors. In their study, a ~40% contrast enhancement (at 0.05 mmol Gd/kg iv dose) was observed plateauing 4 hours following injection into mice bearing subcutaneous C26 tumors. Notably, commercially available Gd-DTPA, which is a small molecule, exhibited negligible contrast enhancement (at 0.23 mmol Gd/kg iv dose) after 4 hours. This example highlights the importance of a nanoparticle system for extended circulation and tumor imaging, though the impact of Gd nanoparticle accumulation in tissues would need to be addressed prior to clinical translation. In another example, the same group reported novel Fe-based nanoparticles ($T_2$ contrast agents) for tumor imaging in a similar murine model (subcutaneous C26 tumors). Here, an approximately 25% contrast difference was observed 24 hours following intravenous administration of 0.45 mg Fe/kg. Notably, less than 10% contrast enhancement was observed using commercially available Resovist® (at 0.45 mg Fe/kg intravenous dose).Error Bookmark not defined. It should be noted that the instrument parameters used to obtain $T_2$-weighted images in this work were similar to those used in the studies described herein; thus, these results for BASP-ORCA1 are on par with recently reported nanoparticle MRI contrast agents that rely on metals to achieve contrast.

Conclusion

In conclusion, a nitroxide-nanoparticle MRI contrast agent -BASP-ORCA1—that enables simultaneous MRI and NIRF imaging in vivo over timescales suitable for tumor imaging following systemic injection was developed herein. BASP-ORCA1 addresses the two major challenges that have historically limited nitroxide-based organic radical contrast agents for MRI: low relaxivity and poor stability. These functions were made possible by the brush-arm star polymer (BASP) nanostructure, which enables the placement of chex nitroxides at the interface between a rigid poly(acetal) core and a hydrophilic PEG shell. Altogether, BASP-ORCA1 displayed unprecedented per-nitroxide and per-molecule transverse relaxivities for organic radical contrast agents, exceptional stability, high water solubility, low in vitro and in vivo toxicity, and a long blood compartment half-life. These features combined to facilitate the imaging of subcutaneous tumors in mice 20 hours after tail-vein injection, providing contrast enhancements on par with commercial and literature examples of metal-based contrast agents. This work suggests that organic radicals can be viable alternatives to metal-based MRI contrast agents, and sets the stage for the development of theranostic systems that combine organic radical contrast agents with therapeutic payloads to achieve simultaneous tumor imaging and drug delivery without concerns over long-term accumulation of metals.

Materials, General Methods, and Instrumentation

All reagents were purchased from commercial suppliers and used without further purification unless stated otherwise. Grubbs 3rd generation bispyridyl catalyst,[73] macromonomers (MMs) chex-MM,[2] Cy-MM,[90] PEG-MM and cross-linker Acetal-XL were prepared according to literature procedures. Size exclusion chromatography (SEC) analyses were performed on an Agilent 1260 Infinity setup with two Shodex KD-806M columns in tandem and a 0.025 M LiBr DMF mobile phase run at 60° C. The differential refractive index (dRI) of each compound was monitored using a Wyatt Optilab T-rEX detector, and the light scattering (LS) signal was acquired with a Wyatt Dawn Heleos-II detector. Column chromatography was carried out on silica gel 60F (EMD Millipore, 0.040-0.063 mm).

Dynamic light scattering (DLS) measurements were performed using a Wyatt Technology Mobius DLS instrument. Samples were prepared at 1.0 mg/mL in either nanopure water (MilliQ), PBS buffer, or 5% glucose solution (in nanopure water). The resulting solutions were passed through a 0.4 µm Nalgene filter (PES membrane) into disposable polystyrene cuvettes, which were pre-cleaned with compressed air. Measurements were made in sets of 10 acquisitions, and the average hydrodynamic diameters were calculated using the DLS correlation function via a regularization fitting method (Dynamics 7.4.0.72 software package from Wyatt Technology).

TEM images were acquired using a FEI Tecnai Multipurpose TEM (G2 Spirit TWIN, 12 kV) at the MIT Center for Materials Science and Engineering. Samples were prepared as follows: 5 µL of a 1.0 mg/mL aqueous solution of BASP-ORCA was pipetted onto a carbon film-coated 200-mesh copper grid (Electron Microscopy Sciences) placed on a piece of parafilm. Next, the solution was carefully absorbed at the base of the droplet using the edge of a Kimwipe, leaving behind the nanoparticles on the TEM grid. The samples were then negatively stained by adding a drop of 2 wt % uranyl acetate (Electronic Microscopy Sciences). After 3 min, the residual uranyl acetate solution was carefully absorbed onto a Kimwipe, and the samples were allowed to dry completely.

Excitation/emission spectra and fluorescence measurements were acquired using a Tecan Infinite® 200 Pro plate reader. Electron Paramagnetic Resonance (EPR) spectra were acquired at the University of Nebraska using a Bruker CW X-band spectrometer equipped with a frequency counter. The spectra were obtained using a dual mode cavity; all spectra were recorded using an oscillating magnetic field perpendicular ($TE_{102}$) to the swept magnetic field. DPPH powder (g=2.0037) was used as a g-value reference.

Relaxivity Measurements by MRI

Phantom MRI data were acquired in a 12 cm outer diameter birdcage transceiver for imaging in a 20 cm bore Bruker 7 T Avance III MRI scanner. Samples at varying concentrations (0 up to 5 mM) in PBS buffer were loaded into the wells of a 384-well clear polystyrene plate (Thermo Scientific Nunc), which had been pre-cut in half to optimally fit the coil. Unused wells were filled with PBS buffer. 2 mm slices were imaged through the samples with the field of view of 5×5 cm and the data matrices were 256×256 points. Longitudinal ($r_1$) and transverse ($r_2$) relaxivity measurements were acquired using multi-spin multi-echo (MSME) sequences (flip angle=180°). $r_1$; TE=12 ms, TR=300, 350, 400, 450, 500, 600, 800, 1000, 1200, 1500, 3000, 5000, 10000 ms. $r_2$; TR=5000 ms, TE=12, 24, 36, 48, 60, 72, 84, 96, 108, 120, 132, 144, 156, 168, 280, 192, 204, 216, 228, 240, 252, 264, 276, 288, 300, 312, 324, 336, 348, 360 ms. Custom routines written in Matlab (Mathworks, Natick, Mass.) were used to reconstruct the images and compute relaxation time constants by fitting image intensity data to exponential decay curves.

Kinetics of Nitroxide Quenching by EPR Spectroscopy

A solution was prepared with ascorbic acid (Asc), sodium phosphates (<30 ppm transition metals), sodium hydroxide and diethylenetriaminepentaacetic acid (DTPA, ~0.1% (mol/mol) to sodium phosphates) at pH 7.4. Reduced L-GSH was then dissolved to provide the Asc/GSH solution. BASP-ORCA solution was prepared in phosphate buffer, which was made from sodium phosphates and DTPA (~0.1% (mol/mol) to sodium phosphates) at pH 7.4. Equal volumes of the freshly prepared 1 mM (in nitroxide) sample solution and 20 mM Asc/GSH solution were combined and vortexed for 6 seconds, and then added to a 2 mm OD EPR tube. Kinetic studies were performed on 0.5 mM nitroxide solution in the presence of 125 mM sodium phosphates, 10 mM Asc, and 10 mM GSH. The peak height of the low-field line of the triplet was measured as a function of time. Microwave power was kept under 6.5 mW and the temperature was controlled at 295 K with a nitrogen flow system.

Computational Analysis of Nitroxide Quenching by EPR Spectroscopy

The EPR spectra are constituted by a "fast" and a "slow" component. From visual inspection, it was clear that the slow component was changing from one to another sample, while the fast one showed an almost equivalent line shape in the three spectra. Therefore, first a computation (program by Budil&Freed[74]) of the fast component to be subtracted from the three spectra to obtain a reliable line shape for the slow components was employed. This succeeded for the fast component shown in FIG. 9A (the subtracted experimental line in black and the computed line is in red). The main parameters used for the computation are shown in the figure and described below. Subtraction of this fast component from the overall spectra produced the three slow components shown in FIGS. 9B, 9C and 9D for 1 min, 40 min, and 180 min, respectively (in FIGS. 9A-9D the spectra are normalized in height). Their computations are shown as well, together with the main parameters used for computation and analysis. The following parameters were calculated.

The $g_{ii}$ components for the coupling between the electron spin and the magnetic field (accuracy from computation±0.0002). The starting values, which were used in previous studies[91] using nitroxide radicals, are 2.009, 2.006, 2.003, for $g_{xx}$, $g_{yy}$, and $g_{zz}$, respectively. It was found that these values worked for the computations of the fast component and for the t=1 minute slow component; however, for computing the slow components of t=40 minutes and 180 minutes it was necessary to decrease the $g_{zz}$ values to 2.0025 and 2.002, respectively. This observation indicated an increased structural anisotropy of the nitroxide labels from 1 minute to 40 minutes to 180 minutes.

The $A_{ii}$ components for the coupling between the electron spin and the nitroxide-nitrogen nuclear spin (accuracy from computation+0.5 G). These parameters increase with an increase in the environmental polarity of the nitroxide. Mainly, as done in previous studies,[91] the $A_{xx}$ and $A_{yy}$ values were maintained constant (6 G) and only $A_{zz}$ was changed. The polarity was found to be slightly lower for the fast component ($A_{zz}$=35 G) than for the slow one ($A_{zz}$=36 G); it was constant for the different slow components.

The correlation time for rotational diffusion of the radical, τ (accuracy from computation ±0.05 ns). This parameter increases with an increase in the local viscosity around the nitroxide group and with a decrease in the rotational mobility of the nitroxide. The local viscosity largely increased (the mobility decreased) from the fast component to the slow ones and it also increased (the mobility decreased) from 1 minute (10 ns) to 40 minutes (11 ns) to 180 minutes (13.2 ns). Notably, by performing a subtraction procedure using the double integrals of the components of the spectra, it was found that the fast component was contained in all the three spectra in almost the same relative percentage, that is, about 20% (the accuracy in this percentage is about 1%).

The line width (accuracy from computation ±0.1 G), which measures spin-spin interactions due to a high local concentration of paramagnetic species (like colliding nitroxide groups in fast motion, or nitroxides bound in close proximity in slow motion). The line width was quite high for all samples, indicating a high local concentration of nitroxides, but it was the highest (7.6 G) for the slow component of the t=1 minute sample, and it decreased at 40 minutes (5.5 G) and further decreased at 180 minutes (4.2 G). The latter value is even smaller than the line width of the fast component (4.8 G).

Fluorimetry

Fluorescence analysis was performed using a Tecan Infinite® 200 Pro plate reader. Absorption/emission spectra of BASP-ORCA1 were acquired to determine $\lambda_{ex/em}$, which were 640 nm and 705 nm respectively (as expected for the dye used in these studies: Cyanine5.5). Absorption spectra were acquired using a 1 nm wavelength step size at 9 nm bandwidth; emission spectra were obtained using $\lambda_{ex}$ of 640 nm, a 5 nm wavelength step size, and 10 nm bandwidth. To examine the effect of nitroxide-quenching on fluorescence emission intensity, samples were prepared in 96-well plates (Corning, n=3) by mixing 50 μL of 5 mg BASP-ORCA1/mL solution with 50 μL of Asc/GSH solution with one of the following compositions: 120 equivalents (eq, with respect to chex) Asc, 60 eq Asc, 40 eq Asc, and 60 eq Asc+60 eq GSH. Control samples (n=3) were prepared by mixing 50 µL of 5 mg BASP-ORCA1/mL solution with 50 µL of PBS. Fluorescence intensity was monitored continuously for 2 hours; a plateau was typically reached within 40-50 min.

Cell Culture

A549 and HeLa cells (ATCC) were cultured in DMEM media (Sigma-Aldrich) supplemented with 10% fetal bovine serum (FBS, VWR) and 1% penicillin/streptomycin (Thermo Fisher Scientific). Human umbilical vein endothelial cells (HUVEC, Lonza) were cultured in EGM$^+$ media (Lonza) supplemented with 1% penicillin/streptomycin. All cells were housed in 5% $CO_2$ humidified atmosphere at 37° C.

In Vitro Cell Viability

HUVEC cells were plated at 5,000 cells per well (in 100 µL) in 96-well collagen-coated plates (Corning) and allowed to adhere overnight. The media was then replaced with fresh media containing BASP-ORCA1 at various concentrations. The plate was incubated for 72 hours, and cell viability was then determined using the CellTiter-Glo assay (Promega). HeLa cells were plated in 96-well plates (Corning) and cytotoxicity was studied following the same experimental procedure used for HUVEC cells.

Animal Usage

All experiments involving animals were reviewed and approved by the MIT Committee for Animal Care (CAC). BALB/c mice (female, 8-12 weeks old, Taconic) were used for in vivo toxicity, pharmacokinetic studies, and biodistribution (n=3). NCR-NU nude mice (female, 8-12 weeks old, Taconic) were used for in vivo MRI, NIRF imaging, and biodistribution (n=3). All animals received an alfalfa-free diet (TestDiet) at least 2 weeks prior to the start of the studies to minimize auto-fluorescence.

In Vivo Toxicity

Solutions containing 5.0-30 mg of BASP-ORCA1 in 5% glucose were prepared, passed through sterile 0.2 µm filter (Nalgene, PES membrane), and administered into BALB/c mice via tail vein injection. The mice were monitored over a period of 30 days. Initial injections were performed in one mouse for each dose, all of which appeared to be well-tolerated. The highest dose (30 mg) was then administered to another set of mice 01=3). No adverse physical effects and/or significant weight losses were observed.

In Vivo MR and NIRF Imaging Instrumentation

All imaging experiments were performed at the Koch Institute for Integrative Cancer Research at MIT. In vivo MRI was acquired using a Varian 7T/310/ASR-whole mouse MRI system. Scans were collected with respiratory gating (PC-SAM version 6.26 by SA Instruments Inc.) to avoid confounding noise due to chest movement. The respiratory rate and animal temperature were closely monitored during image collection. Coronal T2WIs were collected using the fast spin echo multiple slices pulse sequence with TR=4000 ms; $T_{E(eff)}$=48 ms; ETL=8; FOV=100×50 mm$^2$; 512×256 matrix and 2 averages over 12 slices of 1 mm thickness and 0 mm gap. Axial $T_2$WIs were collected using the fast spin echo multiple slices pulse sequence with $T_R$=4000 ms; $T_{E(eff)}$=48 ms; ETL=8; FOV=45×45 mm$^2$; 256×256 matrix and 2 averages over 10-16 (to capture entire tumor) slices of 1 mm thickness and 0 mm gap.

In vivo NIRF imaging was performed on an IVIS Spectrum-bioluminescent and fluorescent imaging system (Xenogen). Epi-fluorescence imaging was acquired through excitation of the Cy5.5 fluorophore ($\lambda_{ex}/\lambda_{em}$=640/700 nm, exposure time 2-10 seconds) present in BASP-ORCA1.

Pharmacokinetics (PK) and Biodistribution (BD) Studies

BASP-ORCA1 doses (5.0 mg in 5% glucose) were prepared, passed through sterile 0.2 µm filters, and injected into BALB/c mice (groups of n=3). Blood samples were taken at 1, 3, 6, 24, and 48 hours via cardiac puncture after euthanization in a $CO_2$ chamber. The blood samples were subjected to fluorescence imaging (IVIS, Cy5.5$\lambda_{ex}/\lambda_{em}$=640/700 nm, Xenogen) for analysis of blood-compartment PK. For BD, organs from these BALB/c mice were harvested and subjected to fluorescence imaging (IVIS, Cy5.5$\lambda_{ex}/\lambda_{em}$=640/700 nm, Xenogen).

In Vivo MR and NIRF Imaging in Tumor-Bearing Mice

A549 cells were cultured in DMEM media supplemented with 10% fetal bovine serum and 1% penicillin/streptomycin in 5% $CO_2$ humidified atmosphere (37° C.) to a final concentration of 20%. Cells were then harvested, mixed with Matrigel and sterile pH 7.4 PBS buffer (1:1), filtered through sterile 0.2 µm filters, and injected subcutaneously (2.0×10$^6$ cells) into the hind flank of NCR-NU mice. Tumor growth was monitored for 2-4 weeks until appropriate cumulative diameters (~1 cm) were achieved.

MRI and NIRF images were acquired for each animal (n=3-4) before injections. BASP-ORCA1 doses (0.16 mmol chex/kg or 0.23 mmol chex/kg in 5% glucose) were prepared, passed through a sterile 0.2 µm filter, and administered to the tumor-bearing mice via tail vein injection. Tumor imaging was done at pre-determined time points; at the last imaging time point, mice were immediately euthanized in a $CO_2$ chamber, and organs were collected, imaged by NIRF, and stored in dry ice for EPR analysis.

Ex Vivo EPR Spectroscopy

Harvested organs were shipped on dry ice to the University of Nebraska, where they were stored on dry ice. For EPR sample preparation, each tissue sample, one at a time, was rapidly thawed and transferred to a weighed vial; 900 µL of PBS buffer (0.5 mM, pH 7.2) was then added. The mixture was put into an ice-water bath and homogenized with a rotor stator homogenizer, then pipetted into a 4-mm outer diameter EPR sample tube. The samples were degassed by sonication as needed (for instance, when gas bubbles were visible). The EPR tube was capped, sealed with parafilm, and stored briefly in acetone/dry ice bath before spin concentration measurements.

Spin concentrations of nitroxide radicals in tissues (µmol chex per g protein; Note: see below for details of protein content determination) were measured at −30° C. (243.2 K) to increase signal-to-noise of the aqueous samples. Measurements of tissue samples were alternated with that of the spin concentration reference (see next paragraph) and g-value reference (2,2-diphenyl-1-picrylhydrazyl powder was used as the g-value reference). For tissue samples with low signal-to-noise, the cavity background was recorded with identical parameters, including number of scans and receiver gain. Typical parameters were as follows: microwave attenuation-20 dB, modulation amplitude-5 Gauss, spectral width-300 Gauss, resolution-512 points, conversion-40.96, time constant-10.24, and sweep time-20.97 seconds. These parameters were kept identical for the tissues, references, and cavity backgrounds. The number of scans (8-256) and receiver gain were adjusted as needed for each sample.

The reference for spin concentration was 0.50 mM Proxyl in PBS (pH 7.2). This reference was always stored in dry ice, except during measurements, and occasionally re checked for spin concentration decay.

Protein Content Determination

The protein content of tissue homogenate samples was determined using the BCA Protein Assay Kit (ThermoFisher Scientific). These protein contents were then used as a normalizing parameter to compare nitroxide spin concentration and NIRF signal (FIG. 6B).

Ex Vivo NIRF Imaging

To acquire BD, the collected organs and organ homogenates were subjected to NIRF imaging following the same aforementioned experimental procedure as for in vivo NIRF imaging. Furthermore, tissue homogenate samples were transferred into a 96-well plate and imaged for the correlation of NIRF signal and spin concentration.

In Vivo MRI Data Analysis

Signal intensities pre- and post-injection were compared only using slices where tumors and muscle were clearly visible. Using ImageJ software, a region of interest (ROI) around each component was manually drawn. The average signal intensity and area of the ROI were measured; these data were then normalized against the signal intensity of the muscle tissue. Signal intensity was acquired by multiplying area and normalized signal intensity. This process was repeated for all relevant slices for a given organ; the sum of these signal intensities was then calculated and divided for the total area, affording the volume-averaged signal intensity. Signal enhancement by BASP-ORCA1 was quantified by comparing the volume-averaged signal intensities pre- and post-injection.

Procedure for BASP-ORCA Synthesis

Representative Procedure for BASP-ORCA Synthesis with Brush Length of 7.07 (m) and 20 Equivalents (N) of Cross-Linker (BASP-ORCA1, m=7.07, N=20)

All BASP-ORCA syntheses were performed in a glovebox under $N_2$ atmosphere; however, similar results are expected under ambient conditions. All ROMP reactions followed the same general procedure, which was modified from literature examples.

To a 4 mL vial, a suspension of Acetal-XL (15.6 mg, 26.8 µmot, 20.0 eq) in THF (268.0 µL, 0.1 M Acetal-XL) was prepared. To a second 4 mL vial containing a stir bar, chex-MM (35.0 mg, 9.4 µmol, 7.0 eq) was added; Cy-MM was then added from a premade 12.5 mg/mL solution in THF (30.6 µL, 0.094 mol, 0.07 eq). To a third vial, a solution of Grubbs $3^{rd}$ generation bispyridyl catalyst (Grubbs III, 0.02 M in THF) was freshly prepared. THE (91.8 µL) was then added to the MM vial, followed by the addition of Grubbs III solution (67.0 µL, 1.3 µmol, 1.0 eq) to give the desired MM:Grubbs III ratio of 7.07:1 (1 mol % of the Cy-MM), while achieving a total MM concentration of 0.05 M, affording a dark blue solution. The reaction mixture was allowed to stir for 30 minutes at room temperature before an aliquot (~5 µL) was taken out and quenched with 1 drop of ethyl vinyl ether for GPC analysis. The Acetal-XL suspension was then added dropwise (in aliquots of 5 eq, or ~70 µL, every 5 minutes) over the course of 20 minutes into the MM vial, and the polymerizing mixture was allowed to stir for 6 hours at room temperature, affording a dark blue solution. To quench the polymerization, a drop of ethyl vinyl ether was added. The reaction mixture was transferred to an 8 kD molecular weight cutoff dialysis tubing (Spectrum Laboratories) in 10 mL nanopure water, and the solution was dialyzed against water (500 mL×3, solvent exchange every 6 h). The solution of BASP-ORCA was then lyophilized to afford a blue solid.

Other BASP compositions were prepared as follows: MM:Grubbs III ratios of 9.99:1, 7.07:1, or 5.05:1 (m values). Acetal-XL were used in 15, 20, or 30 equivalences (N values). PEG-BASP, which contained no chex-MM, was prepared in an analogous manner to BASP-ORCAs using a PEG-MM lacking chex. Chex-bottlebrush was prepared as previously described.[90]

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Cheon, J.; Lee, J-H. Synergistically Intergrated Nanoparticles as Multimodal Probes for Nanobiotechnology. *Acc. Chem. Res.* 2008, 41, 1630-1640.
2. Na, H. B.; Song, I. C.; Hyeon, T. Inorganic Nanoparticles for MRI Contrast Agents. *Adv. Mater.* 2009, 21, 2133-2148.
3. Lee. D-E.; Koo, H.; Sun, I-C.; Ryu, J. H.; Kim, K.; Kwon, I-C. Multifunctional Nanoparticles for Multimodal Imaging and Theragnosis. *Chem. Soc. Rev.* 2012, 41, 2656-2672.
4. Villaraza, A. J. L.; Bumb, A.; Brechbiel, M. W. Macromolecules, Dendrimers, and Nanomaterials in Magnetic Resonance Imaging: The Interplay between Size, Function, and Pharmacokinetics. *Chem. Rev.* 2010, 110, 2921-2959.
5. Davies, G-L.; Kramberger, I.; Davis, J. J. Environmentally Responsive MRI Contrast Agents. *Chem. Commun.* 2013, 49, 9704-9721.
6. Mastarone, D. J.; Harrison, V. S. R.; Eckermann, A. L.; Parigi, G.; Luchinat, C.; Meade, T. J. A Modular System for the Synthesis of Multiplexed Magnetic Resonance Probes. *J. Am. Chem. Soc.* 2011, 133, 5329-5337.
7. Caravan, P.; Ellison, J. J.; McMurry, T. J.; Lauffer, R. B. Gadolinium (III) Chelates as MRI Contrast Agents: Structure, Dynamics, and Applications. *Chem. Rev.* 1999, 99, 2293-2352.
8. Tu, C.; Nagao, R.; Louie, A. Y. Multimodal Magnetic-resonance/Optical-imaging Contrast Agent Sensitive to NADH. *Angew. Chem. Int. Ed.* 2009, 48, 6547-6551.
9. Hanson, V. S. R.; Carney, C. E.; MacRenaris, K. W. Meade, T. J. A Multimeric MR-optical Contrast Agent for Multimodal Imaging. *Chem. Commun.* 2014, 50, 11469-11471.
10. Harison, V. S. R.; Carney, C. E.; MacRenaris, K. W.; Waters, E. A.; Meade, T. J. Multimeric Near IR-MR Contrast Agent for Multimodal in vivo Imaging. *J. Am. Chem. Soc.* 2015, 137, 9108-9116.
11. MacRenaris, K. W.; Ma, Z.; Krueger, R. L.; Carney, C. E.; Meade, T. J. Cell-permeable Esterase-activated Ca(II)-Sensitive MRI Contrast Agent. *Bioconjugate Chem.* 2016, 27, 465-473.
12. You, Y.; Tomat, E.; Hwang, K.; Atanasijevic, T.; Nam, W.; Jasanoff, A. P.; Lippard, S. Manganese Displacement from Zinpyr-1 Allows Zinc Detection by Fluorescence Microscopy and Magnetic Resonance Imaging. *Chem. Commun.* 2010, 46, 4139-4141.
13. Zhang, X.; Jing, X.; Liu, T.; Han, G.; Li, H.; Duan, C. Dual-functional Gadolinium-based Copper(II) Probe for Selective Magnetic Resonance Imaging and Fluorescence Sensing. *Inorg. Chem.* 2012, 51, 2325-2331.
14. Mi, P.; Kokuryo, D.; Cabral, H.; Wu, H.; Terada, Y.; Saga, T.; Aoki, I.; Nishiyama, N.; Kataoka, K. A pH-activatable Nanoparticle with Signal-amplification Capabilities for non-invasive Imaging of Tumor Malignancy. *Nat. Nanotechnol.* 2016, 11, 724-730.
15. Kokuryo, D.; Anraku, Y.; Kishimura, A.; Tanaka, S.; Kano, M. R.; Kershaw, J.; Nishiyama, N.; Saga, T.; Aoki, I. Kataoka, K. SPIO-PICsome: Development of a Highly Sensitive and Stealth-capable MRI Nano-agent for Tumor Detection using SPIO-loaded Unilamellar Polyion Complex Vesicles (PICsomes). *J. Control. Release.* 2013, 169, 220-227.
16. Mi, P.; Kokuryo, D.; Cabral, H.; Kumagai, M.; Nomoto, T.; Aoki, I.; Terada, Y.; Kishimura, A.; Nishiyama, N.; Kataoka, K. Flydrothermally Synthesized PEGylated Calcium Phosphate Nanoparticles Incorporating Gd-DTPA for Contrast Enhanced MRI Diagnosis of Solid Tumors. *J. Control. Release.* 2014, 174, 63-71.
17. Chou, S-W.; Shau, Y-H.; Wu, P-C.; Yang, Y-S.; Shieh, D-B.; Chen, C-C. in vitro and in vivo Studies of FePt Nanoparticles for Dual Modal CT/MRI Molecular Imaging. *J. Am. Chem. Soc.* 2010, 132, 13270-13278.
18. Holbrook, R. J.; Rammohan, N.; Rotz, M. W. MacRenaris, K. W.; Preslar, A. T.; Meade, T. J. Gd(III)-dithiolane Gold Nanoparticles for T1-Weighted Magnetic Resonance Imaging of the Pancreas. *Nano Lett* 0.2016, 16, 3202-3209.
19. Nicholls, F. J.; Rotz, M. W.; Ghuman, H.; MacRenaris, K. W.; Meade, T. J. Modo, M. DNA-gadolinium-gold Nanoparticles for in vivo T1 MR Imaging of Transplanted Human Neural Stem Cells. *Biomaterials.* 2016, 77, 291-306.
20. Choi, J-S.; Lee, J-H.; Shin, T-H.; Song, H-T.; Kim, E. Y.; Cheon, J. Self-confirming "AND" Logic Nanoparticles for Fault-free MRI. *J. Am. Chem. Soc.* 2010, 132, 11015-11017.
21. Medarova, Z.; Pham, W.; Farrar, C.; Petkova, V.; Moore, A. in vivo Imaging of siRNA Delivery and Silencing in Tumors.
22. Shellock, F. G.; Kanal, E. Safety of Magnetic Resonance Imaging Contrast Agents. *J. Magn. Reson. Imaging.* 1999, 10, 477-484.
23. Swaminathan, S.; Horn, T. D.; Pellowski, D.; Abul-Ezz, S.; Bornhorst, J. A. Nephrogenic Systemic Fibrosis, Gadolinium, and Iron Mobilization. *N. Engl. J. Med.* 2007, 357, 720-722.
24. Shin, T-H. Choi, Y.; Kim, S.; Cheon, J. Recent Advances in Magnetic Nanoparticle-based Multi-modal Imaging. *Chem. Soc. Rev.* 2015, 44, 4501-4516.
25. Verwilst, P.; Park, S.; Yoon, B.; Kim, J. S. Recent Advances in Gd-chelate Based Bimodal Optical/MRI Contrast Agents. *Chem. Soc. Rev.* 2015, 44, 1791-1806.
26. Feng, J.; Liu, H.; Bhakoo, K. K.; Lu. L.; Chen, Z. A Metabonomic Analysis of Organ Specific Response to USPIO Administration. *Biomaterials.* 2011, 32, 6558-6569.
27. Rizzo, L. Y.; Golombek, S. K.; Mertens, M. E.; Pan, Y.; Laaf, D.; Broda, J.; Jayapaul, J.; Mockel, D.; Subr, V.; Hennink, W. E.; Storm, G.; Simon, U.; Jahnen-Dechent, W.; Kiessling, F.; Lammers, T. In Vivo Nanotoxicity Testing Using the Zebrafish Embryo Assay. *J. Mater. Chem. B.* 2013, 1, 3918-3925.
28. Nardone, B.; Saddleton, E.; Laumann, A. E.; Edwards, B. J.; Raisch, D. W.; McKoy, J. M.; Belknap, S. M.; Bull, C.; Iiaryani, A.; Cowper, S. E.; Abu-Alfa, A. K.; Miller, F. H.; Godinez-Puig, V.; Dharnidharka, V. R.; West, D. P. Pediatric Nephrogenic Systemic Fibrosis is Rarely Reported: a RADAR Report. *Pediatr. Radiol.* 2014, 44, 173-180.
29. Mendichovszky, I. A.; Marks, S. D.; Simcock, C. M.; Olsen, O. E. Gadolinium and Nephrogenic Systemic Fibrosis: Time to Tighten Practice. *Pediatr. Radio.* 2008, 38, 489-496.
30. Hatje, V.; Bruland, K. W.; Flegal, A. R. Increases in Anthropogenic Gadolinium Anomalies and Rare Earth Element Concentration in San Francisco Bay over a 20 Year Record. *Environ. Sci. Technol.* 2016, 50, 4159-4168.

31. Lim, Y. T.; Noh, Y-W.; Cho, J-H.; Han, J. H.; Choi, B. S.; Kwon, J.; Hong, K. S.; Gokama, A.; Cho, Y-H.; Chung, B. H. Multiplexed Imaging of Therapeutic Cells with Multispectrally Encoded Magnetofluorescent Nanocomposite Emulsions. *J. Am. Chem. Soc.* 2009, 131, 17145-17154.

32. Rolfe, B. E.; Blakey, I.; Squires, O.; Peng, H.; Boase, N. R. B.; Alexander, C.; Parsons, P. G.; Boyle, G. M.; Whittaker, A. K.; Thurecht, K. J. Multimodal Polymer Nanoparticles with Combined $^{19}$F Magnetic Resonance and Optical Detection for Tunable, Targeted, Multimodal Imaging in vivo. *J. Am. Chem. Soc.* 2014, 136, 2413-2419.

33. Patrick, M. J.; Janjic, J. M.; Teng, H.; O'Hear, M. R.; Brown, C. W.; Stokum, J. A.; Schmidt, B. F.; Ahrens, E. T. Waggoner, A. S. Intracellular pH Measurements Using Perfluorocarbon Nanoemulsions. *J. Am. Chem. Soc.* 2013, 135, 18445-18457.

34. Bar-Shir, A.; Yadav, N. N.; Gilad, A. A.; van Zijl, P. C. M.; McMahon, M. T.; Bulte, J. W. M. Single $^{19}$F Probe for Simultaneous Detection of Multiple Metal Ions Using miCEST MRI. *J. Am. Chem. Soc.* 2015, 137, 78-81.

35. Lock, L. L.; Li, Y.; Mao, X.; Chen, H.; Staedtke, V.; Bai, R.; Ma, W.; Lin, R.; Li, Y.; Liu, G.; Cui, H. One-component Supramolecular Filament Hydrogels as Theranostic Label-free Magnetic Resonance Imaging Agents. *ACS Nano.* 2017, 11, 797-805.

36. Ferrauto, G.; Gregorio, E. D.; Baroni, S.; Aime, S. Frequency-encoded MRI-CEST Agents Based on Paramagnetic Liposomes/RBC Aggregates. *Nano Lett.* 2014, 14, 6857-6862.

37. Ratnakar, S. J.; Soesbe, T. C.; Lumata, L. L.; Do, Q. N.; Viswanathan, S.; Lin, C.-Y.; Sherry, A. D.; Kovacs, Z. Modulation of CEST Images in vivo by Tr Relaxation: a New Approach in the Design of Responsive PARACEST Agents. *J. Am. Chem. Soc.* 2013, 135, 14904-14907.

38. Ferrauto, G.; Castelli, D. D.; Gregorio, E. D.; Langereis, S.; Burdinski, D.; Grull, H.; Terreno, E.; Aime, S.; Lanthanide-loaded Erythrocytes as Highly Sensitive Chemical Exchange Saturation Transfer MRI Contrast Agents. *J. Am. Chem. Soc.* 2014, 136, 638-641.

39. Terreno, E.; Castelli, D. D.; Viale, A.; Aime, S. Challenges for Molecular Magnetic Resonance Imaging. *Chem. Rev.* 2010, 110, 3019-3042.

40. Glunde, K.; Artemov, D.; Penet, M-F.; Jacobs, M. A.; Bhujwalla, Z. M. Magnetic Resonance Spectroscopy in Metabolic and Molecular Imaging and Diagnostic of Cancer. *Chem. Rev.* 2010, 110, 3043-3059.

41. Smith, B. R.; Gambhir, S. S. Nanomaterials for In Vivo Imaging. *Chem. Rev.* 2017, 117, 901-986.

42. Harvey, P.; Kuprov, I.; Parker, D. Lanthanide Complexes as Paramagnetic Probes for $^{19}$F Magnetic Resonance. *Eur. J. Inorg. Chem.* 2012, 12, 2015-2022.

43. Boase, N. R. B.; Blakey, I.; Thurecht, K. J. Molecular Imaging with Polymers. *Polym. Chem.* 2012, 3, 1384-1389.

44. Tirotta, I.; Dichiarante, V.; Pigliacelli, C.; Cavallo, G.; Terraneo, G.; Bombelli, F. B.; Metrangolo, P.; Resnati, G. $^{19}$F Magnetic Resonance Imaging (MRI): From Design of Materials to Clinical Applications. *Chem. Rev.* 2015, 115, 1106-1129.

45. Aime, S.; Castelli, D. D.; Crich, S. G.; Gianolio, E.; Terreno, E. Pushing the Sensitivity Envelope of Lanthanide-based Magnetic Resonance Imaging (MRI) Contrast Agents for Molecular Imaging Applications. *Acc. Chem. Res.* 2009, 822-831.

46. Liu, G.; Song, X.; Chan, K. W. Y.; McMahon, M. T. Nuts and Bolts of Chemical Exchange Saturation Transfer MRI. *NMR Biomed.* 2013, 26, 810-828.

47. Rajca, A.; Wang, Y.; Boska, M.; Paletta, J. T.; Olankitwanit, A.; Swanson, M. A.; Mitchell, D. G.; Eaton, S. S.; Eaton, G. R.; Rajca, S. Organic Radical Contrast Agents for Magnetic Resonance Imaging. *J. Am. Chem. Soc.* 2012, 134, 15724-15727.

48. Rajca, A.; Wang, Y.; Boska, M.; Paletta, J. T.; Olankitwanit, A.; Swanson, M. A.; Mitchell, D. G.; Eaton, S. S.; Eaton, G. R.; Rajca, S. Correction to Organic Radical Contrast Agents for Magnetic Resonance Imaging. *J. Am. Chem. Soc.* 2014, 136, 3318-3318.

49. Hyodo, F.; Soule, B. P.; Matsumoto, K-I.; Matusmoto, S.; Cook, J. A.; Hyodo, E.; Sowers, A. L.; Krishna, M. C.; Mitchell, J. B. Assessment of Tissue Redox Status Using Metabolic Responsive Contrast Agents and Magnetic Resonance Imaging. *J. Pharm. Pharmacol.* 2008, 60, 1049-1060.

50. Hyodo, F.; Chuang, K-H.; Goloshevsky, A. G.; Sulima, A.; Griffiths, G. L.; Mitchell, J. B.; Koretsky, A. P.; Krishna, M. C. Brain Redox Imaging Using Blood-brain Barrier-permeable Nitroxide MRI Contrast Agent. *J. Cereb. Blood Flow Metab.* 2008, 28, 1165-1174.

51. Brasch, R. C. Work in Progress: Methods of Contrast Enhancement for NMR Imaging and Potential Applications. A Subject Review. *Radiology.* 1983, 147, 781-788.

52. Brasch, R. C.; London, D. A.; Wesbey, G. E.; Tozer, T. N.; Nitecki, D. E.; Williams, R. D.; Doemeny, J.; Tuck, L. D.; Lallemand, D. P. Work in Progress: Nuclear Magnetic Resonance Study of a Paramagnetic Nitroxide Contrast Agent for Enhancement of Renal Structures in Experimental Animals. *Radiology,* 1983, 147, 773-779.

53. Matsumoto, K-I.; Hyodo, F.; Matsumoto, A.; Koretsky, A. P.; Sowers, A. L.; Mitchell, J. B.; Krishna, M. C. High-resolution Mapping of Tumor Redox Status by Magnetic Resonance Imaging Using Nitroxides as Redox-sensitive Contrast Agents. *Clin. Cancer Res.* 2006, 12, 2455-2462.

54. Hyodo, F.; Matsumoto, K-I.; Matsumoto, A.; Mitchell, J. B.; Mrishna, M. C. Probing the Intracellular Redox Status of Tumors with Magnetic Resonance Imaging and Redox-sensitive Contrast Agents. *Cancer Res.* 2006, 66, 9921-9928.

55. Zhelev, Z.; Bakalova, R.; Aoki, I.; Lazarova, D.; Saga, T. Imaging of Superoxide Generation in the Dopaminergic Area of the Brain in Parkinson's Disease, Using Mito-TEMPO. *ACS. Chem. Neurosci.* 2013, 4, 1439-1445.

56. Davis, R. M.; Sowers, A. L.; Degraff, W.; Bernado, M.; Thetford, A.; Krishna, M. C.; Mitchell, J. B. A Novel Nitroxide is an Effective Brain Redox Imaging Contrast Agent and in vivo Radioprotector. *Free. Radic. Biol. Med.* 2011, 51, 780-790.

57. Zhelev, Z.; Bakalova, R.; Aoki, I.; Matsumoto, K-I.; Gadjeva, V.; Anzai, K.; Kanno, I. Nitroxide Radicals for Labelling of Conventional Therapeutics and Noninvasive Magnetic Resonance Imaging of Their Permeability for Blood-brain Barrier: Relationship between Structure, Blood Clearance, and MRI Signal Dynamic in the Brain. *Mol. Pharm.* 2009, 6, 504-512.

58. Doane, T. L.; Burda, C. The Unique Role of Nanoparticles in Nanomedicine: Imaging, Drug Delivery and Therapy. *Chem. Soc. Rev.* 2012, 41, 2885-2911.

59. Jokerst J. V.; Gambhir, S. S. Molecular Imaging with Theranostic Nanoparticles. *Acc. Chem. Res.* 2011, 44, 1050-1060.
60. Joralemon, M. J.; McRae, S.; Emrick, T. PEGylated Polymers for Medicine: from Conjugation to Self-assembled Systems. *Chem. Commun.* 2010, 46, 1377-1393.
61. Torchilin, V. Tumor Delivery of Macromolecular Drugs Based on the EPR Effect *Adv. Drug Deliv. Rev.* 2011, 63, 131-135.
62. Anraku, Y.; Kishimura, A.; Kobayashi, A.; Oba, M.; Kataoka, K. Size-controlled Long-circulating PICsome as a Ruler to Measure Critical Cut-off Disposition Size into Normal and Tumor Tissues. *Chem. Commun.* 2011, 47, 6054-6056.
63. Cabral, H.; Matsumoto, Y.; Mizuno, K.; Chen, Q.; Murakami, M.; Kimura, M.; Terada, Y.; Kano, M. R.; Miyazono, K.; Uesaka, M.; Nishiyama, N.; Kataoka, K. Accumulation of Sub-100 nm Polymeric Micelles in Poorly Permeable Tumours Depends on Size. *Nat. Nanotechnol.* 2011, 6, 815-823.
64. Jokerst, J. V.; Lobovkina, T.; Zare, R. N.; Gambhir, S. S. Nanoparticle PEGylation for Imaging and Therapy. *Nanomedicine,* 2011, 6, 715-728.
65. Elliott, K. A. Metabolism of brain tissue slices and suspensions from various mammals. *J. Neurophysiol.* 1948, 11, 473-484.
66. Tolmasoff, J. M.; Ono, T.; Cutler, R. G. Superoxide dismutase: correlation with lifespan and specific metabolic rate in primate species. *Proc. Natl Acad. Sci. USA,* 1980, 77, 2777-2781.
67. Zhelev, Z.; Bakalova, R.; Aoki, I.; Matsumoto, K-I.; Gadjeva, V.; Anzai, K.; Kanno, I. Nitroxyl Radicals as Low Toxic Spin-labels for Non-invasive Magnetic Resonance Imaging of Blood-brain Barrier Permeability for Conventional Therapeutics. *Chem. Commun.* 2009, 53-55.
68. Samuni, Y.; Gamson, J.; Samuni, A.; Yamada, K.; Russo, A.; Krishna, M. C.; Mitchell, J. B. Factors Influencing Nitroxide Reduction and Cytotoxicity in Vitro. *Antioxid. Redox Signal.* 2004, 587-595.
69. Paletta, J. T.; Pink, M.; Foley, B.; Rajca, S.; Rajca, A. Synthesis and Reduction Kinetics of Sterically Shielded Pyrrolidine Nitroxides. *Org. Lett.* 2012, 14, 5322-5325.
70. Sowers, M. A.; McCombs, J. R.; Wang, Y.; Paletta, J. T.; Morton, S. W.; Dreaden, E. C.; Boska, M. D.; Ottaviani, M. F.; Hammond, P. T.; Rajca, A.; Johnson, J. A. Redox Responsive Branched Bottebrush Polymers for In Vivo MRI and Fluorescence Imaging. *Nat. Commun.* 2014, 5.
71. Liu, J.; Gao, A. X.; Johnson, J. A. Particles Without a Box: Brush-first Synthesis of Photodegradable PEG Star Polymers under Ambient Conditions. *J. Vis. Exp.* 2013, 80, e50874.
72. Burts, A. O.; Liao, L.; Lu, Y. Y.; Tirrell, D. A.; Johnson, J. A. Brush-first and Click: Efficient Synthesis of Nanoparticles that Degrade and Release Doxorubicin in Response to Light. *Photochem. Photobiol.* 2014, 90, 380-385.
73. Love, J. A.; Morgan, J. P.; Trnka, T. M.; Grubbs, R. H. A Practical and Highly Active Ruthenium-based Catalyst that Effects the Cross Metathesis of Acrylonitrile. *Angew. Chem. Int. Ed.* 2002, 41, 4035-4037.
74. Budil, D. E.; Lee, S.; Saxena, S.; Freed, J. H. Nonlinear-least-square Analysis of Slow-motion EPR Spectra in One and Two Dimensions Using a Modified Levenberg-Marquardt-algorithm. *J. Magn. Reson., Ser. A.* 1996, 120, 155-189.
75. Na, H. B.; Lee, J. H.; An, K.; Park, Y. I.; Park, M.; Lee, I. S.; Nam, D.-H.; Kim, S. T.; Kim, S.-H.; Kim, S.-W. et al. Development of a T1 Contrast Agent for Magnetic Resonance Imaging Using MnO Nanoparticles. *Angew. Chem. Int. Ed.* 2007, 46, 5397-5401.
76. Detappe, A.; Kunjachan, S.; Sancey, L.; Motto-Ros, V.; Biancur, D.; Drane, P.; Guieze, R.; Makrigiorgos, G. M.; Tillement, O.; Langer, R. et al. Advanced multimodal nanoparticles delay tumor progression with clinical radiation therapy. *J. Control. Release.* 2016, 238, 103-113.
77. Sancey, L.; Kotb, S.; Trulllet, C.; Appaix, F.; Marais, A.; Thomas, E.; van der Sanden, B.; Klein, J. P.; Laurent, B.; Cottier, M. et al. Long-Term in Vivo Clearance of Gadolinium-Based AGuIX Nanoparticles and Their Biocompatibility after Systemic Injection. *ACS Nano.* 2015, 9, 2477-2488.
78. Wei, H.; Bruns, O. T.; Kaul, M. G.; Hansen, E. C.; Barch, M.; Wisniowska, A.; Chen, O.; Chen, Y.; Li, N.; Okada, S.; Cordero, J. M.; Heine, M.; Farrar, C. T.; Montana, D. M.; Adam, G.; Ittrich, H.; Jasanoff, A.; Nielsen, P.; Bawendi, M. G. Exceedingly Small Iron Oxide Nanoparticles as Positive MRI Contrast Agents. *Proc. Natl. Acad. Sci. U.S.A.* 2017, 114, 2325-2330.
79. Li, Y.; Lei, X.; Jockusch, S.; Chen, J. Y.-C.; Frunzi, M.; Johnson, J. A.; Lawler, R. G.; Murata, Y.; Murata, M.; Komatsu, K.; Turro, N. J. A Magnetic Switch for Spin-catalyzed Interconversion of Nuclear Spin Isomers. *J. Am. Chem. Soc.* 2010, 132, 4042-4043.
80. Li, Y.; Lei, X.; Lawler, R. G.; Murata, Y.; Komatsu, K.; Turro, N. J. Distance-dependent Paramagnet-enhanced Nuclear Spin Relaxation of $H_2@C_{60}$ Derivatives Covalently Linked to a Nitroxide Radical. *J. Phys. Chem. Lett.* 2010, 1, 2135-2138.
81. Satori, E.; Ruzzi, M.; Lawler, R. G.; Turro, N. J. Nitroxide Paramagnet-induced Para-ortho Conversion and Nuclear Spin Relaxation of $H_2$ in Organic Solvents. *J. Am. Chem. Soc.* 2008, 130, 12752-12756.
82. Keana, J. F. W.; Pou, S.; Rosen, G. M. Nitroxides as Potential Contrast Enhancing Agent for MRI Application: Influence of Structure on the Rate of Reduction by Rat Hepatocytes, Whole Liver Homogenate, Subcellular Fractions, and Ascorbate. *Mag. Res. Med.* 1987, 5, 525-536.
83. Bobko, A. A.; Kirilyuk, I. A.; Grigor'ev, I. A.; Zweier, J. L.; Khramtsov, V. V. Reversible Reduction of Nitroxides to Hydroxylamines: Role for Ascorbate and Glutathione. *Free. Radic. Biol. Med.* 2007, 42, 404-412.
84. Blinco, J. P.; Fairfull-Smith, K. E.; Morrow, B. J.; Bottle, S. E. Profluorescent Nitroxides as Sensitive Probes of Oxidative Change and Free Radical Reactions. *Aust. J. Chem.* 2011, 64, 373-389.
85. Yang, Y.; Zhao, Q.; Feng, W.; Li, F. Luminescent Chemodosimeters for Bioimaging. *Chem. Rev.* 2013, 113, 192-270.
86. Ahn, H-Y.; Fairfull-Smith, K. E.; Morrow, B. J.; Lussini, V.; Kim, B.; Bondar, M. V.; Bottle, S. E.; Belfield, K. D. Two-photon Fluorescence Microscopy Imaging of Cellular Oxidative Stress Using Profluorescent Nitroxides. *J. Am. Chem. Soc.* 2012, 134, 4721-4730.
87. Workman, P.; Aboagye, E. O.; Balkwill, F.; Balmain, A.; Bruder, G.; Chaplin, D. J.; Double, J. A.; Everitt, J.; Farningham, D. A. H.; Glennie, M. J.; Kelland, L. R.; Robinson, V.; Stratford, I. J.; Tozer, G. M.; Watson, S.; Wedge, S. R.; Eccles, S. A. Guidelines for the Welfare and Use of Animals in Cancer Research. *Br. J. Cancer.* 2010, 102, 1555-1577.

88. Chapman, K.; Sewell, F.; Allais, L.; Delongeas, J.-L.; Donald, E.; Festag, M.; Kervyn, S.; Ockert, D.; Nogues, V.; Palmer, H.; Popovic, M.; Roosen, W.; Schoenmakers, A.; Somers, K.; Stark, C.; Stei, P.; Robinson, S. A Global Pharmaceutical Company Initiative: an Evidence-based Approach to Define the Upper Limit of Body Weight Loss in Short Term Toxicity Studies. *Regul. Toxicol. Pharmacol.* 2013, 67, 27-38.
89. Rowland, M.; Benet, L. Z.; Graham, G. G. Clearance Concepts in Pharmacokinetics. *J. Pharmacokinet. Biopharm.* 1973, 1, 123-136.
90. Sowers, M. A.; McCombs, J. R.; Wang, Y.; Paletta, J. T.; Morton, S. W.; Dreaden, E. C.; Boska, M. D.; Ottaviani, M. F.; Hammond, P. T.; Rajca, A.; Johnson, J. A. Redox-Responsive Branched-bottlebrush Polymers for in vivo MRI and Fluorescence Imaging. *Nat. Commun.* 2014, 5, 5460.
91. Angelov, V.; Velichkova, H.; Ivanov, E.; Kotsilkova, R.; Delville, M-H.; Cangiotti, M.; Fattori, A.; Ottaviani, M. F. EPR and Rheological Study of Hybrid Interfaces in Gold-clay-epoxy Nanocomposites. *Langmuir.* 2014, 30, 13411-13421.
92. Wang, Y.; Paletta, J. T.; Berg, K.; Reinhart, E.; Rajca, S.; Rajca, A. Synthesis of Unnatural Amino Acids Functionalized with Sterically Shielded Pyrroline Nitroxides. *Org. Lett.* 2014, 16, 5298-5300.
93. Paletta, J. T.; Pink, M.; Foley, B.; Rajca, S.; Rajca, A. Synthesis and Reduction Kinetics of Sterically Shielded Pyrrolidine Nitroxides. *Org. Lett.* 2012, 14, 5322-5325.

What is claimed is:

1. A brush-arm star polymer comprising one or more repeating units of Formula (I) and one or more repeating units of Formula (II):

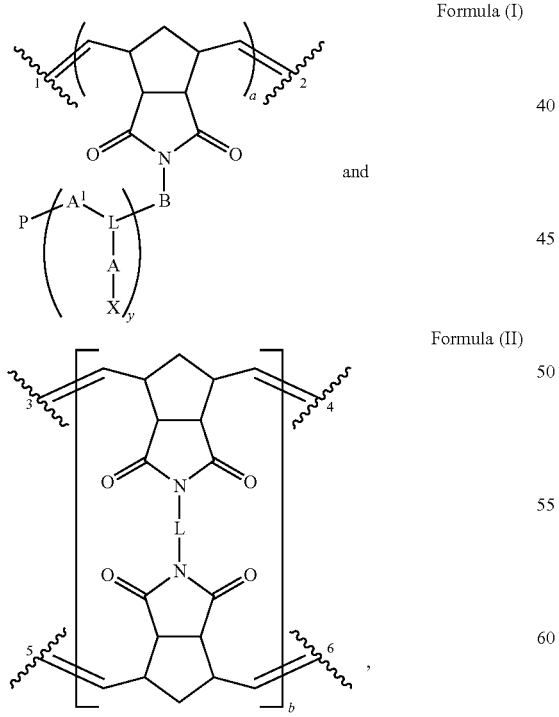

or a salt thereof, wherein:
the combined number of repeating units of Formula (I) and repeating units of Formula (II) is at least 100;

each A is independently $C_1$-$C_{12}$ alkylene or $C_1$-$C_{12}$ heteroalkylene, wherein each of the alkylene and heteroalkylene is independently optionally substituted with 1-2;
each $A^1$ is $C_1$-$C_{12}$ heteroalkylene, wherein each of the heteroalkylene is independently optionally substituted with 1-2 oxo;
each B is $C_1$-$C_{12}$ alkylene, wherein each of the alkylene is independently optionally substituted with one oxo;
each X is an imaging agent, wherein at least one imaging agent is an organic nitroxide radical-containing imaging agent;
each P is a polyethylene glycol;
each instance of L is independently selected from the group consisting of $C_1$-$C_{12}$ alkylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), and a combination of any two thereof;

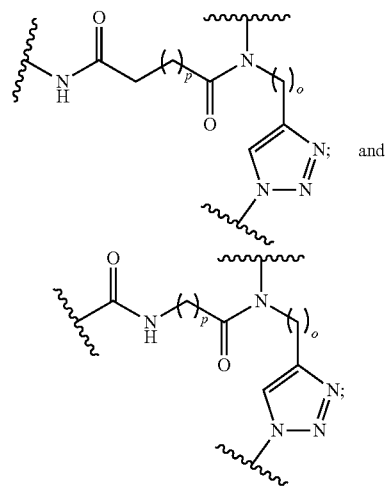

wherein:
each of the alkylene, heteroalkylene, arylene, and heteroarylene is independently optionally substituted with 1-24 independently selected $R^1$ selected from the group consisting of alkyl, heteroalkyl, halo, cyano, oxo, nitro, —$OR^A$, —$N(R^A)_2$, —$NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, and —$S(O)_mR^A$;
each of the heteroarylene is independently monocyclic, 5- or 6-membered heteroarylene;
each $R^A$ is independently hydrogen, $C_1$-$C_6$ alkyl, $C_1$-$C_6$ heteroalkyl, or $C_1$-$C_6$ haloalkyl;
each m is independently 1 or 2; and
each of p and o are independently an integer between 0 and 20, inclusive;
each of a and b is 1;
when "1", "2", "3", "4", "5", and/or "6" shown in Formula (I) or Formula (II) are terminal groups, the terminal groups are independently selected from the group consisting of optionally substituted alkenyl, optionally substituted carbocyclyl, optionally substituted heterocyclyl, optionally substituted aryl, and optionally substituted heteroaryl; and each y is independently an integer between 1 and 100, inclusive.

2. The brush-arm star polymer of claim 1, wherein P is a polyethylene glycol with a number average molecular weight about 2000, about 2500, about 3000, about 3500, or about 4000, g/mol.

3. The brush-arm star polymer of claim 1, wherein: each B is $C_1$-$C_{12}$ alkylene, wherein each of the alkylene is substituted with one.

4. The brush-arm star polymer of claim 1, wherein each L of Formula (I) is independently selected from

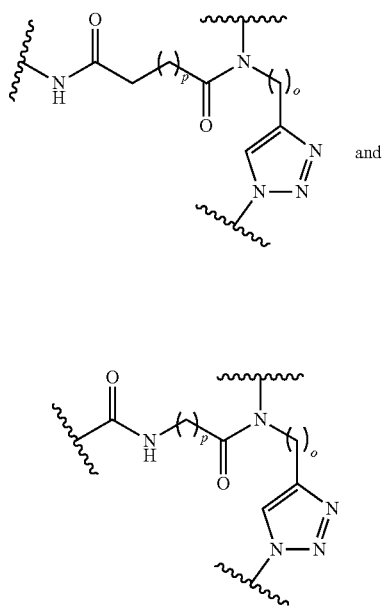

and

5. The brush-arm star polymer of claim 1, wherein when the brush-arm star polymer comprises two or more imaging agents, at least one imaging agent is a chelated metal, inorganic compound, or organic compound, or a salt thereof.

6. The brush-arm star polymer of claim 1, wherein at least one organic nitroxide radical-containing imaging agent is of the formula:

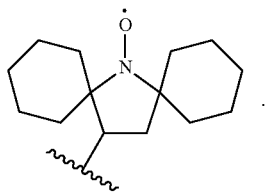

7. The brush-arm star polymer of claim 1, wherein:
each instance of L of Formula (I) is independently $C_1$-$C_{12}$ alkylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), or a combination of any two thereof, wherein each of the alkylene, heteroalkylene, arylene, and heteroarylene is independently optionally substituted with 1-24 independently selected $R^1$ selected from the group consisting of alkyl, heteroalkyl, halo, cyano, oxo, nitro, —$OR^A$, —$N(R^A)_2$, $NR^AC(O)R^A$, —$NR^AC(O)OR^A$, —$NR^AC(O)N(R^A)_2$, —$C(O)N(R^A)_2$, —$C(O)R^A$, —$C(O)OR^A$, —$OC(O)R^A$, —$OC(O)OR^A$, —$OC(O)N(R^A)_2$, —$SR^A$, and —$S(O)_mR^A$.

8. The brush-arm star polymer of claim 1, wherein at least one repeating unit of Formula (I) is of formula:

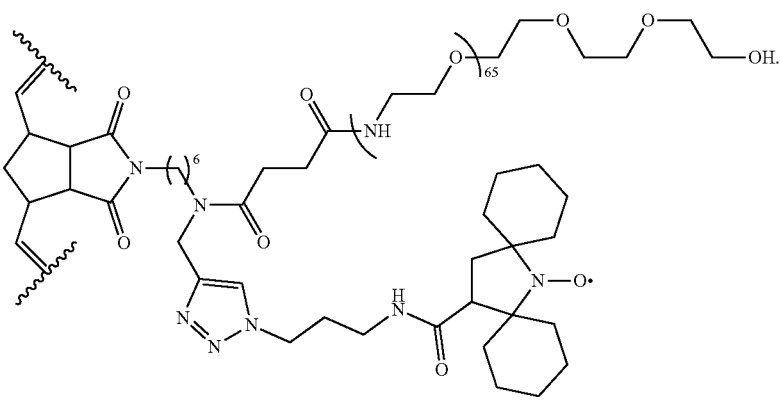

9. The brush-arm star polymer of claim 1, wherein:
each instance of L of Formula (I) is independently $C_1$-$C_{12}$ alkylene, $C_1$-$C_{12}$ heteroalkylene, ($C_0$-$C_{12}$ alkylene)-arylene-($C_0$-$C_{12}$ alkylene), ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), ($C_0$-$C_{12}$ alkylene)-heteroarylene-($C_0$-$C_{12}$ alkylene), ($C_0$-$C_{12}$ heteroalkylene)-heteroarylene-($C_0$-$C_{12}$ alkylene), ($C_0$-$C_{12}$ heteroalkylene)-heteroarylene-($C_0$-$C_{12}$ heteroalkylene), or a combination of any two thereof, wherein each of the alkylene, heteroalkylene, arylene, and heteroarylene is independently optionally substituted with 1-24 independently selected $R^1$ selected from the group consisting of alkyl, heteroalkyl, halo, cyano, oxo, nitro, and —$OR^4$.

10. The brush-arm star polymer of claim 1, wherein the repeating unit of Formula (II) is of formula:

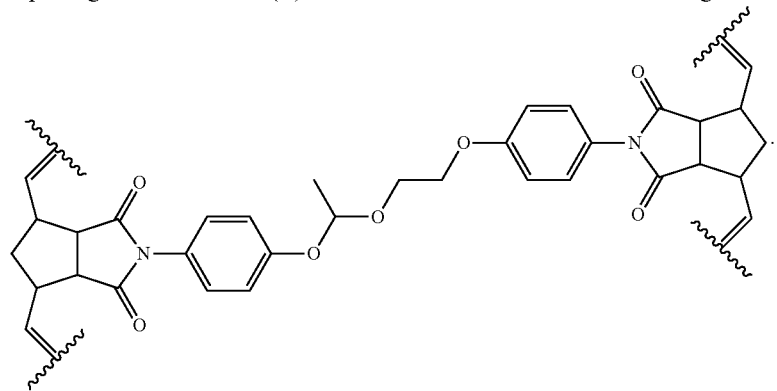

11. The brush-arm star polymer of claim 1, wherein the ratio of repeating unit of Formula (I) and repeating unit of Formula (II) is between about 1:20 to about 20:1, respectively.

12. A method of producing a brush-arm star polymer of claim 1 comprising:
(a) reacting one or more macromonomers of Formula (III):

Formula (III)

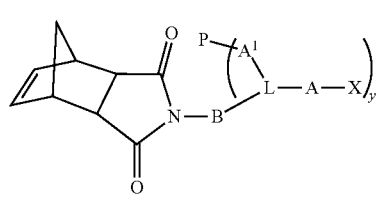

or a salt thereof, with a metathesis catalyst to form a living polymer; and
(b) mixing a crosslinker of Formula (IV):

Formula (IV)

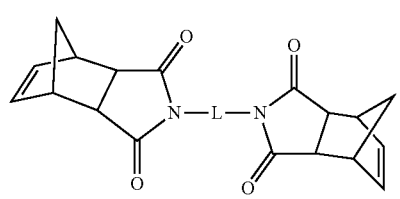

or a salt thereof, with the living polymer.

13. A method of imaging a subject, the method comprising steps of:
administering to a subject an effective amount of the polymer of claim 1; and
acquiring an image.

14. A method of performing magnetic resonance imaging of a subject, the method comprising steps of:
administering to a subject an effective amount of the polymer of claim 1; and
acquiring a magnetic resonance image;
wherein at least one imaging agent is useful for performing magnetic resonance imaging.

15. A method of performing near-infrared fluorescence imaging of a subject, the method comprising steps of:
administering to a subject an effective amount of the polymer of claim 1; and
acquiring a near-infrared fluorescence image;
wherein at least one imaging agent is useful for performing near-infrared fluorescence imaging.

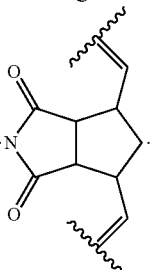

16. The brush-arm star polymer of claim 1, wherein each P is polyethylene glycol with a number average molecular weight ranging from about 200 g/mol to about 6000 g/mol, inclusive.

17. The brush-arm star polymer of claim 1, wherein each L of Formula (II) is of the formula:

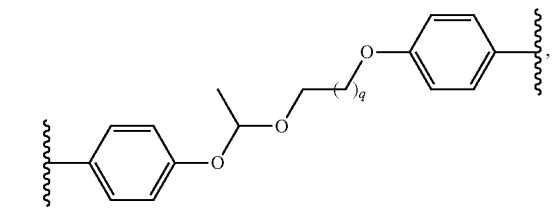

wherein each q is independently an integer between 0 and 20, inclusive.

18. The brush-arm star polymer of claim 1, wherein each A is $C_1$-$C_{12}$ heteroalkylene, wherein each of the heteroalkylene is optionally substituted with 1-2.

19. The brush-arm star polymer of claim 1, wherein each y is 1.

20. The brush-arm star polymer of claim 5, wherein at least one imaging agent is a near-infrared fluorescence imaging agent.

21. The brush-arm star polymer of claim 5, wherein at least one imaging agent is of the formula:

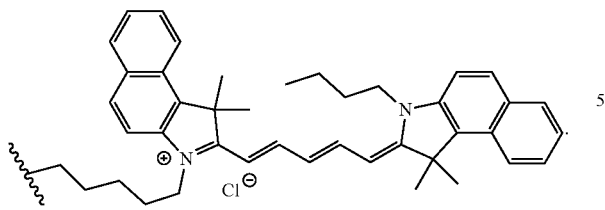

22. The brush-arm star polymer of claim 5, wherein at least one repeating unit of Formula (I) is of formula:

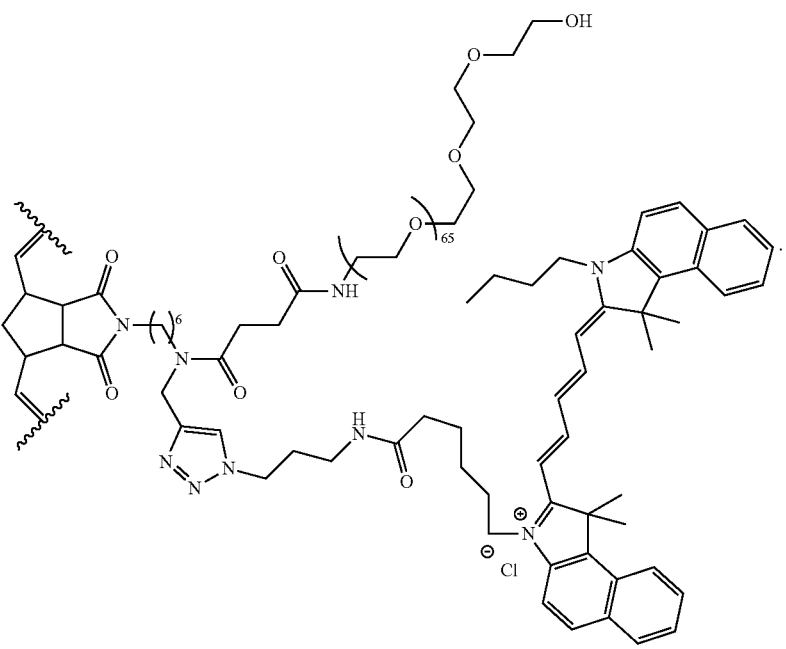

23. The brush-arm star polymer of claim 1, wherein the brush-arm star polymers form a particle of a diameter between about 10 nm and about 1000 nm, inclusive.

24. The brush-arm star polymer of claim 1, wherein each $A^1$ is $C_1$-$C_{12}$ heteroalkylene, wherein each of the heteroalkylene is substituted with 1-2.

25. The brush-arm star polymer of claim 1, wherein each L of Formula (II) is independently ($C_0$-$C_{12}$ heteroalkylene)-arylene-($C_0$-$C_{12}$ alkylene), ($C_0$-$C_{12}$ alkylene)-arylene-($C_0$-$C_{12}$ heteroalkylene), ($C_0$-$C_{12}$ heteroalkylene)-arylene-($C_0$-$C_{12}$ heteroalkylene), or a combination of any two thereof, wherein each of the alkylene, heteroalkylene, and arylene is independently substituted with 1-24 independently selected $R^1$ selected from the group consisting of alkyl, heteroalkyl, halo, cyano, oxo, nitro, —$OR^4$, —$N(R^4)_2$, —$NR^4C(O)R^4$, —$NR^4C(O)OR^4$, —$NR^4C(O)N(R^4)_2$, —$C(O)N(R^4)_2$, —$C(O)R^4$, —$C(O)OR^4$, —$OC(O)R^4$, —$OC(O)OR^4$, —$OC(O)N(R^4)_2$, —$SR^4$, and —$S(O)_mR^4$.

* * * * *

UNITED STATES PATENT AND TRADEMARK OFFICE
CERTIFICATE OF CORRECTION

PATENT NO.         : 11,752,221 B2
APPLICATION NO.    : 16/024643
DATED              : September 12, 2023
INVENTOR(S)        : Jeremiah A. Johnson et al.

It is certified that error appears in the above-identified patent and that said Letters Patent is hereby corrected as shown below:

In the Claims

In Claim 7, in Column 74, Line 34:
"NR$^A$C(O)R$^A$"
Should read:
-- –NR$^A$C(O)R$^A$ --.

In Claim 8, in Column 74, the formula Should read:

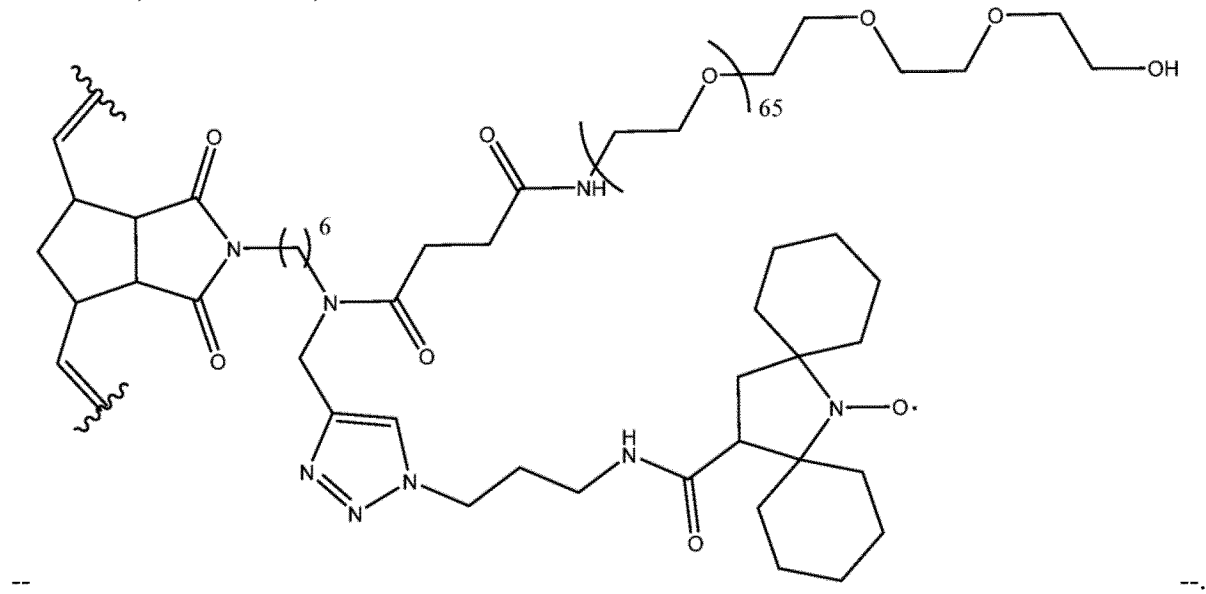

--                                                                                              --.

Signed and Sealed this
Eighteenth Day of February, 2025

Coke Morgan Stewart
*Acting Director of the United States Patent and Trademark Office*

CERTIFICATE OF CORRECTION (continued)
U.S. Pat. No. 11,752,221 B2

In Claim 12, in Column 75, the formula Should read:

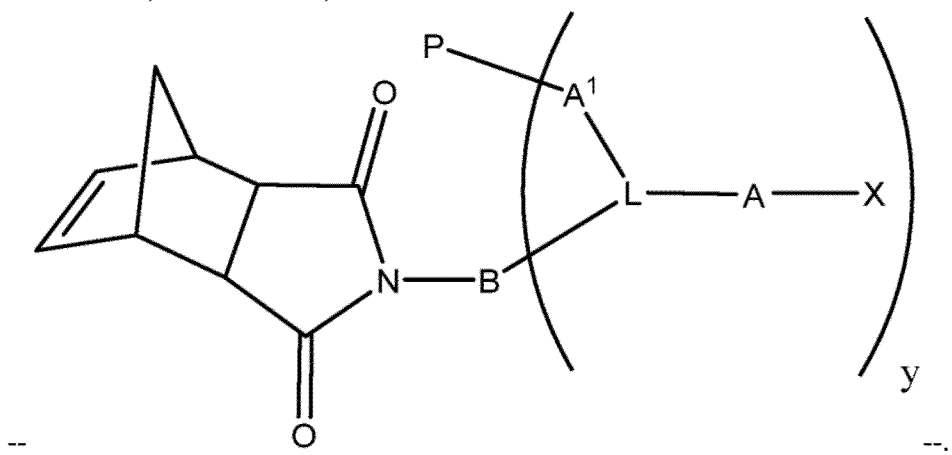

--.